(12) United States Patent
Green et al.

(10) Patent No.: US 6,329,518 B1
(45) Date of Patent: Dec. 11, 2001

(54) PLANT FATTY ACID EPOXYGENASE GENES AND USES THEREFOR

(75) Inventors: Allan Green, Barton; Surinder Singh, Downer, both of (AU); Marit Lenman, Lund; Sten Stymne, Svalov, both of (SE)

(73) Assignees: BASF Plant Science GmbH, Ludwigshafen (DE); Commonwealth Scientific & Industrial Research Organisation, Campbell (AU)

( * ) Notice: Subject to any disclaimer, the term of this patent is extended or adjusted under 35 U.S.C. 154(b) by 0 days.

(21) Appl. No.: 09/059,769

(22) Filed: Apr. 14, 1998

Related U.S. Application Data
(60) Provisional application No. 60/050,403, filed on Jun. 20, 1997, and provisional application No. 60/043,706, filed on Apr. 16, 1997.

(30) Foreign Application Priority Data

Apr. 15, 1997 (AU) .............................................. PO6223/97
Apr. 15, 1997 (AU) .............................................. PO6226/97

(51) Int. Cl.[7] ............................ C12N 15/82; C07H 21/04
(52) U.S. Cl. ........................ 536/23.6; 800/281; 435/69.1
(58) Field of Search ................................ 536/23.6, 23.2; 435/69.1, 468; 800/281

(56) References Cited

FOREIGN PATENT DOCUMENTS

| WO 89/05852 | 6/1989 | (WO) | ............................... C12N/9/22 |
| WO 97/37033 | 9/1997 | (WO) | ............................... C12P/7/64 |

OTHER PUBLICATIONS

Van de Loo et al. PNAS, USA 92:6743–6747.*
Bafor et al. (1993) "Biosynthesis of Vernoleate (cis–12–Eposyoctadeca–cis–9Oenoate) in Microsomal Preparations from Developing Endosperm of *Euphorbia lagascae*" *Archives of Biochemistry and Biophysics* 303(1):145–151.
Banas et al. (1997) In: Williams, J.P., Mobasher, K.U., Lem, N.W. (Eds) Physiology, Biochemistry and Molecular Biology of Plant Lipids. Kluwer Academic Publisher, Dordrecht. In press. "Biosynthesis of an Acetylenic Fatty Acid in Microsomal Preparations From Developing Seeds of *Crepis Alpina*" pp. 57–59.
Blee et al. (1993) "Regio–and Stereoselectivity of Cytochrome P–450 and Peroxygenase–Dependent Formation of CIS–12, 13–Epoxy–9(Z)–Octadecenoic Acid (Vernolic Acid) in Euphorbia Lagascae" *Biochemical and Biophysical Research Communications* 197(2):778–784.
Blee et al. (1993) "Mechanism of Reaction of Fatty Acid Hydroperoxides with Soybean Peroxygenase" *The Journal of Biological Chemistry* 268(3):1708–1715.
Blee and Schuber (1990) "Efficient Epoxidation of Unsaturated Fatty Acids by a Hydroperoxide–dependent Oxygenase" *The Journal of Biological Chemistry* 265(22):12887–12894.
Bozak et al. (1990) "Sequence analysis of ripening–related cytochrome P–450 cDNAs from avocado fruit" *Proc. Natl. Acad. Sci. USA* 87:3904–3908.
Dolferus et al. (1994) "Differential Interactions of Promoter Elements in Stress Responses of the *Arabidopsis Adh Gene*" *Plant Physiol.* 105:1075–1087.
Engeseth and Stymne (1996) "Desaturation of Oxygenated Fatty Acids in *Lesquerella* and Other Oil Seeds" *Planta* 198:238–245.
Needleman and Wunsch (1970) "A General Method Applicable to the Search for Similarities in the Amino Acid Sequence of Two Proteins" *J. Mol. Biol.* 48:443–453.
Shanklin et al. (1994) "Eight Histidine Residues Are Catalytically Essential in a Membrane–Associated Iron Enzyme, Stearoyl–CoA Sesaturase, and Are Conserved in Alkane Hydroxylase and Xylene Monooxygenase" *Biochemistry* 33:12787–12794.
Valvekens et al. (1988) "*Agrobacterium tumefaciens*–mediated transformation of *Arbidopsis thaliana* root explants by using knamycin selection" *Proc. Natl. Acad. Sci. USA* 85:5536–5540.

* cited by examiner

*Primary Examiner*—Elizabeth F. McElwain
(74) *Attorney, Agent, or Firm*—Greenlee Winner and Sullivan PC

(57) ABSTRACT

The present invention relates generally to novel genetic sequences which encode fatty acid epoxygenase enzymes. In particular, the present invention relates to genetic sequences which encode fatty acid Δ12-epoxygenase enzymes comprising mixed function monooxygenase enzymes. More preferably, the present invention provides cDNA sequences which encode plant fatty acid epoxygenases, in particular the *Crepis palaestina* Δ12-epoxygenase and homologues, analogues and derivatives thereof. The genetic sequences of the present invention provide the means by which fatty acid metabolism may be altered or manipulated in organisms such as yeasts, moulds, bacteria, insects, birds, mammals and plants, in particular to convert unsaturated fatty acids to epoxygenated fatty acids therein. The invention extends to genetically modified oil-accumulating organisms transformed with the subject genetic sequences and to the oils derived therefrom. The oils thus produced provide the means for the cost-effective raw materials for use in the efficient production of coatings, resins, glues, plastics, surfactants and lubricants, amongst others.

8 Claims, 23 Drawing Sheets

```
         1                                                        50
Cpal2   ......MGAG GR.......... .......... ..GRTSEKSV MERVSVDPVT FSLSELKQAI
CrepX   ......MGAG GR.......... .......... ..GRTSEKSV MERVSVDPVT FSLSDLKQAI
Vgal1   .......... .......... .......... .......... .......... ..........
Crep1   ......MGGG GR.......... .......... ..GRTSQKPL MERVSVDP.P FTVSDLKQAI
L26296  ......MGAG GRMPV.....P TSSKKSETDT TKRVPCEKPP FSVGDLKKAI
X91139  ......MGAG GRMQV.....S PSPKKSETDT LKRVPCETPP FTVGELKKAI
L43921  ......MGAG GRTDV.....P PANRKSEVDP LKRVPFEKPQ FSLSQIKKAI
X92847  ......MGAG GRMSA.....P NGETEVKRNP LQKVPTSKPP FTVGDIKKAI
L43920  MGLAKETTMG GRGRV.....A KVEVQGK.KP LSRVPNTKPP FTVGQLKKAI
U22378  ......MGGG GRMSTVITSN NSEKKGGSSH LKRAPHTKPP FTLGDLKRAI
```

FIGURE 2A

|         | 51         |            |            |            | 100        |
|---------|------------|------------|------------|------------|------------|
| Cpal2   | PPHCFQRSVI | RSSYYVVQDL | IIAYIFYFLA | NTYIPTLPTS | LAYLAWPVYW |
| CrepX   | PPHCFQRSVI | RSSYYVVQDL | IIAYIFYFLA | NTYIPNLPHP | LAYLAWPLYW |
| Vgal1   | .......... | .......... | .......... | .......... | .......... |
| Crep1   | PPHCFKRSVI | RSSYYIVHDA | IIAYIFYFLA | DKYIPILPAP | LAYLAWPLYW |
| L26296  | PPHCFKRSIP | RSFSYLISDI | IIASCFYYVA | TNYFSLLPQP | LSYLAWPLYW |
| X91139  | PPHCFKRSIP | RSFSYLIWDI | IVASCFYYVA | TTYFPLLPHP | LSYVAWPLYW |
| L43921  | PPHCFQRSVL | RSFSYVVVYDL | TIAFCLYYVA | THYFHLLPGP | LSFRGMAIYW |
| X92847  | PPHCFQRSLI | RSFSYVVVYDL | ILVSIMYYVA | NTYFHLLPSP | YCYIAWPIYW |
| L43920  | PPHCFQRSLL | TSFSYVVVYDL | SFAF.IFYIA | TTYFHLLPQP | FSLIAWPIYW |
| U22378  | PPHCFERSFV | RSFSYVAYDV | CLSFLFYSIA | TNFFPYISSP | LSYVAWLVYW |

FIGURE 2B

```
        101                                                      150
Cpal2   FCQASVLTGL  WILGHECGHH  AFSNYTWFDD  TVGFILHSFL  LTPYFSWKFS
CrepX   FCQASVLTGL  WILGHECGHH  AYSNYTWVDD  TVGFIIHSFL  LTPYFSWKYS
Vgal1   ..........  ........HH  AFSDYQWIDD  TVGFILHFAL  FTPYFSWKYS
Crep1   FCQASILTGL  WVIGHECGHH  AFSDYQWVDD  TVGFILHSFL  MTPYFSWKYS
L26296  ACQGCVLTGI  WVIAHECGHH  AFSDYQWLDD  TVGLIFHSFL  LVPYFSWKYS
X91139  ACQGVVLTGV  WVIAHECGHH  AFSDYQWLDD  TVGLIFHSFL  LVPYFSWKYS
L43921  AVQGCILTGV  WVIAHECGHH  AFSDYQLLDD  IVGLILHSAL  LVPYFSWKYS
X92847  ICQGCVCTGI  WVNAHECGHH  AFSDYQWVDD  TVGLILHSAL  LVPYFSWKYS
L43920  VLQGCLLTGV  WVIAHECGHH  AFSKYQWVDD  VVGLTLHSTL  LVPYFSWKIS
U22378  LFQGCILTGL  WVIGHECGHH  AFSEYQLADD  IVGLIVHSAL  LVPYFSWKYS
```

FIGURE 2C

```
                151                                                           200
Cpal2    HRNHHSNTSS  IDNDEVYIPK  SKSKLARIYK  LLNNPPGRLL  VLIIMFTLGF
CrepX    HRNHHSNTSS  IDNDEVYIPK  SKSKLKRIYK  LLNNPPGRLL  VLVIMFTLGF
Vgall    HRNHHANTNS  LVTDEVYIPK  VKSKVKIYSK  ILNNPPGRLL  TLAFRLIVGF
Crepl    HRNHHANTNS  LDNDEVYIPK  SKAKVALYYK  VLNHPPGRLL  IMFITFTLGF
L26296   HRRHHSNTGS  LERDEVFVPK  QKSAIKWYGK  YLNNPLGRIM  MLTVQFVLGW
X91139   HRRHHSNTGS  LERDEVFVPK  KKSDIKWYGK  YLNNPLGRTV  MLTVQFTLGW
L43921   HRRHHSNTGS  LERDEVFVPK  QKSCIKWYSK  YLNNPPGRVL  TLAVTLTLGW
X92847   HRRHHSNTGS  LERDEVFVPK  PKSQLGWYSK  YLNNPPGRVL  SLTITLTLGW
L43920   HRRHHSNTGS  LDRDEVFVPK  PKSKVAWFSK  YLNNPLGRAV  SLLVTLTIGW
U22378   HRRHHSNIGS  LERDEVFVPK  SKSKISWYSK  YSNNPPGRVL  TLAATLLLGW
```

FIGURE 2D

|        | 201        |             |            |            | 250        |
|--------|------------|-------------|------------|------------|------------|
| Cpal2  | PLYLLTNISG | KKY.DRFANH  | FDPMSPIFKE | RERFQVFLSD | LGLLAVFYGI |
| CrepX  | PLYLLTNISG | KKY.DRFANH  | FDPMSPIFKE | RERFQVFLSD | LGLLAVFYGI |
| Vgal1  | PLYLFTNVSG | KKY.ERFANH  | FDPMSPIFTE | REHVQVLLSD | FGLIAVAYVV |
| Crep1  | PLYLFTNISG | KKY.ERFANH  | FDPMSPIFKE | RERFQVLLSD | LGLLAVLYGV |
| L26296 | PLYLAFNVSG | RPY.DGFACH  | FFPNAPIYND | RERLQIYLSD | AGILAVCFGL |
| X91139 | PLYWAFNVSG | RPYPEGFACH  | FHPNAPIYND | RERLQIYVSD | AGILAVCYGL |
| L43921 | PLYLALNVSG | RPY.DRFACH  | YDPYGPIYSD | RERLQIYISD | AGVLAVVYGL |
| X92847 | PLYLAFNVSG | RPY.DRFACH  | YDPYGPIYNN | RERLQIFISD | AGVLGVCYLL |
| L43920 | PMYLAFNVSG | RPY.DSFASH  | YHPYAPIYSN | RERLLIYVSD | VALFSVTYSL |
| U22378 | PLYLAFNVSG | RPY.DRFACH  | YDPYGPIFSE | RERLQIYIAD | LGIFATTFVL |

FIGURE 2E

```
       251                                                          300
Cpal2  KVAVANKGAA  WVACMYGVPV  LGVFTFFDVI  TFLHHTHQSS  PHYDSTEWNW
CrepX  KVAVANKGAA  WVACMYGVPV  LGVFTFFDVI  TFLHHTHQSS  PHYDSTEWNW
Vgal1  RQAVLAKGGA  WVMCIYGVPV  LAVNAFFVLI  TYLHHTHLSL  PHYDSSEWDW
Crep1  KLAVAAKGAA  WVTCIYGIPV  LGVFIFFDII  TYLHHTHLSL  PHYDSSEWNW
L26296 YRYAAAQGMA  SMICLYGVPL  LIVNAFLVLI  TYLQHTHPSL  PHYDSSEWDW
X91139 YRYAAAQGVA  SMVCLYGVPL  LIVNAFLVLI  TYLQHTHPSL  PHYDSSEWDW
L43921 FRLAMAKGLA  WVVCVYGVPL  LVVNGFLVLI  TFLQHTHPAL  PHYTSSEWDW
X92847 YRIALVKGLA  WLVCVYGVPL  LVVNGFLVTI  TYLQHTHPSL  PHYDSTEWDW
L43920 YRVATLKGLV  WLLCVYGVPL  LIVNGFLVTI  TYLQHTHFAL  PHYDSSEWDW
U22378 YQATMAKGLA  WVMRIYGVPL  LIVNCFLVMI  TYLQHTHPAI  PRYGSSEWDW
```

FIGURE 2F

```
       301                                                  350
Cpal2   IRGALSAIDR DFGFLNSVFH DVTHTHVMHH LFSYIPHYHA KEARDAIKPI
CrepX   IRGALSAIDR DFGFLNSVFH DVTHTHVMHH LFSYIPHYHA KEARDAIKPI
Vgal1   LR........ .......... .......... .......... ..........
Crep1   LRGALSTIDR DFGFLNSVLH DVTHTHVMHH LFSYIPHYHA KEARDAINTV
L26296  LRGALATVDR DYGILNKVFH NITDTHVAHH LFSTMPHYNA MEATKAIKPI
X91139  LRGALATVDR DYGILNKVFH NITDTHVAHH LFSTMPHYNA MEVTKAIKPI
L43921  LRGALATVDR DYGILNKVFH NITDTHVAHH LFSTMPHYHA MEATKAIKPI
X92847  LRGALATCDR DYGVLNKVFH NITDTHVVHH LFSTMPHYHA MEATKAVKPL
L43920  LKGALATMDR DYGILNKVFH HITDTHVAHH LFSTMPHYHA MEATNAIKPI
U22378  LRGAMVTVDR DYGVLNKVFH NIADTHVAHH LFATVPHYHA MEATKAIKPI
```

FIGURE 2G

|        | 351 |   |   |   | 394 |
|--------|-----|---|---|---|-----|
| Cpal2  | LGDFYMIDRT | PILKAMWREG | RECMYIEPDS | ..KLKGVYWY | .HKL |
| CrepX  | LGDFYMIDRT | PILKAMWREG | RECMYIEPDS | ..KLKGVYWY | .HKL |
| Vgal1  | .......... | .......... | .......... | .......... | .... |
| Crep1  | LGDFYKIDRT | PILKAMWREA | KECIFIEPEK | GRESKGVYWY | .NKF |
| L26296 | LGDYYQFDGT | PWYVAMYREA | KECIYVEPDR | EGDKKGVYWY | NNKL |
| X91139 | LGDYYQFDGT | PWVKAMWREA | KECIYVEPDR | QGEKKGVFWY | NNKL |
| L43921 | LGEYYRFDET | PFVKAMWREA | RECIYVEPDQ | STESKGVFWY | NNKL |
| X92847 | LGDYYQFDGT | PIYKEMWREA | KECLYVEKDE | SSQGKGVFWY | KNKL |
| L43920 | LGEYYQFDDT | PFYKALWREA | RECLYVEPDE | GTSEKGVYWY | RNKY |
| U22378 | MGEYYRYDGT | PFYKALWREA | KECLFVEPDE | GAPTQGVFWY | RNKY |

A
   
1   2   3   4
B
1   2   3
FIGURE 5

A
1    2    3    4
B
1    2    3
FIGURE 7

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
      (A) LENGTH: 1358 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: CDS
      (B) LOCATION: 30..1151

(xi) SEQUENCE DESCRIPTION: SEQ ID NO:1:

```
GAGAAGTTGA CCATAAATCA TTTATCAAC ATG GGT GCC GGC GGT CGT GGT CGG         53
                                Met Gly Ala Gly Gly Arg Gly Arg
                                  1               5

ACA TCG GAA AAA TCG GTC ATG GAA CGT GTC TCA GTT GAT CCA GTA ACC        101
Thr Ser Glu Lys Ser Val Met Glu Arg Val Ser Val Asp Pro Val Thr
         10              15                  20

TTC TCA CTG AGT GAA TTG AAG CAA GCA ATC CCT CCC CAT TGC TTC CAG        149
Phe Ser Leu Ser Glu Leu Lys Gln Ala Ile Pro Pro His Cys Phe Gln
 25              30                  35                  40
```

-continued

| | | |
|---|---|---|
| AGA TCT GTA ATC CGC TCA TCT TAC TAT GTT GTT CAA GAT CTC ATT ATT<br>Arg Ser Val Ile Arg Ser Ser Tyr Tyr Val Val Gln Asp Leu Ile Ile<br>                      45                              50                          55 | 197 |
| GCC TAC ATC TTC TAC TTC CTT GCC AAC ACA TAT ATC CCT ACT CTT CCT<br>Ala Tyr Ile Phe Tyr Phe Leu Ala Asn Thr Tyr Ile Pro Thr Leu Pro<br>                  60                              65                      70 | 245 |
| ACT AGT CTA GCC TAC TTA GCT TGG CCC GTT TAC TGG TTC TGT CAA GCT<br>Thr Ser Leu Ala Tyr Leu Ala Trp Pro Val Tyr Trp Phe Cys Gln Ala<br>            75                          80                          85 | 293 |
| AGC GTC CTC ACT GGC TTA TGG ATC CTC GGC CAC GAA TGT GGT CAC CAT<br>Ser Val Leu Thr Gly Leu Trp Ile Leu Gly His Glu Cys Gly His His<br>      90                        95                          100 | 341 |
| GCC TTT AGC AAC TAC ACA TGG TTT GAC GAC ACT GTG GGC TTC ATC CTC<br>Ala Phe Ser Asn Tyr Thr Trp Phe Asp Asp Thr Val Gly Phe Ile Leu<br>105                      110                      115                      120 | 389 |
| CAC TCA TTT CTC CTC ACC CCG TAT TTC TCT TGG AAA TTC AGT CAC CGG<br>His Ser Phe Leu Leu Thr Pro Tyr Phe Ser Trp Lys Phe Ser His Arg<br>                  125                          130                      135 | 437 |
| AAT CAC CAT TCC AAC ACA AGT TCG ATT GAT AAC GAT GAA GTT TAC ATT<br>Asn His His Ser Asn Thr Ser Ser Ile Asp Asn Asp Glu Val Tyr Ile<br>            140                          145                      150 | 485 |
| CCG AAA AGC AAG TCC AAA CTC GCG CGT ATC TAT AAA CTT CTT AAC AAC<br>Pro Lys Ser Lys Ser Lys Leu Ala Arg Ile Tyr Lys Leu Leu Asn Asn<br>                  155                          160                      165 | 533 |
| CCA CCT GGT CGG CTG TTG GTT TTG ATT ATC ATG TTC ACC CTA GGA TTT<br>Pro Pro Gly Arg Leu Leu Val Leu Ile Ile Met Phe Thr Leu Gly Phe<br>      170                        175                          180 | 581 |
| CCT TTA TAC CTC TTG ACA AAT ATT TCC GGC AAG AAA TAC GAC AGG TTT<br>Pro Leu Tyr Leu Leu Thr Asn Ile Ser Gly Lys Lys Tyr Asp Arg Phe<br>185                      190                      195                      200 | 629 |
| GCC AAC CAC TTC GAC CCC ATG AGT CCA ATT TTC AAA GAA CGT GAG CGG<br>Ala Asn His Phe Asp Pro Met Ser Pro Ile Phe Lys Glu Arg Glu Arg<br>                  205                          210                      215 | 677 |
| TTT CAG GTC TTC CTT TCG GAT CTT GGT CTT CTT GCC GTG TTT TAT GGA<br>Phe Gln Val Phe Leu Ser Asp Leu Gly Leu Leu Ala Val Phe Tyr Gly<br>            220                          225                      230 | 725 |
| ATT AAA GTT GCT GTA GCA AAT AAA GGA GCT GCT TGG GTA GCG TGC ATG<br>Ile Lys Val Ala Val Ala Asn Lys Gly Ala Ala Trp Val Ala Cys Met<br>      235                        240                        245 | 773 |
| TAT GGA GTT CCG GTA TTA GGC GTA TTT ACC TTT TTC GAT GTG ATC ACC<br>Tyr Gly Val Pro Val Leu Gly Val Phe Thr Phe Phe Asp Val Ile Thr<br>250                      255                      260 | 821 |
| TTC TTG CAC CAC ACC CAT CAG TCG TCG CCT CAT TAT GAT TCA ACT GAA<br>Phe Leu His His Thr His Gln Ser Ser Pro His Tyr Asp Ser Thr Glu<br>265                      270                      275                      280 | 869 |
| TGG AAC TGG ATC AGA GGG GCC TTG TCA GCA ATC GAT AGG GAC TTT GGA<br>Trp Asn Trp Ile Arg Gly Ala Leu Ser Ala Ile Asp Arg Asp Phe Gly<br>                  285                          290                      295 | 917 |
| TTC CTG AAT AGT GTT TTC CAT GAT GTT ACA CAC ACT CAT GTC ATG CAT<br>Phe Leu Asn Ser Val Phe His Asp Val Thr His Thr His Val Met His<br>            300                          305                      310 | 965 |
| CAT TTG TTT TCA TAC ATT CCA CAC TAT CAT GCA AAG GAG GCA AGG GAT<br>His Leu Phe Ser Tyr Ile Pro His Tyr His Ala Lys Glu Ala Arg Asp<br>                  315                          320                      325 | 1013 |
| GCA ATC AAG CCA ATC TTG GGC GAC TTT TAT ATG ATC GAC AGG ACT CCA<br>Ala Ile Lys Pro Ile Leu Gly Asp Phe Tyr Met Ile Asp Arg Thr Pro<br>330                      335                      340 | 1061 |
| ATT TTA AAA GCA ATG TGG AGA GAG GGC AGG GAG TGC ATG TAC ATC GAG<br>Ile Leu Lys Ala Met Trp Arg Glu Gly Arg Glu Cys Met Tyr Ile Glu | 1109 |

```
345                350                355                360
CCT GAT AGC AAG CTC AAA GGT GTT TAT TGG TAT CAT AAA TTG                        1151
Pro Asp Ser Lys Leu Lys Gly Val Tyr Trp Tyr His Lys Leu
                    365                370

TGATCATATG CAAAATGCAC ATGCATTTTC AAACCCTCTA GTTACGTTTG TTCTATGTAT            1211

AATAAACCGC CGGTCCTTTG GTTGACTATG CCTAAGCCAG GCGAAACAGT TAAATAATAT            1271

CGGTATGATG TGTAATGAAA GTATGTGGTT GTCTGGTTTT GTTGCTATGA AGAAAGTAT             1331

GTGGTTGTCG GTCAAAAAAA AAAAAAA                                                1358

(2) INFORMATION FOR SEQ ID NO:2:

(i) SEQUENCE CHARACTERISTICS:
        (A) LENGTH: 374 amino acids
        (B) TYPE: amino acid
        (D) TOPOLOGY: linear (ii) MOLECULE TYPE: protein (xi) SEQUENCE DESCRIPTION: SEQ ID NO:2:

Met Gly Ala Gly Gly Arg Gly Arg Thr Ser Glu Lys Ser Val Met Glu
 1               5                  10                  15

Arg Val Ser Val Asp Pro Val Thr Phe Ser Leu Ser Glu Leu Lys Gln
            20                  25                  30

Ala Ile Pro Pro His Cys Phe Gln Arg Ser Val Ile Arg Ser Ser Tyr
        35                  40                  45

Tyr Val Val Gln Asp Leu Ile Ile Ala Tyr Ile Phe Tyr Phe Leu Ala
    50                  55                  60

Asn Thr Tyr Ile Pro Thr Leu Pro Thr Ser Leu Ala Tyr Leu Ala Trp
65                  70                  75                  80

Pro Val Tyr Trp Phe Cys Gln Ala Ser Val Leu Thr Gly Leu Trp Ile
                85                  90                  95

Leu Gly His Glu Cys Gly His His Ala Phe Ser Asn Tyr Thr Trp Phe
            100                 105                 110

Asp Asp Thr Val Gly Phe Ile Leu His Ser Phe Leu Leu Thr Pro Tyr
        115                 120                 125

Phe Ser Trp Lys Phe Ser His Arg Asn His Ser Asn Thr Ser Ser
    130                 135                 140

Ile Asp Asn Asp Glu Val Tyr Ile Pro Lys Ser Lys Ser Lys Leu Ala
145                 150                 155                 160

Arg Ile Tyr Lys Leu Leu Asn Asn Pro Pro Gly Arg Leu Leu Val Leu
                165                 170                 175

Ile Ile Met Phe Thr Leu Gly Phe Pro Leu Tyr Leu Leu Thr Asn Ile
            180                 185                 190

Ser Gly Lys Lys Tyr Asp Arg Phe Ala Asn His Phe Asp Pro Met Ser
        195                 200                 205

Pro Ile Phe Lys Glu Arg Glu Arg Phe Gln Val Phe Leu Ser Asp Leu
    210                 215                 220

Gly Leu Leu Ala Val Phe Tyr Gly Ile Lys Val Ala Val Ala Asn Lys
225                 230                 235                 240

Gly Ala Ala Trp Val Ala Cys Met Tyr Gly Val Pro Val Leu Gly Val
                245                 250                 255

Phe Thr Phe Phe Asp Val Ile Thr Phe Leu His His Thr His Gln Ser
            260                 265                 270

Ser Pro His Tyr Asp Ser Thr Glu Trp Asn Trp Ile Arg Gly Ala Leu
        275                 280                 285
```

```
Ser Ala Ile Asp Arg Asp Phe Gly Phe Leu Asn Ser Val Phe His Asp
    290                 295                 300

Val Thr His Thr His Val Met His His Leu Phe Ser Tyr Ile Pro His
305                 310                 315                 320

Tyr His Ala Lys Glu Ala Arg Asp Ala Ile Lys Pro Ile Leu Gly Asp
                325                 330                 335

Phe Tyr Met Ile Asp Arg Thr Pro Ile Leu Lys Ala Met Trp Arg Glu
            340                 345                 350

Gly Arg Glu Cys Met Tyr Ile Glu Pro Asp Ser Lys Leu Lys Gly Val
        355                 360                 365

Tyr Trp Tyr His Lys Leu
    370
```

(2) INFORMATION FOR SEQ ID NO:3:

(i) SEQUENCE CHARACTERISTICS:
        (A) LENGTH: 1312 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Crepis sp.

(ix) FEATURE:
        (A) NAME/KEY: CDS
        (B) LOCATION: 26..1147

(xi) SEQUENCE DESCRIPTION: SEQ ID NO:3:

```
TGTTGACCAT AAATCATCTA TCAAC ATG GGT GCC GGC GGC CGT GGT CGG ACA        52
                           Met Gly Ala Gly Gly Arg Gly Arg Thr
                             1               5

TCG GAA AAG TCG GTC ATG GAA CGT GTC TCA GTT GAT CCA GTA ACC TTC       100
Ser Glu Lys Ser Val Met Glu Arg Val Ser Val Asp Pro Val Thr Phe
 10              15                  20                  25

TCA CTG AGT GAT TTG AAG CAA GCA ATC CCT CCA CAT TGC TTC CAG CGA       148
Ser Leu Ser Asp Leu Lys Gln Ala Ile Pro Pro His Cys Phe Gln Arg
             30                  35                  40

TCT GTC ATC CGT TCA TCT TAT TAC GTT GTT CAG GAT CTC ATA ATT GCC       196
Ser Val Ile Arg Ser Ser Tyr Tyr Val Val Gln Asp Leu Ile Ile Ala
         45                  50                  55

TAC ATC TTC TAC TTC CTT GCC AAC ACA TAT ATC CCT AAT CTC CCT CAT       244
Tyr Ile Phe Tyr Phe Leu Ala Asn Thr Tyr Ile Pro Asn Leu Pro His
     60                  65                  70

CCT CTA GCC TAC TTA GCT TGG CCG CTT TAC TGG TTC TGT CAA GCT AGC       292
Pro Leu Ala Tyr Leu Ala Trp Pro Leu Tyr Trp Phe Cys Gln Ala Ser
 75                  80                  85

GTC CTC ACT GGG TTA TGG ATC CTC GGC CAT GAA TGT GGT CAC CAT GCC       340
Val Leu Thr Gly Leu Trp Ile Leu Gly His Glu Cys Gly His His Ala
 90                  95                 100                 105

TAT AGC AAC TAC ACA TGG GTT GAC GAC ACT GTG GGC TTC ATC ATC CAT       388
Tyr Ser Asn Tyr Thr Trp Val Asp Asp Thr Val Gly Phe Ile Ile His
                110                 115                 120

TCA TTT CTC CTC ACC CCG TAT TTC TCT TGG AAA TAC AGT CAC CGG AAT       436
Ser Phe Leu Leu Thr Pro Tyr Phe Ser Trp Lys Tyr Ser His Arg Asn
            125                 130                 135

CAC CAT TCC AAC ACA AGT TCG ATT GAT AAC GAT GAA GTT TAC ATT CCG       484
His His Ser Asn Thr Ser Ser Ile Asp Asn Asp Glu Val Tyr Ile Pro
        140                 145                 150
```

| | | | |
|---|---|---|---|
| AAA AGC AAG TCC AAA CTC AAG CGT ATC TAT AAA CTT CTT AAC AAC CCA | | | 532 |
| Lys Ser Lys Ser Lys Leu Lys Arg Ile Tyr Lys Leu Leu Asn Asn Pro | | | |
| 155 160 165 | | | |
| CCT GGT CGA CTG TTG GTT TTG GTT ATC ATG TTC ACC CTA GGA TTT CCT | | | 580 |
| Pro Gly Arg Leu Leu Val Leu Val Ile Met Phe Thr Leu Gly Phe Pro | | | |
| 170 175 180 185 | | | |
| TTA TAC CTC TTG ACA AAT ATT TCC GGC AAG AAA TAC GAT AGG TTT GCC | | | 628 |
| Leu Tyr Leu Leu Thr Asn Ile Ser Gly Lys Lys Tyr Asp Arg Phe Ala | | | |
| 190 195 200 | | | |
| AAC CAC TTC GAC CCC ATG AGT CCA ATT TTC AAA GAA CGT GAG CGG TTT | | | 676 |
| Asn His Phe Asp Pro Met Ser Pro Ile Phe Lys Glu Arg Glu Arg Phe | | | |
| 205 210 215 | | | |
| CAG GTC TTC CTT TCG GAT CTT GGT CTT CTT GCT GTG TTT TAT GGA ATT | | | 724 |
| Gln Val Phe Leu Ser Asp Leu Gly Leu Leu Ala Val Phe Tyr Gly Ile | | | |
| 220 225 230 | | | |
| AAA GTT GCT GTA GCA AAT AAA GGA GCT GCT TGG GTG GCG TGC ATG TAT | | | 772 |
| Lys Val Ala Val Ala Asn Lys Gly Ala Ala Trp Val Ala Cys Met Tyr | | | |
| 235 240 245 | | | |
| GGA GTT CCG GTG CTA GGC GTA TTT ACC TTT TTC GAT GTG ATC ACG TTC | | | 820 |
| Gly Val Pro Val Leu Gly Val Phe Thr Phe Phe Asp Val Ile Thr Phe | | | |
| 250 255 260 265 | | | |
| TTA CAC CAC ACC CAT CAG TCG TCG CCT CAT TAT GAT TCA ACT GAA TGG | | | 868 |
| Leu His His Thr His Gln Ser Ser Pro His Tyr Asp Ser Thr Glu Trp | | | |
| 270 275 280 | | | |
| AAC TGG ATC AGA GGG GCT TTG TCA GCA ATC GAT AGN GAC TTT GGG TTC | | | 916 |
| Asn Trp Ile Arg Gly Ala Leu Ser Ala Ile Asp Arg Asp Phe Gly Phe | | | |
| 285 290 295 | | | |
| CTG AAT AGT GTT TTC CAT GAT GTN ACA CAC ACT CAC GTC ATG CAT CAT | | | 964 |
| Leu Asn Ser Val Phe His Asp Val Thr His Thr His Val Met His His | | | |
| 300 305 310 | | | |
| TTG TTT TCA TAC ATT CCA CAC TAT CAT GCA AAG GAA GCA AGG GAT GCA | | | 1012 |
| Leu Phe Ser Tyr Ile Pro His Tyr His Ala Lys Glu Ala Arg Asp Ala | | | |
| 315 320 325 | | | |
| ATC AAA CCG ATC TTG GGC GAC TTT TAT ATG ATC GAT AGG ACT CCA ATT | | | 1060 |
| Ile Lys Pro Ile Leu Gly Asp Phe Tyr Met Ile Asp Arg Thr Pro Ile | | | |
| 330 335 340 345 | | | |
| TTA AAA GCA ATG TGG AGA GAG GGC AGG GAA TGC ATG TAC ATC GAG CCT | | | 1108 |
| Leu Lys Ala Met Trp Arg Glu Gly Arg Glu Cys Met Tyr Ile Glu Pro | | | |
| 350 355 360 | | | |
| GAT AGC AAG CTC AAA GGT GTT TAT TGG TAT CAT AAA TTG TGATCATATG | | | 1157 |
| Asp Ser Lys Leu Lys Gly Val Tyr Trp Tyr His Lys Leu | | | |
| 365 370 | | | |
| CAAAATGCAC ATGCATTTTC AAACCCTCTA GTTACCTTTG TTCTATGTAT AATAAGACCG | | | 1217 |
| CCGGTCCTAT GGTTTTCTAT GCCTAAGCCA GGCGAAATAG TTAAATAATA TCGGTATGAT | | | 1277 |
| GTAATGAAAG TATGTGGTTG TCTAAAAAAA AAAAA | | | 1312 |

(2) INFORMATION FOR SEQ ID NO:4:

(i) SEQUENCE CHARACTERISTICS:
        (A) LENGTH: 374 amino acids
        (B) TYPE: amino acid
        (D) TOPOLOGY: linear (ii) MOLECULE TYPE: protein (xi) SEQUENCE DESCRIPTION: SEQ ID NO:4:

Met Gly Ala Gly Gly Arg Gly Arg Thr Ser Glu Lys Ser Val Met Glu
1               5                   10                  15

Arg Val Ser Val Asp Pro Val Thr Phe Ser Leu Ser Asp Leu Lys Gln
            20                  25                  30

```
Ala Ile Pro Pro His Cys Phe Gln Arg Ser Val Ile Arg Ser Ser Tyr
         35                  40                  45

Tyr Val Val Gln Asp Leu Ile Ile Ala Tyr Ile Phe Tyr Phe Leu Ala
     50                  55                  60

Asn Thr Tyr Ile Pro Asn Leu Pro His Pro Leu Ala Tyr Leu Ala Trp
 65                  70                  75                  80

Pro Leu Tyr Trp Phe Cys Gln Ala Ser Val Leu Thr Gly Leu Trp Ile
                 85                  90                  95

Leu Gly His Glu Cys Gly His Ala Tyr Ser Asn Tyr Thr Trp Val
             100                 105                 110

Asp Asp Thr Val Gly Phe Ile Ile His Ser Phe Leu Leu Thr Pro Tyr
             115                 120                 125

Phe Ser Trp Lys Tyr Ser His Arg Asn His His Ser Asn Thr Ser Ser
130                 135                 140

Ile Asp Asn Asp Glu Val Tyr Ile Pro Lys Ser Lys Ser Lys Leu Lys
145                 150                 155                 160

Arg Ile Tyr Lys Leu Leu Asn Asn Pro Pro Gly Arg Leu Leu Val Leu
                 165                 170                 175

Val Ile Met Phe Thr Leu Gly Phe Pro Leu Tyr Leu Leu Thr Asn Ile
             180                 185                 190

Ser Gly Lys Lys Tyr Asp Arg Phe Ala Asn His Phe Asp Pro Met Ser
         195                 200                 205

Pro Ile Phe Lys Glu Arg Glu Arg Phe Gln Val Phe Leu Ser Asp Leu
         210                 215                 220

Gly Leu Leu Ala Val Phe Tyr Gly Ile Lys Val Ala Val Ala Asn Lys
225                 230                 235                 240

Gly Ala Ala Trp Val Ala Cys Met Tyr Gly Val Pro Val Leu Gly Val
                 245                 250                 255

Phe Thr Phe Phe Asp Val Ile Thr Phe Leu His His Thr His Gln Ser
             260                 265                 270

Ser Pro His Tyr Asp Ser Thr Glu Trp Asn Trp Ile Arg Gly Ala Leu
         275                 280                 285

Ser Ala Ile Asp Arg Asp Phe Gly Phe Leu Asn Ser Val Phe His Asp
290                 295                 300

Val Thr His Thr His Val Met His His Leu Phe Ser Tyr Ile Pro His
305                 310                 315                 320

Tyr His Ala Lys Glu Ala Arg Asp Ala Ile Lys Pro Ile Leu Gly Asp
                 325                 330                 335

Phe Tyr Met Ile Asp Arg Thr Pro Ile Leu Lys Ala Met Trp Arg Glu
             340                 345                 350

Gly Arg Glu Cys Met Tyr Ile Glu Pro Asp Ser Lys Leu Lys Gly Val
         355                 360                 365

Tyr Trp Tyr His Lys Leu
    370
```

(2) INFORMATION FOR SEQ ID NO:5:

(i) SEQUENCE CHARACTERISTICS:
        (A) LENGTH: 550 base pairs
        (B) TYPE: nucleic acid
        (C) STRANDEDNESS: single
        (D) TOPOLOGY: linear (ii) MOLECULE TYPE: cDNA (vi) ORIGINAL SOURCE:

(A) ORGANISM: Vernonia galamensis (ix) FEATURE:
        (A) NAME/KEY: CDS
        (B) LOCATION: 1..549

(xi) SEQUENCE DESCRIPTION: SEQ ID NO:5:

```
CAT CAC GCC TTC AGT GAC TAT CAA TGG ATA GAC GAC ACT GTG GGC TTC      48
His His Ala Phe Ser Asp Tyr Gln Trp Ile Asp Asp Thr Val Gly Phe
 1               5                  10                  15

ATC CTT CAC TTT GCA CTC TTC ACC CCT TAT TTC TCT TGG AAA TAC AGT      96
Ile Leu His Phe Ala Leu Phe Thr Pro Tyr Phe Ser Trp Lys Tyr Ser
             20                  25                  30

CAC CGT AAT CAC CAT GCC AAC ACA AAC TCT CTT GTA ACC GAT GAA GTA     144
His Arg Asn His His Ala Asn Thr Asn Ser Leu Val Thr Asp Glu Val
         35                  40                  45

TAC ATC CCT AAA GTT AAA TCC AAG GTC AAG ATT TAT TCC AAA ATC CTT     192
Tyr Ile Pro Lys Val Lys Ser Lys Val Lys Ile Tyr Ser Lys Ile Leu
 50                  55                  60

AAC AAC CCT CCT GGT CGC GTT TTC ACC TTG GCT TTC AGA TTG ATC GTG     240
Asn Asn Pro Pro Gly Arg Val Phe Thr Leu Ala Phe Arg Leu Ile Val
 65                  70                  75                  80

GGT TTT CCT TTA TAC CTT TTC ACC AAT GTT TCA GGC AAG AAA TAC GAA     288
Gly Phe Pro Leu Tyr Leu Phe Thr Asn Val Ser Gly Lys Lys Tyr Glu
                 85                  90                  95

CGT TTT GCC AAC CAT TTT GAT CCC ATG AGT CCC ATT TTC ACC GAG CGT     336
Arg Phe Ala Asn His Phe Asp Pro Met Ser Pro Ile Phe Thr Glu Arg
            100                 105                 110

GAG CAT GTA CAA GTC TTG CTT TCT GAT TTT GGT CTC ATA GCA GTT GCT     384
Glu His Val Gln Val Leu Leu Ser Asp Phe Gly Leu Ile Ala Val Ala
        115                 120                 125

TAC GTG GTT CGT CAA GCT GTA CTG GCT AAA GGA GGT GCT TGG GTG ATG     432
Tyr Val Val Arg Gln Ala Val Leu Ala Lys Gly Gly Ala Trp Val Met
130                 135                 140

TGC ATT TAC GGA GTT CCT GTG CTG GCC GTA AAC GCA TTC TTT GTT TTA     480
Cys Ile Tyr Gly Val Pro Val Leu Ala Val Asn Ala Phe Phe Val Leu
145                 150                 155                 160

ATC ACT TAT CTT CAC CAC ACG CAT CTC TCA CTG CCC CAC TAT GAT AGC     528
Ile Thr Tyr Leu His His Thr His Leu Ser Leu Pro His Tyr Asp Ser
                165                 170                 175

TCA GAA TGG GAC TGG CTA CGA G                                       550
Ser Glu Trp Asp Trp Leu Arg
            180
```

(2) INFORMATION FOR SEQ ID NO:6:

(i) SEQUENCE CHARACTERISTICS:
        (A) LENGTH: 183 amino acids
        (B) TYPE: amino acid
        (D) TOPOLOGY: linear (ii) MOLECULE TYPE: protein (xi) SEQUENCE DESCRIPTION: SEQ ID NO:6:

```
His His Ala Phe Ser Asp Tyr Gln Trp Ile Asp Asp Thr Val Gly Phe
 1               5                  10                  15

Ile Leu His Phe Ala Leu Phe Thr Pro Tyr Phe Ser Trp Lys Tyr Ser
             20                  25                  30

His Arg Asn His His Ala Asn Thr Asn Ser Leu Val Thr Asp Glu Val
         35                  40                  45

Tyr Ile Pro Lys Val Lys Ser Lys Val Lys Ile Tyr Ser Lys Ile Leu
 50                  55                  60
```

```
Asn Asn Pro Pro Gly Arg Val Phe Thr Leu Ala Phe Arg Leu Ile Val
 65                  70                  75                  80

Gly Phe Pro Leu Tyr Leu Phe Thr Asn Val Ser Gly Lys Lys Tyr Glu
                 85                  90                  95

Arg Phe Ala Asn His Phe Asp Pro Met Ser Pro Ile Phe Thr Glu Arg
            100                 105                 110

Glu His Val Gln Val Leu Leu Ser Asp Phe Gly Leu Ile Ala Val Ala
            115                 120                 125

Tyr Val Val Arg Gln Ala Val Leu Ala Lys Gly Gly Ala Trp Val Met
            130                 135                 140

Cys Ile Tyr Gly Val Pro Val Leu Ala Val Asn Ala Phe Phe Val Leu
145                 150                 155                 160

Ile Thr Tyr Leu His His Thr His Leu Ser Leu Pro His Tyr Asp Ser
                165                 170                 175

Ser Glu Trp Asp Trp Leu Arg
            180
```

(2) INFORMATION FOR SEQ ID NO:7:

(i) SEQUENCE CHARACTERISTICS:
        (A) LENGTH: 177 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Crepis alpina (ix) FEATURE:
        (A) NAME/KEY: CDS
        (B) LOCATION: 1..177

(xi) SEQUENCE DESCRIPTION: SEQ ID NO:7:

```
GAA TGC GGT CAC CAT GCC TTC AGC GAC TAC CAG TGG GTT GAC GAC AAT      48
Glu Cys Gly His His Ala Phe Ser Asp Tyr Gln Trp Val Asp Asp Asn
 1               5                  10                  15

GTG GGC TTC ATC CTC CAC TCG TTT CTC ATG ACC CCG TAT TTC TCC TGG      96
Val Gly Phe Ile Leu His Ser Phe Leu Met Thr Pro Tyr Phe Ser Trp
                20                  25                  30

AAA TAC AGC CAC CGG AAC CAC CAT GCC AAC ACA AAT TCG CTT GAC AAC     144
Lys Tyr Ser His Arg Asn His His Ala Asn Thr Asn Ser Leu Asp Asn
            35                  40                  45

GAT GAA GTT TAC ATC CCC AAA AGC AAG GCC AAA                         177
Asp Glu Val Tyr Ile Pro Lys Ser Lys Ala Lys
 50                  55
```

(2) INFORMATION FOR SEQ ID NO:8:

(i) SEQUENCE CHARACTERISTICS:
        (A) LENGTH: 59 amino acids
        (B) TYPE: amino acid
        (D) TOPOLOGY: linear (ii) MOLECULE TYPE: protein (xi) SEQUENCE DESCRIPTION: SEQ ID NO:8:

```
Glu Cys Gly His His Ala Phe Ser Asp Tyr Gln Trp Val Asp Asp Asn
 1               5                  10                  15

Val Gly Phe Ile Leu His Ser Phe Leu Met Thr Pro Tyr Phe Ser Trp
                20                  25                  30
```

```
Lys Tyr Ser His Arg Asn His His Ala Asn Thr Asn Ser Leu Asp Asn
             35                  40                  45

Asp Glu Val Tyr Ile Pro Lys Ser Lys Ala Lys
             50                  55
```

(2) INFORMATION FOR SEQ ID NO:9:

(i) SEQUENCE CHARACTERISTICS:
        (A) LENGTH: 383 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Arabidopsis thaliana (xi) SEQUENCE DESCRIPTION: SEQ ID NO:9:

```
Met Gly Ala Gly Gly Arg Met Pro Val Pro Thr Ser Ser Lys Lys Ser
 1               5                  10                  15

Glu Thr Asp Thr Thr Lys Arg Val Pro Cys Glu Lys Pro Pro Phe Ser
             20                  25                  30

Val Gly Asp Leu Lys Lys Ala Ile Pro Pro His Cys Phe Lys Arg Ser
             35                  40                  45

Ile Pro Arg Ser Phe Ser Tyr Leu Ile Ser Asp Ile Ile Ala Ser
         50                  55                  60

Cys Phe Tyr Tyr Val Ala Thr Asn Tyr Phe Ser Leu Leu Pro Gln Pro
 65                  70                  75                  80

Leu Ser Tyr Leu Ala Trp Pro Leu Tyr Trp Ala Cys Gln Gly Cys Val
                 85                  90                  95

Leu Thr Gly Ile Trp Val Ile Ala His Glu Cys Gly His His Ala Phe
                100                 105                 110

Ser Asp Tyr Gln Trp Leu Asp Asp Thr Val Gly Leu Ile Phe His Ser
                115                 120                 125

Phe Leu Leu Val Pro Tyr Phe Ser Trp Lys Tyr Ser His Arg Arg His
130                 135                 140

His Ser Asn Thr Gly Ser Leu Glu Arg Asp Glu Val Phe Val Pro Lys
145                 150                 155                 160

Gln Lys Ser Ala Ile Lys Trp Tyr Gly Lys Tyr Leu Asn Asn Pro Leu
                165                 170                 175

Gly Arg Ile Met Met Leu Thr Val Gln Phe Val Leu Gly Trp Pro Leu
                180                 185                 190

Tyr Leu Ala Phe Asn Val Ser Gly Arg Pro Tyr Asp Gly Phe Ala Cys
                195                 200                 205

His Phe Phe Pro Asn Ala Pro Ile Tyr Asn Asp Arg Glu Arg Leu Gln
                210                 215                 220

Ile Tyr Leu Ser Asp Ala Gly Ile Leu Ala Val Cys Phe Gly Leu Tyr
225                 230                 235                 240

Arg Tyr Ala Ala Ala Gln Gly Met Ala Ser Met Ile Cys Leu Tyr Gly
                245                 250                 255

Val Pro Leu Leu Ile Val Asn Ala Phe Leu Val Leu Ile Thr Tyr Leu
                260                 265                 270

Gln His Thr His Pro Ser Leu Pro His Tyr Asp Ser Ser Glu Trp Asp
                275                 280                 285

Trp Leu Arg Gly Ala Leu Ala Thr Val Asp Arg Asp Tyr Gly Ile Leu
                290                 295                 300
```

```
Asn Lys Val Phe His Asn Ile Thr Asp Thr His Val Ala His His Leu
305                 310                 315                 320

Phe Ser Thr Met Pro His Tyr Asn Ala Met Glu Ala Thr Lys Ala Ile
                325                 330                 335

Lys Pro Ile Leu Gly Asp Tyr Tyr Gln Phe Asp Gly Thr Pro Trp Tyr
                340                 345                 350

Val Ala Met Tyr Arg Glu Ala Lys Glu Cys Ile Tyr Val Glu Pro Asp
                355                 360                 365

Arg Glu Gly Asp Lys Lys Gly Val Tyr Trp Tyr Asn Asn Lys Leu
370                 375                 380
```

(2) INFORMATION FOR SEQ ID NO:10:

(i) SEQUENCE CHARACTERISTICS:
        (A) LENGTH: 384 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Brassica juncea (xi) SEQUENCE DESCRIPTION: SEQ ID NO:10:

```
Met Gly Ala Gly Gly Arg Met Gln Val Ser Pro Ser Pro Lys Lys Ser
1               5                   10                  15

Glu Thr Asp Thr Leu Lys Arg Val Pro Cys Glu Thr Pro Pro Phe Thr
                20                  25                  30

Val Gly Glu Leu Lys Lys Ala Ile Pro Pro His Cys Phe Lys Arg Ser
            35                  40                  45

Ile Pro Arg Ser Phe Ser Tyr Leu Ile Trp Asp Ile Ile Val Ala Ser
50                  55                  60

Cys Phe Tyr Tyr Val Ala Thr Thr Tyr Phe Pro Leu Leu Pro His Pro
65                  70                  75                  80

Leu Ser Tyr Val Ala Trp Pro Leu Tyr Trp Ala Cys Gln Gly Val Val
                85                  90                  95

Leu Thr Gly Val Trp Val Ile Ala His Glu Cys Gly His His Ala Phe
                100                 105                 110

Ser Asp Tyr Gln Trp Leu Asp Asp Thr Val Gly Leu Ile Phe His Ser
            115                 120                 125

Phe Leu Leu Val Pro Tyr Phe Ser Trp Lys Tyr Ser His Arg Arg His
130                 135                 140

His Ser Asn Thr Gly Ser Leu Glu Arg Asp Glu Val Phe Val Pro Lys
145                 150                 155                 160

Lys Lys Ser Asp Ile Lys Trp Tyr Gly Lys Tyr Leu Asn Asn Pro Leu
                165                 170                 175

Gly Arg Thr Val Met Leu Thr Val Gln Phe Thr Leu Gly Trp Pro Leu
                180                 185                 190

Tyr Trp Ala Phe Asn Val Ser Gly Arg Pro Tyr Pro Glu Gly Phe Ala
            195                 200                 205

Cys His Phe His Pro Asn Ala Pro Ile Tyr Asn Asp Arg Glu Arg Leu
210                 215                 220

Gln Ile Tyr Val Ser Asp Ala Gly Ile Leu Ala Val Cys Tyr Gly Leu
225                 230                 235                 240

Tyr Arg Tyr Ala Ala Ala Gln Gly Val Ala Ser Met Val Cys Leu Tyr
                245                 250                 255
```

-continued

Gly Val Pro Leu Leu Ile Val Asn Ala Phe Leu Val Leu Ile Thr Tyr
            260                 265                 270

Leu Gln His Thr His Pro Ser Leu Pro His Tyr Asp Ser Ser Glu Trp
            275                 280                 285

Asp Trp Leu Arg Gly Ala Leu Ala Thr Val Asp Arg Asp Tyr Gly Ile
            290                 295                 300

Leu Asn Lys Val Phe His Asn Ile Thr Asp Thr His Val Ala His His
305                 310                 315                 320

Leu Phe Ser Thr Met Pro His Tyr His Ala Met Glu Val Thr Lys Ala
            325                 330                 335

Ile Lys Pro Ile Leu Gly Asp Tyr Tyr Gln Phe Asp Gly Thr Pro Trp
            340                 345                 350

Val Lys Ala Met Trp Arg Glu Ala Lys Glu Cys Ile Tyr Val Glu Pro
            355                 360                 365

Asp Arg Gln Gly Glu Lys Lys Gly Val Phe Trp Tyr Asn Asn Lys Leu
            370                 375                 380

(2) INFORMATION FOR SEQ ID NO:11:

(i) SEQUENCE CHARACTERISTICS:
        (A) LENGTH: 383 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Glycine max (xi) SEQUENCE DESCRIPTION: SEQ ID NO:11:

Met Gly Ala Gly Gly Arg Thr Asp Val Pro Pro Ala Asn Arg Lys Ser
1               5                   10                  15

Glu Val Asp Pro Leu Lys Arg Val Pro Phe Glu Lys Pro Gln Phe Ser
            20                  25                  30

Leu Ser Gln Ile Lys Lys Ala Ile Pro Pro His Cys Phe Gln Arg Ser
            35                  40                  45

Val Leu Arg Ser Phe Ser Tyr Val Val Tyr Asp Leu Thr Ile Ala Phe
50                  55                  60

Cys Leu Tyr Tyr Val Ala Thr His Tyr Phe His Leu Leu Pro Gly Pro
65                  70                  75                  80

Leu Ser Phe Arg Gly Met Ala Ile Tyr Trp Ala Val Gln Gly Cys Ile
            85                  90                  95

Leu Thr Gly Val Trp Val Ile Ala His Glu Cys Gly His His Ala Phe
            100                 105                 110

Ser Asp Tyr Gln Leu Leu Asp Asp Ile Val Gly Leu Ile Leu His Ser
            115                 120                 125

Ala Leu Leu Val Pro Tyr Phe Ser Trp Lys Tyr Ser His Arg Arg His
            130                 135                 140

His Ser Asn Thr Gly Ser Leu Glu Arg Asp Glu Val Phe Val Pro Lys
145                 150                 155                 160

Gln Lys Ser Cys Ile Lys Trp Tyr Ser Lys Tyr Leu Asn Asn Pro Pro
            165                 170                 175

Gly Arg Val Leu Thr Leu Ala Val Thr Leu Thr Leu Gly Trp Pro Leu
            180                 185                 190

Tyr Leu Ala Leu Asn Val Ser Gly Arg Pro Tyr Asp Arg Phe Ala Cys
            195                 200                 205

```
His Tyr Asp Pro Tyr Gly Pro Ile Tyr Ser Asp Arg Glu Arg Leu Gln
    210                 215                 220

Ile Tyr Ile Ser Asp Ala Gly Val Leu Ala Val Val Tyr Gly Leu Phe
225                 230                 235                 240

Arg Leu Ala Met Ala Lys Gly Leu Ala Trp Val Val Cys Val Tyr Gly
                245                 250                 255

Val Pro Leu Leu Val Val Asn Gly Phe Leu Val Leu Ile Thr Phe Leu
                260                 265                 270

Gln His Thr His Pro Ala Leu Pro His Tyr Thr Ser Ser Glu Trp Asp
                275                 280                 285

Trp Leu Arg Gly Ala Leu Ala Thr Val Asp Arg Asp Tyr Gly Ile Leu
290                 295                 300

Asn Lys Val Phe His Asn Ile Thr Asp Thr His Val Ala His His Leu
305                 310                 315                 320

Phe Ser Thr Met Pro His Tyr His Ala Met Glu Ala Thr Lys Ala Ile
                325                 330                 335

Lys Pro Ile Leu Gly Glu Tyr Tyr Arg Phe Asp Glu Thr Pro Phe Val
                340                 345                 350

Lys Ala Met Trp Arg Glu Ala Arg Glu Cys Ile Tyr Val Glu Pro Asp
                355                 360                 365

Gln Ser Thr Glu Ser Lys Gly Val Phe Trp Tyr Asn Asn Lys Leu
                370                 375                 380

(2) INFORMATION FOR SEQ ID NO:12:

(i) SEQUENCE CHARACTERISTICS:
        (A) LENGTH: 383 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Solanum commersonii (xi) SEQUENCE DESCRIPTION: SEQ ID NO:12:

Met Gly Ala Gly Gly Arg Met Ser Ala Pro Asn Gly Glu Thr Glu Val
1               5                   10                  15

Lys Arg Asn Pro Leu Gln Lys Val Pro Thr Ser Lys Pro Pro Phe Thr
                20                  25                  30

Val Gly Asp Ile Lys Lys Ala Ile Pro Pro His Cys Phe Gln Arg Ser
                35                  40                  45

Leu Ile Arg Ser Phe Ser Tyr Val Val Tyr Asp Leu Ile Leu Val Ser
50                  55                  60

Ile Met Tyr Tyr Val Ala Asn Thr Tyr Phe His Leu Leu Pro Ser Pro
65                  70                  75                  80

Tyr Cys Tyr Ile Ala Trp Pro Ile Tyr Trp Ile Cys Gln Gly Cys Val
                85                  90                  95

Cys Thr Gly Ile Trp Val Asn Ala His Glu Cys Gly His His Ala Phe
                100                 105                 110

Ser Asp Tyr Gln Trp Val Asp Asp Thr Val Gly Leu Ile Leu His Ser
                115                 120                 125

Ala Leu Leu Val Pro Tyr Phe Ser Trp Lys Tyr Ser His Arg Arg His
                130                 135                 140

His Ser Asn Thr Gly Ser Leu Glu Arg Asp Glu Val Phe Val Pro Lys
145                 150                 155                 160
```

```
Pro Lys Ser Gln Leu Gly Trp Tyr Ser Lys Tyr Leu Asn Asn Pro Pro
            165                 170                 175

Gly Arg Val Leu Ser Leu Thr Ile Thr Leu Thr Leu Gly Trp Pro Leu
            180                 185                 190

Tyr Leu Ala Phe Asn Val Ser Gly Arg Pro Tyr Asp Arg Phe Ala Cys
            195                 200                 205

His Tyr Asp Pro Tyr Gly Pro Ile Tyr Asn Asn Arg Glu Arg Leu Gln
            210                 215                 220

Ile Phe Ile Ser Asp Ala Gly Val Leu Gly Val Cys Tyr Leu Leu Tyr
225                 230                 235                 240

Arg Ile Ala Leu Val Lys Gly Leu Ala Trp Leu Val Cys Val Tyr Gly
            245                 250                 255

Val Pro Leu Leu Val Val Asn Gly Phe Leu Val Leu Ile Thr Tyr Leu
            260                 265                 270

Gln His Thr His Pro Ser Leu Pro His Tyr Asp Ser Thr Glu Trp Asp
            275                 280                 285

Trp Leu Arg Gly Ala Leu Ala Thr Cys Asp Arg Asp Tyr Gly Val Leu
            290                 295                 300

Asn Lys Val Phe His Asn Ile Thr Asp Thr His Val Val His His Leu
305                 310                 315                 320

Phe Ser Thr Met Pro His Tyr Asn Ala Met Glu Ala Thr Lys Ala Val
            325                 330                 335

Lys Pro Leu Leu Gly Asp Tyr Tyr Gln Phe Asp Gly Thr Pro Ile Tyr
            340                 345                 350

Lys Glu Met Trp Arg Glu Ala Lys Glu Cys Leu Tyr Val Glu Lys Asp
            355                 360                 365

Glu Ser Ser Gln Gly Lys Gly Val Phe Trp Tyr Lys Asn Lys Leu
            370                 375                 380

(2) INFORMATION FOR SEQ ID NO:13:

(i) SEQUENCE CHARACTERISTICS:
        (A) LENGTH: 387 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: GLycine max (xi) SEQUENCE DESCRIPTION: SEQ ID NO:13:

Met Gly Leu Ala Lys Glu Thr Thr Met Gly Gly Arg Gly Arg Val Ala
1               5                   10                  15

Lys Val Glu Val Gln Gly Lys Lys Pro Leu Ser Arg Val Pro Asn Thr
            20                  25                  30

Lys Pro Pro Phe Thr Val Gly Gln Leu Lys Lys Ala Ile Pro Pro His
            35                  40                  45

Cys Phe Gln Arg Ser Leu Leu Thr Ser Phe Ser Tyr Val Val Tyr Asp
            50                  55                  60

Leu Ser Phe Ala Phe Ile Phe Tyr Ile Ala Thr Thr Tyr Phe His Leu
65                  70                  75                  80

Leu Pro Gln Pro Phe Ser Leu Ile Ala Trp Pro Ile Tyr Trp Val Leu
            85                  90                  95

Gln Gly Cys Leu Leu Thr Gly Val Trp Val Ile Ala His Glu Cys Gly
            100                 105                 110
```

```
His His Ala Phe Ser Lys Tyr Gln Trp Val Asp Asp Val Val Gly Leu
        115                 120                 125

Thr Leu His Ser Thr Leu Leu Val Pro Tyr Phe Ser Trp Lys Ile Ser
        130                 135                 140

His Arg Arg His His Ser Asn Thr Gly Ser Leu Asp Arg Asp Glu Val
145                 150                 155                 160

Phe Val Pro Lys Pro Lys Ser Lys Val Ala Trp Phe Ser Lys Tyr Leu
                165                 170                 175

Asn Asn Pro Leu Gly Arg Ala Val Ser Leu Leu Val Thr Leu Thr Ile
            180                 185                 190

Gly Trp Pro Met Tyr Leu Ala Phe Asn Val Ser Gly Arg Pro Tyr Asp
        195                 200                 205

Ser Phe Ala Ser His Tyr His Pro Tyr Ala Pro Ile Tyr Ser Asn Arg
210                 215                 220

Glu Arg Leu Leu Ile Tyr Val Ser Asp Val Ala Leu Phe Ser Val Thr
225                 230                 235                 240

Tyr Ser Leu Tyr Arg Val Ala Thr Leu Lys Gly Leu Val Trp Leu Leu
                245                 250                 255

Cys Val Tyr Gly Val Pro Leu Leu Ile Val Asn Gly Phe Leu Val Thr
            260                 265                 270

Ile Thr Tyr Leu Gln His Thr His Phe Ala Leu Pro His Tyr Asp Ser
        275                 280                 285

Ser Glu Trp Asp Trp Leu Lys Gly Ala Leu Ala Thr Met Asp Arg Asp
        290                 295                 300

Tyr Gly Ile Leu Asn Lys Val Phe His His Ile Thr Asp Thr His Val
305                 310                 315                 320

Ala His His Leu Phe Ser Thr Met Pro His Tyr His Ala Met Glu Ala
                325                 330                 335

Thr Asn Ala Ile Lys Pro Ile Leu Gly Glu Tyr Tyr Gln Phe Asp Asp
            340                 345                 350

Thr Pro Phe Tyr Lys Ala Leu Trp Arg Glu Ala Arg Glu Cys Leu Tyr
        355                 360                 365

Val Glu Pro Asp Glu Gly Thr Ser Glu Lys Gly Val Tyr Trp Tyr Arg
370                 375                 380

Asn Lys Tyr
385

(2) INFORMATION FOR SEQ ID NO:14:

(i) SEQUENCE CHARACTERISTICS:
        (A) LENGTH: 387 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Ricinus communis (xi) SEQUENCE DESCRIPTION: SEQ ID NO:14:

Met Gly Gly Gly Arg Met Ser Thr Val Ile Thr Ser Asn Asn Ser
1               5                   10                  15

Glu Lys Lys Gly Gly Ser Ser His Leu Lys Arg Ala Pro His Thr Lys
                20                  25                  30

Pro Pro Phe Thr Leu Gly Asp Leu Lys Arg Ala Ile Pro Pro His Cys
            35                  40                  45
```

```
Phe Glu Arg Ser Phe Val Arg Ser Phe Ser Tyr Val Ala Tyr Asp Val
    50                  55                  60
Cys Leu Ser Phe Leu Phe Tyr Ser Ile Ala Thr Asn Phe Phe Pro Tyr
65                  70                  75                  80
Ile Ser Ser Pro Leu Ser Tyr Val Ala Trp Leu Val Tyr Trp Leu Phe
                85                  90                  95
Gln Gly Cys Ile Leu Thr Gly Leu Trp Val Ile Gly His Glu Cys Gly
            100                 105                 110
His His Ala Phe Ser Glu Tyr Gln Leu Ala Asp Asp Ile Val Gly Leu
        115                 120                 125
Ile Val His Ser Ala Leu Leu Val Pro Tyr Phe Ser Trp Lys Tyr Ser
    130                 135                 140
His Arg Arg His His Ser Asn Ile Gly Ser Leu Glu Arg Asp Glu Val
145                 150                 155                 160
Phe Val Pro Lys Ser Lys Ser Lys Ile Ser Trp Tyr Ser Lys Tyr Ser
                165                 170                 175
Asn Asn Pro Pro Gly Arg Val Leu Thr Leu Ala Ala Thr Leu Leu Leu
            180                 185                 190
Gly Trp Pro Leu Tyr Leu Ala Phe Asn Val Ser Gly Arg Pro Tyr Asp
        195                 200                 205
Arg Phe Ala Cys His Tyr Asp Pro Tyr Gly Pro Ile Phe Ser Glu Arg
    210                 215                 220
Glu Arg Leu Gln Ile Tyr Ile Ala Asp Leu Gly Ile Phe Ala Thr Thr
225                 230                 235                 240
Phe Val Leu Tyr Gln Ala Thr Met Ala Lys Gly Leu Ala Trp Val Met
                245                 250                 255
Arg Ile Tyr Gly Val Pro Leu Leu Ile Val Asn Cys Phe Leu Val Met
            260                 265                 270
Ile Thr Tyr Leu Gln His Thr His Pro Ala Ile Pro Arg Tyr Gly Ser
        275                 280                 285
Ser Glu Trp Asp Trp Leu Arg Gly Ala Met Val Thr Val Asp Arg Asp
    290                 295                 300
Tyr Gly Val Leu Asn Lys Val Phe His Asn Ile Ala Asp Thr His Val
305                 310                 315                 320
Ala His His Leu Phe Ala Thr Val Pro His Tyr His Ala Met Glu Ala
                325                 330                 335
Thr Lys Ala Ile Lys Pro Ile Met Gly Glu Tyr Tyr Arg Tyr Asp Gly
            340                 345                 350
Thr Pro Phe Tyr Lys Ala Leu Trp Arg Glu Ala Lys Glu Cys Leu Phe
        355                 360                 365
Val Glu Pro Asp Glu Gly Ala Pro Thr Gln Gly Val Phe Trp Tyr Arg
    370                 375                 380
Asn Lys Tyr
385

(2) INFORMATION FOR SEQ ID NO:15:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (v) FRAGMENT TYPE: internal
```

(xi) SEQUENCE DESCRIPTION: SEQ ID NO:15:

His Glu Cys Gly His His
1               5

(2) INFORMATION FOR SEQ ID NO:16:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (v) FRAGMENT TYPE: internal (xi) SEQUENCE DESCRIPTION: SEQ ID NO:16:

His Arg Asn His His
1               5

(2) INFORMATION FOR SEQ ID NO:17:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (v) FRAGMENT TYPE: internal (xi) SEQUENCE DESCRIPTION: SEQ ID NO:17:

His Val Met His His
1               5

(2) INFORMATION FOR SEQ ID NO:18:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:18:

TGGAATTCCY TBMGNNNNYT SGGNHTBGG                                               29

(2) INFORMATION FOR SEQ ID NO:19:

(i) SEQUENCE CHARACTERISTICS:
            (A) LENGTH: 1610 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Euphorbia lagascae (ix) FEATURE:
            (A) NAME/KEY: CDS
            (B) LOCATION: 8..1546

(xi) SEQUENCE DESCRIPTION: SEQ ID NO:19:

AGTAACA ATG AAC ACT AAG GAG AAG AAG AAG AAC AGG GTT TCT AAC                    49
        Met Asn Thr Lys Glu Lys Lys Lys Asn Arg Val Ser Asn
         1               5                  10

```
ATG TCT ATT CTT CTT TGC TTC CTT TGC CTT CTT CCA GTT TTC CTT GTT      97
Met Ser Ile Leu Leu Cys Phe Leu Cys Leu Leu Pro Val Phe Leu Val
 15              20              25              30

TCT CTT TCT ATT CTT TCT AAG AGG CTT AAG CCA TCT AAG TGG AAG CTT     145
Ser Leu Ser Ile Leu Ser Lys Arg Leu Lys Pro Ser Lys Trp Lys Leu
             35              40              45

CCA CCA GGA CCA AAG ACT CTT CCA ATT ATT GGA AAC CTT CAA GAT GAG     193
Pro Pro Gly Pro Lys Thr Leu Pro Ile Ile Gly Asn Leu Gln Asp Glu
             50              55              60

AGG CAA GAT CCA GAG GCT TCT CTT TCT CAA GGA CAT ATT GCT AGG GGA     241
Arg Gln Asp Pro Glu Ala Ser Leu Ser Gln Gly His Ile Ala Arg Gly
             65              70              75

CCA GTT GTT CAT TGC GAG AAG CTT GAG TCT TTC GGA ACT CAA CCA ACT     289
Pro Val Val His Cys Glu Lys Leu Glu Ser Phe Gly Thr Gln Pro Thr
 80              85              90

ATT AAG GTT GGA CAT TAT GAT AAG AAC TGC GCT CTT CTT CAT GGA GCT     337
Ile Lys Val Gly His Tyr Asp Lys Asn Cys Ala Leu Leu His Gly Ala
 95             100             105             110

GGA GAT GAG CTT CTT GGA AAG CCA TCT CCA CCA AAC GAT GCT TGG GAT     385
Gly Asp Glu Leu Leu Gly Lys Pro Ser Pro Pro Asn Asp Ala Trp Asp
             115             120             125

ACT GGA GGA TAT GGA CTT GAG AGG TCT AAG AAC GAG AGG TGG AAG GAG     433
Thr Gly Gly Tyr Gly Leu Glu Arg Ser Lys Asn Glu Arg Trp Lys Glu
             130             135             140

AAG GAG ACT TGG TCT GCT TTC AGG CAA TAT AGG ACT CTT AGG GCT TTC     481
Lys Glu Thr Trp Ser Ala Phe Arg Gln Tyr Arg Thr Leu Arg Ala Phe
             145             150             155

GGA ATG GGA GGA AGG TCT TTC GAG CTT ATG AGG TGG CAA GAG GCT CAT     529
Gly Met Gly Gly Arg Ser Phe Glu Leu Met Arg Trp Gln Glu Ala His
 160             165             170

TGC CTT GTT GAT GGA TAT GTT TCT AGG AAG GCT TCT GGA ACT GAT CCA     577
Cys Leu Val Asp Gly Tyr Val Ser Arg Lys Ala Ser Gly Thr Asp Pro
175             180             185             190

ACT AAG GAT CTT GAG GAT TCT AGG TTC AAC ATT ATT ATG GGA GCT ACT     625
Thr Lys Asp Leu Glu Asp Ser Arg Phe Asn Ile Ile Met Gly Ala Thr
             195             200             205

TTC AAC CAA GGA CTT GAT TAT AAG ATT AAG ACT TTC CTT GAT AGG CAT     673
Phe Asn Gln Gly Leu Asp Tyr Lys Ile Lys Thr Phe Leu Asp Arg His
             210             215             220

GAG AGG AGG AAC TTC CAA TTC AAC AAC GTT GAT GCT GTT TAT CAT CAA     721
Glu Arg Arg Asn Phe Gln Phe Asn Asn Val Asp Ala Val Tyr His Gln
             225             230             235

ATG AAG GAT GCT GAG AGG GGA TTC GTT GAT TCT AGG GGA TGG CAA GAT     769
Met Lys Asp Ala Glu Arg Gly Phe Val Asp Ser Arg Gly Trp Gln Asp
240             245             250

GAG TTC GGA ATT GCT CTT CAA CAA GTT GTT GCT CAA ATT CTT GAT AAG     817
Glu Phe Gly Ile Ala Leu Gln Gln Val Val Ala Gln Ile Leu Asp Lys
255             260             265             270

CCA CTT GAT CAT CAA AAG GCT CTT GAG AGG TGG CAA CCA AGG GAT TCT     865
Pro Leu Asp His Gln Lys Ala Leu Glu Arg Trp Gln Pro Arg Asp Ser
             275             280             285

CTT AAC CAT TTC ATT GGA GCT AGG GAT GAT GAG ATG GTT CAA ATT AAG     913
Leu Asn His Phe Ile Gly Ala Arg Asp Asp Glu Met Val Gln Ile Lys
             290             295             300

TAT GAT TTC TGC AAG GAT GCT CTT AGG ATG TTC GAT ACT GGA ATT CTT     961
Tyr Asp Phe Cys Lys Asp Ala Leu Arg Met Phe Asp Thr Gly Ile Leu
             305             310             315

GCT GCT GAT CTT CAA TCT TCT ACT TCT TCT ATT AGG TGG GAG CCA ATT    1009
Ala Ala Asp Leu Gln Ser Ser Thr Ser Ser Ile Arg Trp Glu Pro Ile
```

```
          320                 325                 330
GTT GTT ATG CTT CAA GCT GAG GTT AAG GGA GAG ATT TGC GAG GAG CTT      1057
Val Val Met Leu Gln Ala Glu Val Lys Gly Glu Ile Cys Glu Glu Leu
335                 340                 345                 350

GAT AGG GTT ATT GCT AGG CAT CAA AGG CCA TCT ATG AAG GAT AAG ATG      1105
Asp Arg Val Ile Ala Arg His Gln Arg Pro Ser Met Lys Asp Lys Met
                355                 360                 365

GTT AAG AGG TAT ACT GCT GCT GTT GTT TGC GAG CTT GAT AGG TAT GCT      1153
Val Lys Arg Tyr Thr Ala Ala Val Val Cys Glu Leu Asp Arg Tyr Ala
            370                 375                 380

AAG CTT CTT CCA TCT TCT CTT AGG TGC GTT GCT GCT GAT GAG TGG AAG      1201
Lys Leu Leu Pro Ser Ser Leu Arg Cys Val Ala Ala Asp Glu Trp Lys
        385                 390                 395

TTC AGG GAG TAT CTT ATT CCA GTT GGA ATG ACT GTT GGA AAC CTT AAG      1249
Phe Arg Glu Tyr Leu Ile Pro Val Gly Met Thr Val Gly Asn Leu Lys
    400                 405                 410

ACT ACT GTT ATG CTT GAT CAA AAG GAT CCA GTT GAT CCA GAG CTT TTC      1297
Thr Thr Val Met Leu Asp Gln Lys Asp Pro Val Asp Pro Glu Leu Phe
415                 420                 425                 430

GAT GGA ATG TAT GGA CTT GAT GCT GAG GTT CAT TTC GAT AAG ACT GAT      1345
Asp Gly Met Tyr Gly Leu Asp Ala Glu Val His Phe Asp Lys Thr Asp
                435                 440                 445

AGG TTC ATG CCA CCA TTC TCT GCT GGG AGG ATT GCC TGC GCT GGA CAA      1393
Arg Phe Met Pro Pro Phe Ser Ala Gly Arg Ile Ala Cys Ala Gly Gln
            450                 455                 460

CTT CTT GCT GCT TAT GAG CTT TTC CTT TTC TTC TGG ACT ATT GCT GAT      1441
Leu Leu Ala Ala Tyr Glu Leu Phe Leu Phe Phe Trp Thr Ile Ala Asp
        465                 470                 475

GTT TTC CAA ATT TTC TCT CTT GCT CAA TTC AAG GAG GGA CAT TGC ACT      1489
Val Phe Gln Ile Phe Ser Leu Ala Gln Phe Lys Glu Gly His Cys Thr
    480                 485                 490

GCT GTT ACT CTT ATT ATT GAT TGC CTT GCT GTT AGG TAT GAT CTT TGC      1537
Ala Val Thr Leu Ile Ile Asp Cys Leu Ala Val Arg Tyr Asp Leu Cys
495                 500                 505                 510

CTT GCT AGG TAGGGACCTT TACCGTTTGT GTGACCGTGT CAATGCTTGC              1586
Leu Ala Arg

AATGGGCTTT TAATAATATT ATTA                                           1610

(2) INFORMATION FOR SEQ ID NO:20:

(i) SEQUENCE CHARACTERISTICS:
        (A) LENGTH: 1698 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: CDS
        (B) LOCATION: 8..1504

(xi) SEQUENCE DESCRIPTION: SEQ ID NO:20:

GAGAACA ATG GCA CAA TTC GGC ACG AGG GAA ATT CTA GTC TCA CTC TTT      49
        Met Ala Gln Phe Gly Thr Arg Glu Ile Leu Val Ser Leu Phe
        1               5                   10

CTC TTT CTA ATA CTA ATA AAG TTC ACA TTT TTA AAA CTC AAA ACC CCC      97
Leu Phe Leu Ile Leu Ile Lys Phe Thr Phe Leu Lys Leu Lys Thr Pro
15                  20                  25                  30

CAA AAC CTC CCC CCA TCA CCA CCA TCT TTT CCA ATC ACC GGC CAT CTC      145
Gln Asn Leu Pro Pro Ser Pro Pro Ser Phe Pro Ile Thr Gly His Leu
                35                  40                  45
```

-continued

| | | |
|---|---|---|
| CAT CTC CTA AAA CAA CCA ATC CAC AGA ACT CTC CAC CAA ATC GCC ACC<br>His Leu Leu Lys Gln Pro Ile His Arg Thr Leu His Gln Ile Ala Thr<br>  50            55              60 | | 193 |
| AAG TAC GGG GAC ATC TTA TTC CTC CGA TTC GGA ACA CGA AAA GTC CTA<br>Lys Tyr Gly Asp Ile Leu Phe Leu Arg Phe Gly Thr Arg Lys Val Leu<br>      65              70              75 | | 241 |
| GTC ATC TCC TCT CTC CCC GCC GTA CAA GAA TGT TTC ACT ATA AAC GAC<br>Val Ile Ser Ser Leu Pro Ala Val Gln Glu Cys Phe Thr Ile Asn Asp<br>        80              85              90 | | 289 |
| ATC ATT TTC GCT AAC CGC CCA ACA ATT CTC GCC GGG AAG CAC CTC AAT<br>Ile Ile Phe Ala Asn Arg Pro Thr Ile Leu Ala Gly Lys His Leu Asn<br>95              100              105              110 | | 337 |
| TAC AAT TCC ACC ACC ATG GGA TTC GCC TCC TAT GGC GAT CAC TGG CGT<br>Tyr Asn Ser Thr Thr Met Gly Phe Ala Ser Tyr Gly Asp His Trp Arg<br>              115              120              125 | | 385 |
| CAT CTC CGA CGA CTC ACA ACA ATT GAG CTC TTC TCT GCA AAT CGT GTT<br>His Leu Arg Arg Leu Thr Thr Ile Glu Leu Phe Ser Ala Asn Arg Val<br>            130              135              140 | | 433 |
| GCC ATG TTT TCC GGG TTC CGG GCC GAT GAA AGT ACA GCT TTT TAT CAA<br>Ala Met Phe Ser Gly Phe Arg Ala Asp Glu Ser Thr Ala Phe Tyr Gln<br>          145              150              155 | | 481 |
| ACA GTT GTT CCA GGA AAT CGG GAT TCG GGA AAG ATA GTA ACT TTG ACA<br>Thr Val Val Pro Gly Asn Arg Asp Ser Gly Lys Ile Val Thr Leu Thr<br>    160              165              170 | | 529 |
| TCG AAA CTG ATG GAG CTT ACA CTG AAT AAC ATA ATG AGA ATG GCT GCC<br>Ser Lys Leu Met Glu Leu Thr Leu Asn Asn Ile Met Arg Met Ala Ala<br>175              180              185              190 | | 577 |
| GGA AAA CGG TTT TAC GGG AAA GAA GTG AAG GAT GAA GAA GGT GAG TTG<br>Gly Lys Arg Phe Tyr Gly Lys Glu Val Lys Asp Glu Glu Gly Glu Leu<br>              195              200              205 | | 625 |
| TTG CAG GAT CTT ATG AAG AAA ATG GAG GCG CTC CGG GGG AAT TCA ACG<br>Leu Gln Asp Leu Met Lys Lys Met Glu Ala Leu Arg Gly Asn Ser Thr<br>            210              215              220 | | 673 |
| GTG AAA CGA GAT TAT TTT CCA GTA TTG CAG TGG ATT GAT TAT CAG GGA<br>Val Lys Arg Asp Tyr Phe Pro Val Leu Gln Trp Ile Asp Tyr Gln Gly<br>          225              230              235 | | 721 |
| GTA AAG AAG AAG ATG AGG AAC CTG ATG AAG AAA ATG GAC GGG TTC TTG<br>Val Lys Lys Lys Met Arg Asn Leu Met Lys Lys Met Asp Gly Phe Leu<br>    240              245              250 | | 769 |
| CAA AAT CTC ATT GAT GAA CAC CGA AAC ACG ACG TTG TGG ATC AAT CAA<br>Gln Asn Leu Ile Asp Glu His Arg Asn Thr Thr Leu Trp Ile Asn Gln<br>255              260              265              270 | | 817 |
| GTT CGA GCA ACT CGG ACA AAA AGA GGA ACT TGG ACA CTG GTA GAT GTT<br>Val Arg Ala Thr Arg Thr Lys Arg Gly Thr Trp Thr Leu Val Asp Val<br>              275              280              285 | | 865 |
| ATG TTG AAT CTT AAA AAG ACA CAA CCT GAC TTC TAC ACT GAT CTA ACT<br>Met Leu Asn Leu Lys Lys Thr Gln Pro Asp Phe Tyr Thr Asp Leu Thr<br>            290              295              300 | | 913 |
| ATC AAA GGT GTC ATT CAG ACA ACA CTG ACT GCA GGA TCT CAA ACG TCA<br>Ile Lys Gly Val Ile Gln Thr Thr Leu Thr Ala Gly Ser Gln Thr Ser<br>          305              310              315 | | 961 |
| GCA GTT ACA CTA GAA TGG GCG CTG TCA CTT CTT CTC AAC CAT CCT CAA<br>Ala Val Thr Leu Glu Trp Ala Leu Ser Leu Leu Leu Asn His Pro Gln<br>    320              325              330 | | 1009 |
| GTA ATG CAC AAA GCT TAT GCC GAA ATA GAG GCG ATT GTC GGG ACC AAC<br>Val Met His Lys Ala Tyr Ala Glu Ile Glu Ala Ile Val Gly Thr Asn<br>335              340              345              350 | | 1057 |
| CGC TTA TTA AAC GAA GCC GAC TTA CCA CAT CTA AGC TAT TTA CAA AAC<br>Arg Leu Leu Asn Glu Ala Asp Leu Pro His Leu Ser Tyr Leu Gln Asn | | 1105 |

-continued

```
                      355                 360                 365
ATA ATC ACC GAG ACA TTT CGA CTC TTC CCA CCA GTA CCA CTT TTA CTA   1153
Ile Ile Thr Glu Thr Phe Arg Leu Phe Pro Pro Val Pro Leu Leu Leu
            370                 375                 380

CCC CAT AAA TCA TCA GCA GAT TGC ATA GTT TCC GGG TTT CAC ATA CCA   1201
Pro His Lys Ser Ser Ala Asp Cys Ile Val Ser Gly Phe His Ile Pro
            385                 390                 395

CGG GGC ACA ATG TTG CTA GTG AAC ACA TGG AGC ATG AAT AGA AAT CCA   1249
Arg Gly Thr Met Leu Leu Val Asn Thr Trp Ser Met Asn Arg Asn Pro
        400                 405                 410

AGA TTA TGG AAG GAA CCA GAG AAA TTC ATA CCA GAA AGA TTT GAA GGA   1297
Arg Leu Trp Lys Glu Pro Glu Lys Phe Ile Pro Glu Arg Phe Glu Gly
415                 420                 425                 430

GGA GAA AAT ACT GAA GGG TGT AAC TAT AAA TTG CTT CCT TTC GGT GCA   1345
Gly Glu Asn Thr Glu Gly Cys Asn Tyr Lys Leu Leu Pro Phe Gly Ala
                435                 440                 445

GGA AGG CGG GCT TGT CCG GGG GCC GGT GTG GCG AAA CGA ATG GTA GGA   1393
Gly Arg Arg Ala Cys Pro Gly Ala Gly Val Ala Lys Arg Met Val Gly
                450                 455                 460

CTC ACT TTA GGT GCA TTG ATT CAG TGT TTT GAG TGG GAA AGA ATT GGG   1441
Leu Thr Leu Gly Ala Leu Ile Gln Cys Phe Glu Trp Glu Arg Ile Gly
            465                 470                 475

GAA GAA GAA ATA GAT TTG AGT GAA GGA ACA GGT CTT ACT ATG CCA AAA   1489
Glu Glu Glu Ile Asp Leu Ser Glu Gly Thr Gly Leu Thr Met Pro Lys
        480                 485                 490

GAT TTC CTT TGG AAG TAATATGCAA ACCTCGGCAA AACATGATTA ACTTTCTTTC   1544
Asp Phe Leu Trp Lys
495

TACATTGTTA TAAAAGGTGG GTTTCTTTGC AGGTGCCAAC CCTAATTCAA ATATCGCATT   1604

TTTTCCCTGC AACCCAGCTG CTAACCAAAT ATCACTGTTT CTCATTATTC CTTATATAAA   1664

ACCTTAAAGC ACTATTTGCC TCCTAAAAAA AAAA                              1698
```

PLANT FATTY ACID EPOXYGENASE GENES AND USES THEREFOR

This application claims prong to provisional applications 60/043,706, filed Apr. 16, 1997 and 60/050,403, filed Jun. 20, 1997.

FIELD OF THE INVENTION

The present invention relates generally to novel genetic sequences which encode fatty acid epoxygenase enzymes. In particular, the present invention relates to genetic sequences which encode fatty acid Δ12-epoxygenase enzymes as defined herein. More particularly, the present invention provides cDNA and genomic gene sequences which encode plant fatty acid epoxygenases, preferably *Crepeis palaestina* or *Euphorbia lagascae* Δ12-epoxygenases. The genetic sequences of the present invention provide the means by which fatty acid metabolism may be altered or manipulated in organisms such as yeasts, moulds, bacteria, insects, birds, mammals and plants, in particular to convert unsaturated fatty acids to epoxygenated fatty acids therein. The invention extends to genetically modified oil-accumulating organisms transformed with the subject genetic sequences and to the oils derived therefrom. The oils thus produced provide the means for the cost-effective raw materials for use in the efficient production of coatings, resins, glues, plastics, surfactants and lubricants, amongst others.

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

Bibliographic details of the publications referred to by author in this specification are collected at the end of the description. Sequence identity numbers (SEQ ID NOs.) for the nucleotide and amino acid sequences referred to in the specification are defined after the bibliography.

BACKGROUND TO THE INVENTION

There is considerable interest world-wide in producing chemical feedstock, such as fatty acids, for industrial use from renewable plant sources rather than from non-renewable petrochemicals. This concept has broad appeal to manufacturers and consumers on the basis of resource conservation and provides a significant opportunity to develop new industrial crops for agriculture.

There is a diverse array of unusual fatty acids in nature and these have been well characterised (Badam & Patil, 1981; Smith, 1970). Many of these unusual fatty acids have industrial potential and this has led to interest in domesticating such species to enable agricultural production of particular fatty acids.

One class of fatty acids of particular interest are the epoxy-fatty acids, consisting of an acyl chain in which two adjacent carbon bonds are linked by an epoxy bridge. Due to their high reactivities, they have considerable application in the production of coatings, resins, glues, plastics, surfactants and lubricants. These fatty acids are currently produced by chemical epoxidation of vegetable oils, mainly soybean oil and linseed oil, however this process produces mixtures of multiple and isomeric forms and involves significant processing costs.

Attempts are being made by others to develop some wild plants that contain epoxy fatty acids (eg. *Euphorbia lagascae, Vernonia galamensis*) into commercial sources of these oils. However, problems with agronomic suitability and low yield potential severely limit the commercial utility of traditional plant breeding and cultivation approaches.

The rapidly increasing sophistication of recombinant DNA technology is greatly facilitating the efficiency of commercially-important industrial processes, by the expression of genes isolated from a first organism or species in a second organism or species to confer novel phenotypes thereon. More particularly, conventional industrial processes can be made more efficient or cost-effective, resulting in greater yields per unit cost by the application of recombinant DNA techniques.

Moreover, the appropriate choice of host organism for the expression of a genetic sequence of interest provides for the production of compounds which are not normally produced or synthesized by the host, at a high yield and purity.

However, despite the general effectiveness of recombinant DNA technology, the isolation of genetic sequences which encode important enzymes in fatty acid metabolism, in particular the genes which encode the fatty acid Δ12-epoxygenase enzymes responsible for producing 12,13-epoxy-9-octadecenoic acid (vemolic acid) and 12,13-epoxy-9,15-octadecadienoic acid, amongst others, remains a major obstacle to the development of genetically-engineered organisms which produce these fatty acids.

Until the present invention, there were only limited biochemical data indicating the nature of fatty acid epoxygenase enzymes, in particular Δ12-epoxygenases. However, in *Euphorbia lagascae*, the formation of 12,13-epoxy-9-octadecenoic acid (vernolic acid) from linoleic acid appears to be catalysed by a cytochrome-P450-dependent Δ12 epoxygenase enzyme (Bafor et al., 1993; Blee et al., 1994). Additionally, developing seed of linseed plants have the capability to convert added vernolic acid to 12,13epoxy-9,15-octadecadienoic acid by an endogenous Δ15 desaturase (Engeseth and Stymne, 1996). Epoxy-fatty acids can also be produced by a peroxide-dependent peroxygenase in plant tissues (Blee and Schuber, 1990).

In viork leading up to the present invention, the inventors sought to isolate genetic sequences which encode genes which are important for the production of epoxy-fatty acids, such as 12,13-epoxy-9-octadecenoic acid (vernolic acid) or 12,13-epoxy-9,15-octadecadienoic acid and to transfer these genetic sequences into highly productive commercial oilseed plants and/or other oil accumulating organisms.

SUMMARY OF THE INVENTION

One aspect of the invention provides an isolated nucleic acid molecule which encodes or is complementary to an isolated nucleic acid molecule which encodes a fatty acid epoxygenase.

A second aspect of the invention provides an isolated nucleic acid molecule which hybridizes under at least low stringency conditions to at least 20 contiguous nucleotides of SEQ ID NOs:1 or 3 or 5 or 19 or 20, or a complementary sequence thereto.

A further aspect of the invention provides isolated nucleic acid molecule which comprises a sequence of nucleotides which is at least 65% identical to SEQ ID NO:1 or 3 or 5 or which is at least 75% identical to at least 200 contiguous nucleotides in SEQ ID NOs: 19 or 20, or a complementary sequence thereto.

A further aspect of the invention provides a genetic construct which comprises the isolated nucleic acid molecule supra, in either the sense or antisense orientation, in operable connection with a promoter sequence.

A further aspect of the invention provides a method of altering the level of epoxy fatty acids in a cell, tissue, organ or organism, said method comprising expressing a sense, antisense, ribozyme or co-suppression molecule comprising the isolated nucleic acid molecule supra in said cell for a time and under conditions sufficient for the level of epoxy fatty acids therein to be increased or reduced.

A further aspect of the invention provides a method of producing a recombinant enzymatically active epoxygenase polypeptide in a cell, said method comprising expressing the isolated nucleic acid molecule supra in said cell for a time and under conditions sufficient for the epoxygenase encoded therefor to be produced.

A further aspect of the invention provides a method of producing a recombinant enzymatically active epoxygenase polypeptide in a cell, said method comprising the steps of:

(i) producing a genetic construct which comprises the isolated nucleic acid molecule supra placed operably under the control of a promoter capable of conferring expression on said genetic sequence in said cell, and optionally an expression enhancer element;

(ii) transforming said genetic construct into said cell; and (iii) selecting transformants which express a functional epoxygenase encoded by the genetic sequence at a high level.

A still further aspect of the invention provides a method of producing a recombinant enzymatically active epoxygenase polypeptide in a transgenic plant comprising the steps of:

(i) producing a genetic construct which comprises the isolated nucleic acid molecule supra placed operably under the control of a seed-specific promoter and optionally an expression enhancer element, wherein said genetic sequences is also placed upstream of a transcription terminator sequence;

(ii) transforming said genetic construct into a cell or tissue of said plant; and (iii) selecting transformants which express a functional epoxygenase encoded by the genetic sequence at a high level in seeds.

A further aspect of the invention provides a recombinant epoxygenase polypeptide or functional enzyme molecule.

A further aspect of the invention provides a recombinant epoxygenase which comprises a sequence of amino acids set forth in any one of SEQ ID NOs: 2 or 4 or 6 or a homologue, analogue or derivative thereof which is at least about 50% identical thereto.

A still further aspect of the invention provides a method of producing an epoxygenated fatty acid in a cell, tissue, organ or organism, said method comprising incubating a cell, tissue, organ or organism which expresses an enzymatically active recombinant epoxygenase with a fatty acid substrate and preferably, an unsaturated fatty acid substrate, for a time and under conditions sufficient for at least one carbon bond, preferably a carbon double bond, of said substrate to be converted to an epoxy group.

A further aspect of the invention provides an immunologically interactive molecule which binds to the recombinant epoxygenase polypeptide described herein or a homologue, analogue or derivative thereof.

BRIEF DESCRIPTION OF THE DRAWINGS

FIGS. 2A–2H are is a schematic representation showing the alignment of the amino acid sequences of the epoxygenase polypeptide of *Crepis palaestrina* (Cpal2; SEQ ID NO:2), a further epoxygenase derived from Crepis sp. other than *C. palaestina* which produces high levels of vernolic acid (CrepX; SEQ ID NO:4), a partial amino acid sequence of an epoxygenase polypeptide derived from *Vernonia galamensis* (Vgal1; SEQ ID NO:6), the amino acid sequence of the Δ12 acetylenase of *Crepis alpina* (Crep1; SEQ ID NO:8), the Δ12 desaturases of *A. thaliana* (L26296; SEQ ID NO:9), *Brassica juncea* (X91139; SEQ ID NO:10), *Glycine max* (L43921; SEQ ID NO:11), *Solanum commersonii* (X92847; SEQ ID NO:12) and *Glycine max* (L43920; SEQ ID NO:13), and the Δ12 hydroxylase of *Ricinus communis* (U22378; SEQ ID NO:14). Underlined are three histidine-rich motifs that are conserved in non-heme containing mixed-function monooxygenases.

FIG. 4 is a schematic representation showing the nucleotide sequence (SEQ ID NO:18) of the degenerate PCR primer (5' to 3' direction) used to isolate the *Euphorbia lagascae* epoxygenase genes described herein.

FIG. 5 is a copy of a photographic representation of a RNA dot blot hybridization showing expression of the epoxygenase gene exemplified in SEQ ID NO:3 in plants which produce vernolic acid compared to plants which do not produce vernolic acid. One μg of total RNA was isolated from the specified tissue and dot blotted onto the Hybond N+ membrane from Amersham as per the manufacturer's instructions. The blot was hybridised at 42° C. in 50% formamide with the relevant $^{32}$P labelled probe made from SEQ ID NO: 3 for 16 hours. Blots were washed twice in 2×SSC (NaCl-Sodium Citrate buffer) at room temperature then in 0.5×SSC at 55° C. for 20 minutes. Autoradiographs were obtained after an overnight exposure. Panel A shows total RNA from developing seed of *Euphorbia lagascae* (1), *Euphorbia cyparissus* (2), *Vernonia galamensis* (3), and flax (*Linum usitatissimum*)(4). Panel B shows total RNA from various tissues of *Euphorbia lagascae*, including developing seed (1), root (2) and leaf (3).

FIG. 7 is a copy of a photographic representation of a RNA dot blot hybridization showing expression of the epoxygenase gene exemplified in SEQ ID NO:20 in plants which produce vernolic acid compared to plants which do not produce vernolic acid. One μg of total RNA was isolated from the specified tissue and dot blotted onto the Hybond N⁺ membrane from Amersham as per the manufacturer's instructions. The blot was hybridised at 42° C. in 50% formamide with the relevant $^{32}$P labelled probe made from SEQ ID NO:20 for 16 hours. Blots were washed twice in 2×SSC (NaCl-Sodium Citrate buffer) at room temperature then in 0.5×SSC at 55° C. for 20 minutes. Autoradiographs were obtained after an overnight exposure. Panel A shows total RNA from developing seed of *Euphorbia lagascae* (1), *Euphorbia cyparissus* (2), *Vernonia galamensis* (3) and flax (*Linum usitatissimum*) (4). Panel B shows total RNA from various tissue of *Euphorbia lagascae*, including developing seed (1), root (2) and leaf (3).

DETAILED DESCRIPTION OF THE PREFERRED EMBODIMENTS

Figure 1:
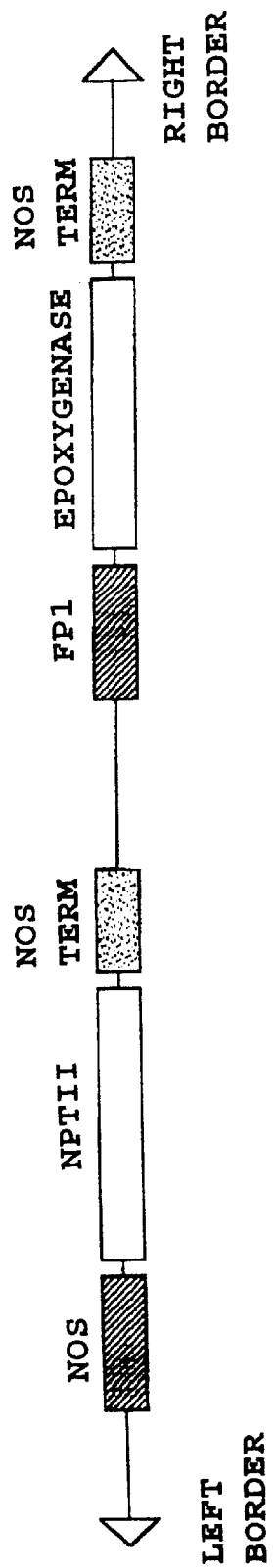
FIG. 1 is a linear representation of an expression plasmid comprising an epoxygenase structural gene, placed operably under the control of the truncated napin promoter (FP1; right-hand hatched box) and placed upstream of the NOS terminator sequence (right-hand stippled box). The epoxygenase genetic sequence is indicated by the right-hand open rectangular box. The construct also comprises the NOS promoter (left-hand hatched box) driving expression of the NPTII gene (left-hand open box) and placed upstream of the NOS terminator (left-hand stippled box). The left and right border sequences of the *Agrobacterium tumefaciens* Ti plasmid are also indicated.

One aspect of the present invention provides an isolated nucleic acid molecule which encodes or is complementary to an isolated nucleic acid molecule which encodes a fatty acid epoxygenase.

Wherein the isolated nucleic acid molecule of the invention encodes an enzyme which is involved in the direct epoxidation of arachidonic acid, it is particularly preferred that the subject nucleic acid molecule is derived from a non-mammalian source.

As used herein, the term "derived from" shall be taken to indicate that a particular integer or group of integers has originated from the species specified, but has not necessarily been obtained directly from the specified source.

The term "non-mammalian source" refers to any organism other than a mammal or a tissue or cell derived from same.

In the present context, the term "derived from a non-mammalian source" shall be taken to indicate that a particular integer or group of integers has been derived from bacteria, yeasts, birds, amphibians, reptiles, insects, plants, fungi, moulds and algae or other non-mammal.

In a preferred embodiment of the present invention, the source organism is any such organism possessing the genetic capacity to synthesize epoxy fatty acids. More preferably, the source organism is a plant such as, but not limited to Chrysanthemum spp., Crepis spp., Euphorbia spp. and Vernonia spp., amongst others.

Even more preferably, the source organism is selected from the list comprising *Crepis biennis, Crepis aurea, Crepis conyzaefolia, Crepis intermedia, Crepis occidentalis, Crepis palaestina, Crepis vesicaria, Crepis xacintha, Euphorbia lagascae* and *Vernonia galamensis*. Additional species are not excluded.

In a particularly preferred embodiment of the present invention, the source organism is a Crepis sp. which contains high levels of vernolic acid such as *Crepis palaestrina*, amongst others or alternatively, *Vernonia galamensis* or *Euphorbia lagascae.*

Wherein the isolated nucleic acid molecule of the invention encodes a Δ6-epoxygenase or Δ9-epoxygenase enzyme or Δ12-epoxygenase or Δ15-epoxygenase enzyme, or at least encodes an enzyme which is not involved in the direct epoxidation of arachidonic acid, the subject nucleic acid molecule may be derived from any source producing said enzyme, including, but not limited to, yeasts, moulds, bacteria, insects, birds, mammals and plants.

The nucleic acid molecule of the invention according to any of the foregoing embodiments may be DNA, such as a gene, cDNA molecule, RNA molecule or a synthetic oligonucleotide molecule, whether single-stranded or double-stranded and irrespective of any secondary structure characteristics unless specifically stated.

Reference herein to a "gene" is to be taken in its broadest context and includes:

(i) a classical genomic gene consisting of transcriptional and/or translational regulatory sequences and/or a coding region and/or non-translated sequences (i.e. introns, 5'- and 3'-untranslated sequences); or (ii) mRNA or cDNA corresponding to the coding regions (i.e. exons) and 5'- and 3'-untranslated sequences of the gene.

The term "gene" is also used to describe synthetic or fusion molecules encoding all or part of a functional product. Preferred epoxygenase genes of the present invention may be derived from a naturally-occurring epoxygenase gene by standard recombinant techniques. Generally, an epoxygenase gene may be subjected to mutagenesis to produce single or multiple nucleotide substitutions, deletions and/or additions.

Nucleotide insertional derivatives include 5' and 3' terminal fusions as well as intra-sequence insertions of single or multiple nucleotides. Insertional nucleotide sequence variants are those in which one or more nucleotides are introduced into a predetermined site in the nucleotide sequence although random insertion is also possible with suitable screening of the resulting product.

Deletional variants are characterised by the removal of one or more nucleotides from the sequence.

Substitutional nucleotide variants are those in which at least one nucleotide in the sequence has been removed and a different nucleotide inserted in its place. Such a substitution may be "silent" in that the substitution does not change the amino acid defined by the codon. Alternatively, substituents are designed to alter one amino acid for another similar acting amino acid, or amino acid of like charge, polarity, or hydrophobicity.

In the context of the present invention, the term "fatty acid epoxygenase" shall be taken to refer to any enzyme or functional equivalent or enzymatically-active derivative thereof which catalyzes the biosynthesis of an epoxygenated fatty acid, by converting a carbon bond of a fatty acid to an epoxy group and preferably, by converting a carbon double bond of an unsaturated fatty acid to an epoxy group. Although not limiting the invention, a fatty acid epoxygenase may catalyze the biosynthesis of an epoxy fatty acid selected from the list comprising 12,13-epoxy-9-octadecenoic acid (vernolic acid), 12,13-epoxy-9,15-octadecadienoic acid, 15,16-epoxy-9,12-octadecadienoic acid, 9,10-epoxy-12-octadecenoic acid, and 9,10-epoxy-octadecanoic acid, amongst others.

The term "epoxy", "epoxy group" and "epoxy residue" will be known by those skilled in the art to refer to a three membered ring comprising two carbon atoms and an oxygen atom linked by single bonds as follows:

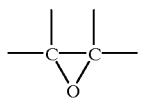

Accordingly, the term "epoxide" refers to compounds which comprise at least one epoxy group as hereinbefore defined.

Those skilled in the art are aware that fatty acid nomenclature is based upon the length of the carbon chain and the position of unsaturated carbon atoms within that carbon chain. Thus, fatty acids are designated using the shorthand notation:

$$\text{Carbon}_{total}\text{:double bond}_{total}^{double\ bond(\Delta)position},$$

wherein the double bonds are cis unless otherwise indicated. For example, palmitic acid (n-hexadecanoic acid) is a saturated 16-carbon fatty acid (i.e. 16:0), oleic acid (octadecenoic acid) is an unsaturated 18-carbon fatty acid with one double bond between C-9 and C-10 (i.e. $18:1^{\Delta 9}$), and linoleic acid (octadecadienoic acid) is an unsaturated 18-carbon fatty acid with two double bonds between C-9 and C-10 and between C-12 and C-13 (i.e. $18:2^{\Delta 9,12}$).

However, in the present context an epoxygenase enzyme may catalyze the conversion of any carbon bond to an epoxy group or alternatively, the conversion of any double in an unsaturated fatty acid substrate to an epoxy group. In this regard, it is well-known by those skilled in the art that most mono-unsaturated fatty acids of higher organisms are 18-carbon unsaturated fatty acids (i.e. $18:1^{\Delta 9}$, while most polyunsaturated fatty acids derived from higher organisms are 18-carbon fatty acids with at least one of the double bonds therein located between C-9 and C-10. Additionally, bacteria also possess C16-mono-unsaturated fatty acids. Moreover, the epoxygenase of the present invention may act on more than a single fatty acid substrate molecule and, as a consequence, the present invention is not to be limited by the nature of the substrate molecule upon which the subject epoxygenase enzyme acts.

Preferably, the substrate molecule for the epoxygenase of the present invention is an unsaturated fatty acid which contains at least one double bond.

Furthermore, epoxygenase enzymes may act upon any number of carbon atoms in any one substrate molecule. For example, they may be characterised as Δ6-epoxygenase, Δ9-epoxygenase, Δ12-epoxygenase or Δ15-epoxygenase enzymes amongst others. Accordingly, the present invention is not limited by the position of the carbon atom in the substrate upon which an epoxygenase enzyme may act.

The term "Δ6-epoxygenase" as used herein shall be taken to refer to an epoxygenase enzyme which catalyzes the conversion of the Δ6 carbon bond of a fatty acid substrate to a Δ6 epoxy group and preferably, catalyzes the conversion of the Δ6 double bond of at least one unsaturated fatty acid to a Δ6 epoxy group.

The term "Δ9-epoxygenase" as used herein shall be taken to refer to an epoxygenase enzyme which catalyzes the conversion of the Δ9 carbon bond of a fatty acid substrate to a Δ9 epoxy group and preferably, catalyzes the conversion of the Δ9 double bond of at least one unsaturated fatty acid to a Δ9 epoxy group.

As used herein, the term "Δ12-epoxygenase" shall be taken to refer to an epoxygenase enzyme which catalyzes the conversion of the Δ12 carbon bond of a fatty acid substrate to a Δ12 epoxy group and preferably, catalyzes the conversion of the Δ12 double bond of at least one unsaturated fatty acid to a Δ12 epoxy group.

As used herein, the term "Δ15-epoxygenase" shall be taken to refer to an epoxygenase enzyme which catalyzes the conversion of the Δ15 carbon bond of a fatty acid substrate to a Δ15 epoxy group and preferably, catalyzes the conversion of the Δ15 double bond of at least one unsaturated fatty acid to a Δ15 epoxy group.

The present invention clearly extends to genetic sequences which encode all of the epoxygenase enzymes listed supra, amongst others.

In one preferred embodiment of the invention, the isolated nucleic acid molecule encodes a fatty acid epoxygenase enzyme which converts at least one carbon bond in palmitoleic acid ($16:1^{\Delta 9}$), oleic acid ($18:1^{\Delta 9}$), linoleic acid ($18:2^{\Delta 9,12}$), linolenic acid ($18:3^{\Delta 9,12,15}$), or arachidonic acid ($20:4^{\Delta 5,8,11,14}$) to an epoxy bond. Preferably, the carbon bond is a carbon double bond.

More preferably, the isolated nucleic acid molecule of the invention encodes a fatty acid epoxygenase enzyme which at least converts one or both double bonds in linoleic acid to an epoxy group. According to this embodiment, an epoxygenase which converts both the Δ9 and the Δ12 double bonds of linoleic acid to an epoxy group may catalyze such conversions independently of each other such that said epoxygenase is a Δ9-epoxygenase and/or a Δ12-epoxygenase enzyme as hereinbefore defined.

In an alternative preferred embodiment, the fatty acid epoxygenase of the present invention is a Δ12-epoxygenase, a Δ15-epoxygenase or a Δ9-epoxygenase as hereinbefore defined.

More preferably, the fatty acid epoxygenase of the invention is a Δ12-epoxygenase as hereinbefore defined.

In a particularly preferred embodiment of the invention, there is provided an isolated nucleic acid molecule which encodes linoleate Δ12-epoxygenase, the epzyme which at least converts the Δ12 double bond of linoleic acid to a Δ12-epoxy group, thereby producing 12,13-epoxy-9-octadecenoic acid (vernolic acid).

Although not limiting the present invention, the preferred source of the Δ12-epoxygenase of the invention is a plant, in particular *Crepis palaestrina* or a further Crepis sp. which is distinct from *C. palaestina* but contains high levels of vernolic acid, *Vernonia galamensis* or *Euphorbia lagascae*.

According to this embodiment, a Δ12-epoxygenase may catalyze the conversion of palmitoleic acid to 9,10-epoxy-palmitic acid and/or the conversion of oleic acid to 9,10-epoxy-stearic acid and/or the conversion of linoleic acid to any one or more of 9,10-epoxy-12-octadecenoic acid or 12,13-epoxy-9-octadecenoic acid or 9,10,12,13-diepoxy-stearic acid and/or the conversion of linolenic acid to any one or more of 9,10-epoxy-12,15-octadecadienoic acid or 12,13-epoxy-9,15-octadecadienoic acid or 15,16-epoxy-octadecadienoic acid or 9,10,12,13-diepoxy-15-octadecenoic acid or 9,10,15, 16-diepoxy-12-octadecenoic acid or 12,13,15,16-diepoxy-9-octadecenoic acid or 9,10,12,13,15,16-triepoxy-stearic acid and/or the conversion of arachidonic acid to any one or more of 5,6-epoxy-8,11,14-tetracosatrienoic acid or 8,9-epoxy-5,11,14-tetracosatrienoic acid or 11,12-epoxy-5,8,14-tetracosatrienoic acid or 14,15-epoxy-5,8,11-tetracosatrienoic acid or 5,6,8,9-diepoxy-11,14-tetracosadienoic acid or 5,6,11,12-diepoxy-8,14-tetracosadienoic acid or 5,6,14,15-diepoxy-8,11-tetracosadienoic acid or 8,9,11,12-diepoxy-5,14-tetracosadienoic acid or 8,9,14,15-diepoxy-5,11-tetracosadienoic acid or 11,12,14,15-diepoxy-5,8-tetracosadienoic acid or 5,6,8,9,11,12-triepoxy-14-tetracosenoic acid or 5,6,8,9,14,15-triepoxy-11-tetracosenoic acid or 5,6,11,12,14,15-triepoxy-8-tetracosenoic acid or 8,9,11,12,14,15-triepoxy-5-tetracosenoic acid, amongst others.

Those skilled in the art may be aware that not all substrates listed supra may be derivable from a natural source, but notwithstanding this, may be produced by chemical synthetic means. The conversion of both naturally-occurring and chemically-synthesized unsaturated fatty acids to epoxy fatty acids is within the scope of the present invention, the only requirement being that the nucleic acid molecule of the present invention as described herein encodes an enzyme or functional part thereof which is capable of catalyzing said conversion.

According to the preceding discussion, those skilled in the art will be aware that a fatty acid epoxygenase may be a cytochrome-P450-dependent monooxygenase enzyme or a mixed-function monooxygenase enzyme or alternatively a peroxide-dependent peroxygenase enzyme, or like enzyme, amongst others. However, the present invention is particularly directed to those epoxygenase enzymes which are mixed-function monooxygenase enzymes and nucleic acid molecules encoding same and uses therefor. Accordingly, it is particularly preferred that the nucleic acid molecule of the invention encode a fatty acid epoxygenase which is a mixed-function monooxygenase enzyme.

In the context of the present invention, the term "mixed-function monooxygenase enzyme" shall be taken to refer to any enzyme which catalyzes the epoxygenation of a carbon bond or carbon double bond in a fatty acid molecule, wherein said enzyme further comprises a sequence of amino acids which contains three histidine-rich regions as follows:

(i) His-(Xaa)$_{3-4}$-His;

(ii) His-(Xaa)$_{2-3}$-His-His; and (iii) His-(Xaa)$_{2-3}$-His-His, wherein His designates histidine, Xaa designates any naturally-occurring amino acid residue as set forth in Table 1 herein, the integer (Xaa)$_{3-4}$ refers to a sequence of amino acids comprising three or four repeats of Xaa, and the integer (Xaa)$_{2-3}$ refers to a sequence of amino acids comprising two or three repeats of Xaa.

The term "mixed-function monooxygenase enzyme-like" shall be taken to refer to any enzyme which comprises three of the histidine-rich regions listed supra.

In the exemplification of the invention described herein, the inventors have demonstrated that the *Crepis palaestrina* amino acid sequence provided herein comprises a Δ12-epoxygenase enzyme which includes the characteristic amino acid sequence motifs of a mixed-function monooxygenase enzyme as hereinbefore defined. Close amino acid sequence identity between the *C. palaestrina* Δ12-epoxygenase enzyme (SEQ ID NO: 2) and the amino acid sequences of polypeptides derived from an unidentified Crepis sp. and *Vernonia galamensis* as provided herein (SEQ ID NOs: 4 and 6), compared to the amino acid sequences of other mixed function monooxygenases such as desaturases and hydroxylases, suggests that said Crepis sp. and *V. galamensis* amino acid sequences are also fatty acid epoxygenase enzymes and may be Δ12-epoxygenase enzymes. In this regard, the *Vernonia galamensis* amino acid sequence exemplified herein is a partial sequence which comprises only one complete histidine-rich motif (i.e. His-Arg-Asn-His-His) and a partial sequence of the first histidine-rich motif (i.e. it comprises the last two histidine residues of the His-Glu-Cys-Gly-His-His motif), because the corresponding nucleotide sequence encoding same was amplified by polymerase chain reaction as a partial cDNA sequence, using a first primer to this first histidine-rich motif and a second amplification primer designed to a region upstream of the third histidine-rich motif (i.e. His-Val-Met-His-His). Additionally, the fact that the *V. galamensis* sequence was amplified using a primer specific for the first histidine-rich motif indicates that the corresponding full-length sequence would also comprise this motif.

Accordingly, in a particularly preferred embodiment, the nucleic acid molecule of the invention encodes an mixed-function monooxygenase epoxygenase enzyme or like enzyme derived from Crepis spp., including *Crepis palastina* or alternatively, derived from *Vernonia galamensis*. According to this embodiment, it is even more preferred that the subject epoxygenase at least comprises a sequence of amino acids which contains three or more histidine-rich regions as follows:

(i) His-Glu-Cys-Gly-His-His (SEQ ID NO: 15);

(ii) His-Arg-Asn-His-His (SEQ ID NO: 16); and (iii) His-Val-Met-His-His (SEQ ID NO: 17), or a homologue, analogue or derivative thereof, wherein His designates histidine, Glu designates glutamate, Cys designates cysteine, Gly designates glycine, Arg designates arginine, Asn designates asparagine, Val designates valine, Met designates methionine.

The present invention clearly extends to epoxygenase genes derived from other species, including the epoxygenase genes derived from Chrysanthemum spp. and *Euphorbia lagascae*, amongst others.

In a preferred embodiment, whilst not limiting the present invention, the epoxygenase genes of other species which are encompassed by the present invention encode mixed-function monooxygenase enzymes. The present invention further extends to the isolated or recombinant polypeptides encoded by such genes and uses of said genes and polypeptides.

The invention described according to this embodiment does not encompass nucleic acid molecules which encode enzyme activities other than epoxygenase activities as defined herein, in particular the Δ12-desaturase enzymes derived from *Arabidopsis thaliana, Brassica juncea, Brassica napus* or *Glycine max*, amongst others, which are known to contain similar histidine-rich motifs.

In the present context, "homologues" of an amino acid sequence refer to those amino acid sequences or peptide sequences which are derived from polypeptides, enzymes or proteins of the present invention or alternatively, correspond substantially to the amino acid sequences listed supra, notwithstanding any naturally-occurring amino acid substitutions, additions or deletions thereto.

For example, amino acids may be replaced by other amino acids having similar properties, for example hydrophobicity, hydrophilicity, hydrophobic moment, antigenicity, propensity to form or break α-helical structures or β-sheet structures, and so on. Alternatively, or in addition, the amino acids of a homologous amino acid sequence may be replaced by other amino acids having similar properties, for example hydrophobicity, hydrophilicity, hydrophobic moment, charge or antigenicity, and so on.

Naturally-occurring amino acid residues contemplated herein are described in Table 1.

A homologue of an amino acid sequence may be a synthetic peptide produced by any method known to those skilled in the art, such as by using Fmoc chemistry.

Alternatively, a homologue of an amino acid sequence may be derived from a natural source, such as the same or another species as the polypeptides, enzymes or proteins of the present invention. Preferred sources of homologues of the amino acid sequences listed supra include any of the sources contemplated herein.

"Analogues" of an amino acid sequence encompass those amino acid sequences which are substantially identical to the amino acid sequences listed supra notwithstanding the occurrence of any non-naturally occurring amino acid analogues therein.

Preferred non-naturally occurring amino acids contemplated herein are listed below in Table 2.

The term "derivative" in relation to an amino acid sequence shall be taken to refer hereinafter to mutants, parts, fragments or polypeptide fusions of the amino acid sequences listed supra. Derivatives include modified amino acid sequences or peptides in which ligands are attached to one or more of the amino acid residues contained therein, such as carbohydrates, enzymes, proteins, polypeptides or reporter molecules such as radionuclides or fluorescent compounds. Glycosylated, fluorescent, acylated or alkylated forms of the subject peptides are also contemplated by the present invention. Additionally, derivatives may comprise fragments or parts of an amino acid sequence disclosed herein and are within the scope of the invention, as are homopolymers or heteropolymers comprising two or more copies of the subject sequences.

Procedures for derivatizing peptides are well-known in the art.

Substitutions encompass amino acid alterations in which an amino acid is replaced with a different naturally-occurring or a non-conventional amino acid residue. Such substitutions may be classified as "conservative", in which case an amino acid residue is replaced with another naturally-occurring amino acid of similar character, for example Gly⇌Ala, Val⇌Ile⇌Leu, Asp⇌Glu, Lys⇌Arg, Asn⇌Gln or Phe⇌Trp⇌Tyr.

Substitutions encompassed by the present invention may also be "non-conservative", in which an amino acid residue which is present in a repressor polypeptide is substituted with an amino acid having different properties, such as a naturally-occurring amino acid from a different group (eg. substituted a charged or hydrophobic amino acid with alanine), or alternatively, in which a naturally-occurring amino acid is substituted with a non-conventional amino acid.

Amino acid substitutions are typically of single residues, but may be of multiple residues, either clustered or dispersed.

Amino acid deletions will usually be of the order of about 1–10 amino acid residues, while insertions may be of any length. Deletions and insertions may be made to the N-terminus, the C-terminus or be internal deletions or insertions. Generally, insertions within the amino acid sequence will be smaller than amino-or carboxyl-terminal fusions and of the order of 1–4 amino acid residues.

The present invention clearly extends to the subject isolated nucleic acid molecule when integrated into the genome of a cell as an addition to the endogenous cellular complement of epoxygenase genes. Alternatively, wherein the host cell does not normally encode enzymes required for epoxy fatty acid biosynthesis, the present invention extends to the subject isolated nucleic acid molecule when integrated into the genome of said cell as an addition to the endogenous cellular genome.

TABLE 1

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 2

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
| | | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
| | | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolyethyl)glycine | Nhis |
| D-N-methylleucine | Dnmleu | N-(3-indolylyethyl) | Nhtrp |

TABLE 2-continued

| Non-conventional amino acid | Code | Non-conventional amino acid | Code |
|---|---|---|---|
| | | glycine | |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-2,2-diphenylethyl)carbamylmethyl)glycine | Nnbhm | N-(N-(3,3-diphenylpropyl)carbamylmethyl)glycine | Nnbhe |
| 1-carboxy-1-(2,2-diphenylethylamino)cyclopropane | Nmbc | | |

A second aspect of the present invention provides an isolated nucleic acid molecule which comprises the sequence of nucleotides set forth in any one of SEQ ID NOs:1 or 3 or 5 or 19 or 20 or a complementary sequence thereto, or a homologue, analogue or derivative thereof.

For the purposes of nomenclature, the nucleotide sequence set forth in SEQ ID NO:1 is derived from *Crepis palaestrina* and encodes the mixed function monooxygenase sequence or mixed function monooxygenase-like sequence set forth in SEQ ID NO:2. As exemplified herein, the amino acid sequence set forth in SEQ ID NO:2 has epoxygenase activity, more particularly Δ12-epoxygenase activity.

The nucleotide sequence set forth in SEQ ID NO: 3 corresponds to a cDNA derived from a Crepis sp. other than *C. palaestina* which contains high levels of vernolic acid. The amino acid sequence set forth in SEQ ID NO: 4 corresponds to the derived amino acid sequence of the Crepis sp. epoxygenase gene provided in SEQ ID NO:3.

The nucleotide sequence set forth in SEQ ID NO: 5 corresponds to amplified DNA derived from *Vernonia galamensis* using amplification primers derived from a consensus sequence of mixed function monooxygenases, including the Crepis spp. epoxygenase gene sequences of the invention. The amplified DNA comprises a partial epoxygenase gene sequence, which includes nucleotide sequences capable of encoding the histidine-rich motif His-Arg-Asn-His-His which is characteristic of mixed function monooxygenase enzymes. The amino acid sequence set forth in SEQ ID NO: 6 corresponds to the derived amino acid sequence of the *Vernonia galamensis* epoxygenase gene provided in SEQ ID NO:5.

The nucleotide sequence set forth in SEQ ID NO:7 relates to the partial sequence of a *Crepis alpina* acetylenase gene which was used as a probe to isolate the nucleic acid molecule comprising the nucleotide sequence set forth in SEQ ID NO: 1. The amino acid sequence set forth in SEQ ID NO:8 corresponds to the derived amino acid sequence of said partial sequence of the *C. alpina* acetylenase gene.

As used herein, the term "acetylenase" shall be taken to refer to an enzyme which is capable of catalyzing the conversion of a carbon double bond in a fatty acid substrate molecule to a carbon triple bond or alternatively, which is capable of catalyzing the formation of a carbon triple bond in a fatty acid molecule.

The nucleotide sequence set forth in SEQ ID NO:18 corresponds to a degenerate amplification primer used to amplify putative *Euphorbia lagascae* epoxygenase gene sequences. In this regard, the nucleotide residues shown in SEQ ID NO:18 are those recommended by the IUPAC-IUB Biochemical Nomenclature Commission, wherein A represents Adenine, C represents Cytosine, G represents Guanine, T represents thymine, Y represents a pyrimidine residue, R represents a purine residue, M represents Adenine or Cytosine, K represents Guanine or Thymine, S represents Guanine or Cytosine, W represents Adenine or Thymine, H represents a nucleotide other than Guanine, B represents a nucleotide other than Adenine, V represents a nucleotide other than Thymine, D represents a nucleotide other than Cytosine and N represents any nucleotide residue.

The nucleotide sequence set forth in SEQ ID NO:19 is derived from *Euphorbia lagascae* and encodes the putative cytochrome P450-dependent monooxygenase sequence or cytochrome P-450-dependent monooxygenase-like sequence.

The nucleotide sequence set forth in SEQ ID NO: 20 is derived from *Euphorbia lagascae* and encodes a putative cytochrome P-450-dependent monooxygenase sequence or cytochrome P-450-dependent monooxygenase-like sequence.

The present invention clearly extends to the genomic gene equivalents of the cDNA molecules exemplified in any one of SEQ ID NOs: 1, 3, 5, 19 or 20.

In a most particularly preferred embodiment, the present invention provides an isolated nucleic acid molecule which comprises the nucleotide sequence set forth in any one of SEQ ID NOs: 1, 3, 5, 19 or 20 or a genomic gene equivalent of said nucleotide sequence or a homologue, analogue or derivative thereof.

For the present purpose, "homologues" of a nucleotide sequence shall be taken to refer to an isolated nucleic acid molecule which is substantially the same as the nucleic acid molecule of the present invention or its complementary nucleotide sequence, notwithstanding the occurrence within said sequence, of one or more nucleotide substitutions, insertions, deletions, or rearrangements.

"Analogues" of a nucleotide sequence set forth herein shall be taken to refer to an isolated nucleic acid molecule which is substantially the same as a nucleic acid molecule of the present invention or its complementary nucleotide sequence, notwithstanding the occurrence of any non-nucleotide constituents not normally present in said isolated nucleic acid molecule, for example carbohydrates, radiochemicals including radionucleotides, reporter molecules such as, but not limited to DIG, alkaline phosphatase or horseradish peroxidase, amongst others.

"Derivatives" of a nucleotide sequence set forth herein shall be taken to refer to any isolated nucleic acid molecule which contains significant sequence similarity to said sequence or a part thereof.

Generally, homologues, analogues or derivatives of the nucleic acid molecule of the invention are produced by synthetic means or alternatively, derived from naturally-occurring sources. For example, the nucleotide sequence of the present invention may be subjected to mutagenesis to produce single or multiple nucleotide substitutions, deletions and/or insertions as indicated supra.

In one embodiment of the invention, preferred homologues, analogues or derivatives of the nucleotide sequences set forth in any one of SEQ ID NOs: 1, 3, 5, 19 or 20 or complementary sequences thereto, encode immunologically-active or enzymatically-active polypeptides.

As used herein, the term "immunologically-active" shall be taken to refer to the ability of a polypeptide molecule to elicit an immune response in a mammal, in particular an immune response sufficient to produce an antibody molecule such as, but not limited to, an IgM or IgG molecule or whole serum containing said antibody molecule. The term "immunologically-active" also extends to the ability of a polypeptide to elicit a sufficient immune response for the production of monoclonal antibodies, synthetic Fab fragments of an antibody molecule, single-chain antibody molecule or other immunointeractive molecule.

As used herein, the term "enzymatically-active" shall be taken to refer to the ability of a polypeptide molecule to catalyse an enzyme reaction, in particular an enzyme reaction which comprises the epoxygenation of a carbon bond in a fatty acid substrate molecule. More particularly, whilst not limiting the invention, the term "enzymatically-active" may also refer to the ability of a polypeptide molecule to catalyse the epoxygenation of Δ-9 or Δ-12 in a fatty acid substrate molecule such as linoleic acid or vernolic acid.

In an alternative embodiment, a preferred homologue, analogue or derivative of the nucleotide sequence set forth in any one of SEQ ID NOs: 1 or 3 or 5, or a complementary sequence thereto, comprises a sequence of nucleotides which is at least 65% identical to at least 20 contiguous nucleotides therein, other than a nucleotide sequence which encodes a Crepis sp. acetylenase enzyme.

More preferably, the percentage identity to any one of SEQ ID NOs: 1 or 3 or 5 is at least about 85%. Even more preferably, a homologue, analogue or derivative of SEQ ID NOs: 1 or 3 or 5 is at least about 90% and even more preferably at least about 95% identical to at least 100 or 250 or 500 or 1000 contiguous nucleotides therein.

The percentage identity to SEQ ID NOs: 19 or 20, or complementary sequences thereto is at least about 75% over at least about 200 contiguous nucleotides, even more preferably at least about 80%, still even more preferably at least about 90% and still even more preferably at least about 95%, including at least about 99% identity. Nucleotide sequences which are at least 65% over at least about 400 contiguous nucleotides in SEQ ID NOs: 19 or 20 are also within the scope of the invention.

Reference herein to a percentage identity or percentage similarity between two or more nucleotide or amino acid sequences shall be tiken to refer to the number of identical or similar residues in a nucleotide or amino acid sequence alignment, as determined using any standard algorithm known by those skilled in the art. In particular, nucleotide and/or amino acid sequence identities and similarities may be calculated using the Gap program, which utilises the algorithm of Needleman and Wunsch (1970) to maximise the number of residue matches and minimise the number of sequence gaps. The Gap program is part of the Sequence and Analysis Software Package of the Computer Genetics Group Inc., University Research Park, Madison, Wis., United States of America (Devereux et al., 1984).

In a further alternative embodiment, a preferred homologue, analogue or derivative of the nucleotide sequence set forth in any one of SEQ ID NOs: 1, 3, 5, 19 or 20 or a complementary sequence thereto, hybridizes under at least low stringency conditions to at least 20 contiguous nucleotides derived from said sequence.

More preferably, the stringency of hybridization is at least moderate stringency, even more preferably at least high stringency.

For the purposes of defining the level of stringency, those skilled in the art will be aware that several different hybridisation conditions may be employed. For example, a low stringency may comprise a hybridisation and/or a wash carried out in 6×SSC buffer, 0.1% (w/v) SDS at 28° C. A moderate stringency may comprise a hybridisation and/or wash carried out in 2×SSC buffer, 0.1% (w/v) SDS at a temperature in the range 45° C. to 65° C. A high stringency may comprise a hybridisation and/or wash carried out in 0.1×SSC buffer, 0.1% (w/v) SDS at a temperature of at least 65° C.

Generally, the stringency is increased by reducing the concentration of SSC buffer, and/or increasing the concentration of SDS in the hybridisation buffer or wash buffer and/or increasing the temperature at which the hybridisation and/or wash are performed. Conditions for hybridisations and washes are well understood by one normally skilled in the art. For the purposes of clarification of parameters affecting hybridisation between nucleic acid molecules, reference can conveniently be made to pages 2.10.8 to 2.10.16. of Ausubel et al. (1987), which is herein incorporated by reference.

The isolated nucleic acid molecules disclosed herein may be used to isolate or identify homologues, analogues or derivatives thereof from other cells, tissues, or organ types, or from the cells, tissues, or organs of another species using any one of a number of means known to those skilled in the art.

For example, genomic DNA, or mRNA, or cDNA may be contacted, under at least low stringency hybridisation conditions or equivalent, with a hybridisation effective amount of an isolated nucleic acid molecule which comprises the nucleotide sequence set forth in any one SEQ ID NOs: 1, 3, 5, 19 or 20 or a complementary sequence thereto, or a functional part thereof, and hybridisation detected using a detection means.

The detection means may be a reporter molecule capable of giving an identifiable signal (e.g. a radioisotope such as $^{32}P$ or $^{35}S$ or a biotinylated molecule) covalently linked to the isolated nucleic acid molecule of the invention.

In an alternative method, the detection means is any known format of the polymerase chain reaction (PCR). According to this method, degenerate pools of nucleic acid "primer molecules" of about 15–50 nucleotides in length are designed based upon the nucleotide sequences disclosed in SEQ ID NOs: 1, 3, 5, 19 or 20 or a complementary sequence thereto. The homologues, analogues or derivatives (i.e. the "template molecule") are hybridized to two of said primer molecules, such that a first primer hybridizes to a region on one strand of the template molecule and a second primer hybridizes to a complementary sequence thereof, wherein the first and second primers are not hybridized within the same or overlapping regions of the template molecule and wherein each primer is positioned in a 5'- to 3'-orientation relative to the position at which the other primer is hybridized on the opposite strand. Specific nucleic acid molecule copies of the template molecule are amplified enzymatically in a polymerase chain reaction, a technique that is well known to one skilled in the art.

The primer molecules may comprise any naturally-occurring nucleotide residue (i.e. adenine, cytidine, guanine, thymidine) and/or comprise inosine or functional analogues or derivatives thereof, capable of being incorporated into a polynucleotide molecule. The nucleic acid primer molecules may also be contained in an aqueous mixture of other nucleic acid primer molecules or be in a substantially pure form.

The detected sequence may be in a recombinant form, in a virus particle, bacteriophage particle, yeast cell, animal cell, or a plant cell. Preferably, the related genetic sequence originates from another plant species.

A third aspect of the present invention provides an isolated nucleic acid molecule which encodes the amino acid sequence set forth in any one of SEQ ID NOs: 2 or 4 or 6 or a homologue, analogue or derivative thereof.

In one embodiment contemplated herein, preferred homologues, analogues or derivatives of the amino acid sequences set forth in SEQ ID NOs: 2, 4, or 6 are immunologically-active or enzymatically-active polypeptides as defined supra.

In an alternative embodiment of the invention, preferred homologues, analogues or derivatives of the amino acid sequence set forth in any one of SEQ ID NOs: 2, 4 or 6 comprise a sequence of amino acids which is at least 60% identical thereto, other than a Crepis sp. acetylenase polypeptide. More preferably, homologues, analogues or derivatives of SEQ ID NOs:2 or 4 or 6 which are encompassed by the present invention are at least about 85% identical, even more preferably at least about 90% identical and still even more preferably at least about 95% identical, and still more preferably at least about 99%–100% identical thereto.

Homologues, analogues or derivatives of any one of SEQ ID NOs: 2 or 4 or 6 may further comprise a histidine-rich region as defined supra. Even more preferably, the subject epoxygenase at least comprises a sequence of amino acids which contains three or more histidine rich regions as follows:

(i) His-Glu-Cys-Gly-His-His (SEQ ID NO: 15);
(ii) His-Arg-Asn-His-His (SEQ ID NO: 16); and
(iii) His-Val-Met-His-His (SEQ ID NO: 17), or a homologue, analogue or derivative thereof.

The invention described according to this alternative embodiment does not encompass the Δ12-desaturase enzymes derived from *Arabidopsis thaliana, Brassica juncea, Brassica napus* or *Glycine max*, amongst others.

The isolated nucleic acid molecule of the present invention is useful for developing genetic constructs comprising a sense molecule wherein said genetic constructs are designed for the expression in a cell which does not normally express said nucleic acid molecule or over-expression of said nucleic acid molecule in a cell which does normally express the said nucleic acid molecule.

Accordingly, a further aspect of the invention provides a genetic construct which comprises a sense molecule which is operably connected to a promoter sequence.

The term "sense molecule" as used herein shall be taken to refer to an isolated nucleic acid molecule which encodes or is complementary to an isolated nucleic acid molecule which encodes a fatty acid epoxygenase wherein said nucleic acid molecule is provided in a format suitable for its expression to produce a recombinant polypeptide when said sense molecule is introduced into a host cell by transfection or transformation.

Those skilled in the art will be aware that a genetic construct may be used to "transfect" a cell, in which case it is introduced into said cell without integration into the cell's genome. Alternatively, a genetic construct may be used to "transform" a cell, in which case it is stably integrated into the genome of said cell.

A sense molecule which corresponds to a fatty acid epoxygenase gene sequence or homologue, analogue or derivative thereof, may be introduced into a cell using any known method for the transfection or transformation of said cell. Wherein a cell is transformed by the genetic construct of the invention, a whole organism may be regenerated from a single transformed cell, using any method known to those skilled in the art.

Thus, the epoxygenase genes described herein may be used to develop single cells or whole organisms which synthesize epoxy fatty acids not normally produced by wild or naturally-occurring organisms belonging to the same genera or species as the genera or species from which the transfected or transformed cell is derived, or to increase the levels of such fatty acids above the levels normally found in such wild or naturally-occurring organisms.

In an alternative preferred embodiment, the isolated nucleic acid molecule of the invention is capable of reducing the level of epoxy fatty acids in a cell, when expressed therein, in the antisense orientation or as a ribozyme or co-suppression molecule, under the control of a suitable promoter sequence.

Co-suppression is the reduction in expression of an endogenous gene that occurs when one or more copies of said gene, or one or more copies of a substantially similar gene are introduced into the cell. The present invention also extends to the use of co-suppression to inhibit the expression of an epoxygenase gene as described herein.

In the context of the present invention, an antisense molecule is an RNA molecule which is transcribed from the complementary strand of a nuclear gene to that which is normally transcribed to produce a "sense" mRNA molecule capable of being translated into a polypeptide. The antisense molecule is therefore complementary to the sense mRNA, or a part thereof. Although not limiting the mode of action of the antisense molecules of the present invention to any specific mechanism, the antisense RNA molecule possesses the capacity to form a double-stranded mRNA by base pairing with the sense mRNA, which may prevent translation of the sense mRNA and subsequent synthesis of a polypeptide gene product.

Ribozymes are synthetic RNA molecules which comprise a hybridising region complementary to two regions, each of at least 5 contiguous nucleotide bases in the target sense mRNA. In addition, ribozymes possess highly specific endoribonuclease activity, which autocatalytically cleaves the target sense mRNA. A complete description of the function of ribozymes is presented by Haseloff and Gerlach (1988) and contained in International Patent Application No. WO89/05852. The present invention extends to ribozymes which target a sense mRNA encoding an epoxygenase polypeptide described herein, thereby hybridising to said sense mRNA and cleaving it, such that it is no longer capable of being translated to synthesise a functional polypeptide product.

According to this embodiment, the present invention provides a ribozyme or antisense molecule comprising a sequence of contiguous nucleotide bases which are able to form a hydrogen-bonded complex with a sense mRNA encoding an epoxygenase described herein, to reduce translation of said mRNA. Although the preferred antisense and/or ribozyme molecules hybridise to at least about 10 to 20 nucleotides of the target molecule, the present invention extends to molecules capable of hybridising to at least about 50–100 nucleotide bases in length, or a molecule capable of hybridising to a full-length or substantially full-length epoxygenase mRNA.

It is understood in the art that certain modifications, including nucleotide substitutions amongst others, may be made to the antisense and/or ribozyme molecules of the present invention, without destroying the efficacy of said molecules in inhibiting the expression of the epoxygenase gene. It is therefore within the scope of the present invention to include any nucleotide sequence variants, homologues, analogues, or fragments of the said gene encoding same, the only requirement being that said nucleotide sequence variant, when transcribed, produces an antisense and/or ribozyme molecule which is capable of hybridising to the said sense mRNA molecule.

The present invention extends to genetic constructs designed to facilitate expression of a sense molecule, an antisense molecule, ribozyme molecule, or co-suppression molecule which is capable of altering the level of epoxy fatty acids in a cell.

In a particularly preferred embodiment, the sense molecule, an antisense molecule, ribozyme molecule, co-suppression molecule, or gene targeting molecule which is capable of altering the epoxy fatty acid composition of a cell derived from plant or other organism comprises a sequence of nucleotides set forth in any one of SEQ ID NOs: 1, 3, 5, 19 or 20 and more preferably in any one of SEQ ID NOs: 1 or 3 or 5 and even more preferably in SEQ ID NO: 1 or a complementary strand, homologue, analogue or derivative thereof.

Those skilled in the art will also be aware that expression of a sense, antisense, ribozyme or co-suppression molecule may require the nucleic acid molecule of the invention to be placed in operable connection with a promoter sequence. The choice of promoter for the present purpose may vary depending upon the level of expression of the sense molecule required and/or the species from which the host cell is derived and/or the tissue-specificity or development-specificity of expression of the sense molecule which is required.

Reference herein to a "promoter" is to be taken in its broadest context and includes the transcriptional regulatory sequences of a classical eukaryotic genomic gene, including the TATA box which is required for accurate transcription initiation, with or without a CCAAT box sequence and additional regulatory elements (i.e. upstream activating sequences, enhancers and silencers) which alter gene expression in response to developmental and/or external stimuli, or in a tissue-specific manner. In the context of the present invention, the term "promoter" also includes the transcriptional regulatory sequences of a classical prokaryotic gene, in which case it may include a −35 box sequence and/or a −10 box transcriptional regulatory sequences.

In the present context, the term "promoter" is also used to describe a synthetic or fusion molecule, or derivative which confers, activates or enhances expression of said sense molecule in a cell. Preferred promoters may contain additional copies of one or more specific regulatory elements, to further enhance expression of the sense molecule and/or to alter the spatial expression and/or temporal expression of said sense molecule. For example, copper-responsive regulatory elements may be placed adjacent to a heterologous promoter sequence driving expression of a sense molecule to confer copper inducible expression thereon.

Placing a sense, antisense, ribozyme or co-suppression molecule under the regulatory control of a promoter sequence means positioning said molecule such that expression is controlled by the promoter sequence. A promoter is usually, but not necessarily, positioned upstream or 5' of a nucleic acid molecule which it regulates. Furthermore, the regulatory elements comprising a promoter are usually positioned within 2 kb of the start site of transcription of the sense, antisense, ribozyme or co-suppression molecule or chimeric gene comprising same. In the construction of heterologous promoter/structural gene combinations it is generally preferred to position the promoter at a distance from the gene transcription start site that is approximately the same as the distance between that promoter and the gene it controls in its natural setting, i.e., the gene from which the promoter is derived. As is known in the art, some variation in this distance can be accommodated without loss of promoter function. Similarly, the preferred positioning of a regulatory sequence element with respect to a heterologous gene to be placed under its control is defined by the positioning of the element in its natural setting, i.e., the genes from which it is derived. Again, as is known in the art, some variation in this distance can also occur.

Examples of promoters suitable for use in genetic constructs of the present invention include promoters derived from the genes of viruses, yeasts, moulds, bacteria, insects, birds, mammals and plants which are capable of functioning in isolated cells or whole organisms regenerated therefrom. The promoter may regulate the expression of the sense, antisense, ribozyme or co-suppression molecule constitutively, or differentially with respect to the tissue in which expression occurs or, with respect to the developmental stage at which expression occurs, or in response to external stimuli such as physiological stresses, pathogens, or metal ions, amongst others.

Examples of promoters include the CaMV 35S promoter, NOS promoter, octopine synthase (OCS) promoter, *Arabidopsis thaliana* SSU gene promoter, napin seed-specific promoter, $P_{32}$ promoter, BK5-T imm promoter, lac promoter, tac promoter, phage lambda $\lambda_L$ or $\lambda_R$ promoters, CMV promoter (U.S. Pat. No. 5,168,062), T7 promoter, lacUV5 promoter, SV40 early promoter (U.S. Pat. No. 5,118,627), SV40 late promoter (U.S. Pat. No. 5,118,627), adenovirus promoter, baculovirus P10 or polyhedrin promoter (U.S. Pat. Nos. 5,243,041, 5,242,687, 5,266,317, 4,745,051 and 5,169,784), and the like. In addition to the specific promoters identified herein, cellular promoters. for so-called housekeeping genes are useful.

Preferred promoters according to this embodiment are those promoters which are capable of functioning in yeast, mould or plant cells. More preferably, promoters suitable for use according to this embodiment are capable of functioning in cells derived from oleaginous yeasts, oleaginous moulds or oilseed crop plants, such as flax sold under the trademark Linola® (hereinafter referred to as "Linola® flax"), sunflower, safflower, soybean, linseed, sesame, cottonseed, peanut, olive or oil palm, amongst others.

Linola® is a registered trade mark of the Commonwealth Scientific and Industrial Research Organisation (CSIRO), Australia.

In a more preferred embodiment, the promoter may be derived from a genomic clone encoding an epoxygenase enzyme, preferably derived from the genomic gene equivalents of epoxygenase genes derived from Chrysanthemum spp., Crepis spp. including *C. palaestina* or other Crepis sp., *Euphorbia lagascae* or *Vernonia galamensis*, which are referred to herein.

In a more preferred embodiment, the promoter may be derived from a highly-expressed seed gene, such as the napin gene, amongst others.

The genetic construct of the invention may further comprise a terminator sequence and be introduced into a suitable host cell where it is capable of being expressed to produce a recombinant polypeptide gene product or alternatively, a ribozyme or antisense molecule.

The term "terminator" refers to a DNA sequence at the end of a transcriptional unit which signals termination of transcription. Terminators are 3'-non-translated DNA sequences containing a polyadenylation signal, which facilitates the addition of polyadenylate sequences to the 3'-end of a primary transcript. Terminators active in cells derived from viruses, yeasts, moulds, bacteria, insects, birds, mammals and plants are known and described in the literature. They may be isolated from bacteria, fungi, viruses, animals and/or plants.

Examples of terminators particularly suitable for use in the genetic constructs of the present invention include the nopaline synthase (NOS) gene terminator of *Agrobacterium tamefaciens*, the terminator of the Cauliflower mosaic virus (CaMV) 35S gene, the zein gene terminator from *Zea mays*, the Rubisco small subunit (SSU) gene terminator sequences, subclover stunt virus (SCSV) gene sequence terminators, any rho-independent *E. coli* terminator, amongst others.

Those skilled in the art will be aware of additional promoter sequences and terminator sequences which may be suitable for use in performing the invention. Such sequences may readily be used without any undue experimentation.

The genetic constructs of the invention may further include an origin of replication sequence which is required for replication in a specific cell type, for example a bacterial cell, when said genetic construct is required to be maintained as an episomal genetic element (eg. plasmid or cosmid molecule) in said cell.

Preferred origins of replication include, but are not limited to, the fl-ori and colE1 origins of replication.

The genetic construct may further comprise a selectable marker gene or genes that are functional in a cell into which said genetic construct is introduced.

As used herein, the term "selectable marker gene" includes any gene which confers a phenotype on a cell in which it is expressed to facilitate the identification and/or selection of cells which are transfected or transformed with a genetic construct of the invention or a derivative thereof.

Suitable selectable marker genes contemplated herein include the ampicillin resistance ($Amp^r$), tetracycline resistance gene ($Tc^r$), bacterial kanamycin resistance gene ($Kan^r$), phosphinothricin resistance gene, neomycin phosphotransferase gene (nptII), hygromycin resistance gene, β-glucuronidase (GUS) gene, chloramphenicol acetyltransferase (CAT) gene and luciferase gene, amongst others.

A further aspect of the present invention provides a transfected or transformed cell, tissue, organ or whole organism which expresses a recombinant epoxygenase polypeptide or a ribozyme, antisense or co-suppression molecule as described herein, or a homologue, analogue or derivative thereof.

Preferably, the isolated nucleic acid molecule is contained within a genetic construct as described herein. The genetic construct of the present invention may be introduced into a cell by various techniques known to those skilled in the art. The technique used may vary depending on the known successful techniques for that particular organism.

Means for introducing recombinant DNA into bacterial cells, yeast cells, or plant, insect, fungal (including mould), avian or mammalian tissue or cells include, but are not limited to, transformation using $CaCl_2$ and variations thereof, in particular the method described by Hanahan (1983), direct DNA uptake into protoplasts (Krens et al, 1982; Paszkowski et al, 1984), PEG-mediated uptake to protoplasts (Armstrong et al, 1990) microparticle bombardment, electroporation (Fromm et al., 1985), microinjection of DNA (Crossway et al., 1986), microparticle bombardment of tissue explants or cells (Christou et al, 1988; Sanford, 1988), vacuum-infiltration of tissue with nucleic acid, or in the case of plants, T-DNA-mediated transfer from Agrobacterium to the plant tissue as described essentially by An et al. (1985), Herrera-Estrella et al. (1983a, 1983b, 1985).

For microparticle bombardment of cells, a microparticle is propelled into a cell to produce a transformed cell. Any suitable ballistic cell transformation methodology and apparatus can be used in performing the present invention. Exemplary apparatus and procedures are disclosed by Stomp et al. (U.S. Pat. No. 5,122,466) and Sanford and Wolf (U.S. Pat. No. 4,945,050). When using ballistic transformation procedures, the genetic construct may incorporate a plasmid capable of replicating in the cell to be transformed.

Examples of microparticles suitable for use in such systems include 1 to 5 µm gold spheres. The DNA construct may be deposited on the microparticle by any suitable technique, such as by precipitation.

In a particularly preferred embodiment, wherein the genetic construct comprises a "sense" molecule, it is particularly preferred that the recombinant epoxygenase polypeptide produced therefrom is enzymatically active.

Alternatively, wherein the cell is derived from a multi-cellular organism and where relevant technology is available, a whole organism may be regenerated from the transformed cell, in accordance with procedures well known in the art.

Those skilled in the art will also be aware of the methods for transforming, regenerating and propagating other type of cells, sucl. as those of fungi.

In the case of plants, plant tissue capable of subsequent clonal propagation, whether by organogenesis or embryogenesis, may be transformed with a genetic construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem).

The term "organogenesis", as used herein, means a process by which shoots and roots are developed sequentially from meristematic centres.

The term "embryogenesis", as used herein, means a process by which shoots and roots develop together in a concerted fashion (not sequentially), whether from somatic cells or gametes.

The regenerated transformed plants may be propagated by a variety of means, such as by clonal propagation or classical breeding techniques. For example, a first generation (or T1) transformed plant may be selfed to give homozygous second generation (or T2) transformant, and the T2 plants further propagated through classical breeding techniques.

The regenerated transformed organisms contemplated herein may take a variety of forms. For example, they may be chimeras of transformed cells and non-transformed cells; clonal transformants (e.g., all cells transformed to contain the expression cassette); grafts of transformed and untransformed tissues (e.g., in plants, a transformed root stock grafted to an untransformed scion).

A further aspect of the invention provides a method of altering the level of epoxy fatty acids in a cell, tissue, organ or organism, said method comprising expressing a sense, antisense, ribozyme or co-suppression molecule as described herein in said cell for a time and under conditions sufficient for the level of epoxy fatty acids therein to be increased or reduced.

In a preferred embodiment, the subject method comprises the additional first step of transforming the cell, tissue, organ or organism with the sense, antisense, ribozyme or co-suppression molecule.

As discussed supra the isolated nucleic acid molecule may be contained within a genetic construct.

According to this embodiment, the cell, organ, tissue or organism in which the subject sense, antisense, ribozyme or co-suppression molecule is expressed may be derived from a bacteria, yeast, fungus (including a mould), insect, plant, bird or mammal.

Because a recombinant epoxygenase polypeptide may be produced in the regenerated transformant as well as ex vivo, one alternative preferred embodiment of the present invention provides a method of producing a recombinant enzymatically active epoxygenase polypeptide in a cell, said method comprising the steps of:

(i) producing a genetic construct which comprises the cDNA or genomic epoxygenase genetic sequence of the invention placed operably under the control of a promoter capable of conferring expression on said genetic sequence in said cell, and optionally an expression enhancer element;

(ii) transforming said genetic construct into said cell; and (iii) selecting transformants which express the epoxygenase encoded by the genetic sequence at a high level.

A particularly preferred embodiment of the present invention provides a method of producing a recombinant enzymatically active epoxygenase polypeptide in a transgenic plant comprising the steps of:

(i) producing a genetic construct which comprises the cDNA or genomic epoxygenase genetic sequence of the invention placed operably under the control of a seed-specific promoter and optionally an expression enhancer element, wherein said genetic sequences is also placed upstream of a transcription terminator sequence;

(ii) transforming said genetic construct into a cell or tissue of said plant; and (iii) selecting transformants which express the epoxygenase encoded by the genetic sequence at a high level in seeds.

In a more particularly preferred embodiment, the plant is an oilseed species that normally produces significant levels of linoleic acid, for example Linola® flax, oilseed rape, sunflower, safflower, soybean, linseed, sesame, cottonseed, peanut, olive or oil palm, amongst others.

In an even more particularly preferred embodiment, the plant is an oilseed species that normally produces significant levels of linoleic acid, for example Linola® flax, sunflower or safflower, amongst other.

Enzymatically active recombinant epoxygenases described herein are particularly useful for the production of epoxygenated fatty acids from unsaturated fatty acid substrates. The present invention especially contemplates the production of specific epoxygenated fatty acids in cells or regenerated transformed organisms which do not normally produce that specific epoxygenated fatty acid.

Accordingly, a further aspect of the invention provides a method of producing an epoxygenated fatty acid in a cell, tissue, organ or organism, said method comprising incubating a cell, tissue, organ or organism which expresses an enzymatically active recombinant epoxygenase of the present invention with a fatty acid substrate molecule, preferably an unsaturated fatty acid substrate molecule, for a time and under conditions sufficient for at least one carbon bond of said substrate to be converted to an epoxy group.

In an alternative embodiment, the subject method further comprises the additional first step of transforming or transfecting the cell, tissue, organ or organism with a nucleic acid molecule which encodes said recombinant epoxygenase or a homologue, analogue or derivative thereof, as hereinbefore described. As discussed supra the isolated nucleic acid molecule may be contained within a genetic construct.

According to this embodiment, the cell, organ, tissue or organism in which the subject epoxygenase is expressed is derived from a bacteria, yeast, fungus (including a mould), insect, plant, bird or mammal. More preferably, the cell, organ, tissue or organism is derived from a yeast, plant or fungus, even more preferably from an oleaginous yeast or plant or fungus, or from an oilseed plant which does not normally express the recombinant epoxygenase of the invention.

Amongst the main economic oilseed plants contemplated herein, high-linoleic genotypes of flax, sunflower, corn and safflower are preferred targets. Soybean and rapeseed are alternative targets but are less suitable for maximal epoxy fatty acid synthesis because of their lower levels of linoleic acid substrate and the presence of an active Δ15-desaturase competing with the epoxygenase for the linoleic acid substrate.

An alternative embodiment is the transformation of Linola® (=low linolenic acid flax) with the epoxygenase of the invention. Linola® flax normally contains around 70% linoleic acid with very little of this (<2%) being subsequently converted to linolenic acid by Δ15-desaturase (Green, 1986).

Preferred unsaturated fatty acid substrates contemplated herein include, but are not limited to, palmitoleic acid, oleic acid, linoleic acid, linolenic acid, and arachidonic acid, amongst others.

In plant species that naturally contain high levels of vernolic acid, the Δ12-epoxygenase therein may be very efficient at epoxidising linoleic acid. As a consequence, the present invention particularly contemplates the expression of recombinant Δ12-epoxygenase derived from *Euphorbia lagascae*, Vernonia spp. and Crepis spp. at high levels in transgenic oilseeds during seed oil synthesis, to produce high levels of vernolic acid therein.

Accordingly, linoleic acid is a particularly preferred substrate according to this embodiment of the invention. Additional substrates are not excluded.

The products of the substrate molecules listed supra will be readily determined by those skilled in the art, without undue experimentation. Particularly preferred epoxy fatty acids produced according to the present invention include 12,13-epoxy-9-octadecenoic acid (vernolic acid) and 12,13-epoxy-9,15-octadecadienoic acid, amongst others.

Conditions for the incubation of cells, organs, tissues or organisms expressing the recombinant epoxygenase in the presence of the substrate molecule will vary, at least depending upon the uptake of the substrate into the cell, tissue, organ or organism, and the affinity of the epoxygenase for the substrate molecule in the particular environment selected. Optimum conditions may be readily determined by those skilled in the relevant art.

The present invention clearly extends to the isolated oil containing epoxy fatty acids, and/or the isolated epoxy fatty acid itself produced as described herein and to any products derived therefrom, for example coatings, resins, glues, plastics, surfactants and lubricants, amongst others.

The inventors have shown further that the mixed function monooxygenases (MMO) which perform catalytic functions such as desaturation, acetylenation, hydroxylation and/or epoxygenation, form a family of genes sharing considerable nucleotide and amino acid sequence similarity. For example, the desaturase, acetylenase, hydroxylase and/or epoxygenase enzymes which act on substrate molecules having a similar chain length and position of any carbon double bond(s) (if present) are more closely related to each other than to enzymes acting upon other substrates, and may be considered to be a "family".

Without being bound by any theory or mode of action, the sequence similarity between the members of any gene family has its basis in the identity of the substrate involved and the biochemical similarity of the reaction events occurring at the target carbon bond during the modification reaction, suggesting that divergent sequences within a family may comprise catalytic determinants or at least a functional part thereof which contributes to the specific catalytic properties of the family members.

One example of a family is the desaturase, acetylenase, hydroxylase and/or epoxygenase enzymes which catalyse desaturation, acetylenation, hydroxylation and/or epoxygenation respectively, of the Δ12 position of linoleic acid (hereinafter referred to as the "C18 Δ12-MMO family"). The present inventors have compared the nucleotide and amino acid sequences of members of the C18 Δ12-MMO family to determine the divergent regions thereof which potentially comprise the determinants of alternative catalytic functions at the Δ12 position (hereinafter referred to as "putative catalytic determinants").

Furthermore, the presence of such families of fatty acid modifying MMOs is contemplated with respect to other fatty acid chain length and double bond positions. For example, the C18 Δ15-desaturase is contemplated to belong to a family of related enzymes capable of desaturation, acetylenation, hydroxylation and/or epoxidation of the Δ15 position in C18 fatty acid substrates, the C18 Δ15-MMO family.

By producing synthetic genes in which these catalytic determinants have been interchanged (referred to as "domain swapping") it is possible to convert genes encoding one catalytic function into those encoding alternative catalytic functions. For example, the Δ12 epoxygenase of the instant invention may be converted to a Δ12 acetylenase by replacing portions of its C-terminal and N-terminal sequences with the equivalent domains from the *Crepis alpina* Δ12 acetylenase. Similarly, the reverse domain swapping may also be performed.

As a further refinement, such changes in catalytic function can similarly be effected by making specific changes (e.g. addition, substitution or deletion) to only those amino-acids within each domain that are critical for determining the relevant catalytic function (such as by site-directed mutagenesis).

Accordingly, a further aspect of the present invention contemplates a synthetic fatty acid gene comprising a sequence of nucleotides derived from an epoxygenase gene as described herein, wherein said synthetic fatty acid gene encodes a polypeptide with epoxygenase or acetylenase or hydroxylase or desaturase activity, wherein said polypeptide either comprises an amino acid sequence which differs from a naturally-occurring epoxygenase or acetylenase or hydroxylase or desaturase enzyme, or said polypeptide exhibits catalytic properties which are different from a naturally-occurring epoxygenase or acetylenase or hydroxylase or desaturase enzyme or said polypeptide comprises a sequence of amino acids which are at least about 60% identical to a part of SEQ ID NO: 2 or 4 or 6 or homologue, analogue or derivative of said part.

Preferably, the synthetic fatty acid gene of the invention is derived from a Δ12 epoxygenase gene.

In one embodiment, the synthetic fatty acid gene of the invention encodes a fusion polypeptide in which the N-terminal and/or C-terminal amino acids of any one of SEQ ID NOs: 2 or 4 or 6 are replaced, in-frame, by amino acid sequences of a different member of the same family.

In a particularly preferred embodiment, the N-terminal and/or C-terminal amino acids of SEQ ID NO: 2 or 4 or 6 are replaced by the corresponding regions of the acetylenase, desaturase or hydroxylase polypeptides set forth in FIG. 2. More preferably, at least about 30 amino acid residues from the N-terminal and/or C-terminal regions of any one of SEQ ID NOs: 2 or 4 or 6 are replaced, in-frame, by the corresponding regions of the acetylenase, desaturase or hydroxylase polypeptides set forth in FIG. 2.

In an alternative embodiment, the synthetic fatty acid gene of the invention encodes a fusion polypeptide in which the N-terminal and/or C-terminal amino acids of a fatty acid acetylenase or fatty acid hydroxylase or fatty acid desaturase are replaced, in-frame, by the N-terminal and/or C-terminal region of any one of SEQ ID NOs: 2 or 4 or 6.

In a particularly preferred embodiment, the N-terminal and/or C-terminal amino acids of a fatty acid acetylenase or fatty acid hydroxylase or fatty acid desaturase are replaced, in-frame, by the N-terminal and/or C-terminal region of any one of SEQ ID NOs: 2 or 4 or 6. Even more preferably, the fatty acid acetylenase or fatty acid hydroxylase or fatty acid desaturase is selected from the list set forth in FIG. 2.

Even still more preferably, at least about 30 amino acid residues from the N-terminal and/or C-terminal regions of a fatty acid acetylenase or fatty acid hydroxylase or fatty acid desaturase are replaced, in-frame, by the N-terminal and/or C-terminal region of any one of SEQ ID NOs: 2 or 4 or 6.

Accordingly, the present invention extends to any variants of the epoxygenase enzymes referred to herein, wherein said variants are derived from an epoxygenase polypeptide as described herein and exhibit demonstrable acetylenase or hydroxylase or desaturase activity, and either comprises an amino acid sequence which differs from a naturally-occurring acetylenase or hydroxylase or desaturase enzyme, or exhibit catalytic properties which are different from a naturally-occurring acetylenase or hydroxylase or desaturase enzyme, or comprise a sequence of amino acids which are at least about 60% identical to any one of SEQ ID NOs: 2 or 4 or 6.

As with other aspects of the invention, the variants described herein may be produced as recombinant polypeptides or in transgenic orgarisms, once the subject synthetic genes are introduced into a suitable host cell and expressed therein.

The recombinant polypeptides described herein or a homologue, analogue or derivative thereof, may also be immunologically active molecules.

A further aspect of the present invention provides an immunologically-interactive molecule which is capable of binding to a recombinant epoxygenase polypeptide of the invention.

Preferably, the recombinant epoxygenase polypeptide to which the immunologically-interactive molecule is capable of binding comprises a sequence of amino acids set forth in any one of SEQ ID NOs: 2, 4 or 6, or a homologue, analogue or derivative thereof.

In one embodiment, the immunologically interactive molecule is an antibody molecule. The antibody molecule may be monoclonal or polyclonal. Monoclonal or polyclonal antibodies may be selected from naturally occurring antibodies to an epitope, or peptide fragment, or synthetic epoxygenase peptide derived from a recombinant gene product or may be specifically raised against a recombinant epoxygenase or a homologue, analogue or derivative thereof.

Both polyclonal and monoclonal antibodies are obtainable by immunisation with an appropriate gene product, or epitope, or peptide fragment of a gene product. Alternatively, fragments of antibodies may be used, such as Fab fragments. The present invention extends to recombinant and synthetic antibodies and to antibody hybrids. A "synthetic antibody" is considered herein to include fragments and hybrids of antibodies The antibodies contemplated herein may be used for identifying genetic sequences which express related epoxygenase polypeptides encompassed by the embodiments described herein.

The only requirement for successful detection of a related epoxygenase genetic sequence is that said genetic sequence is expressed to produce at least one epitope recognised by the antibody molecule. Preferably, for the purpose of obtaining expression to facilitate detection, the related genetic sequence is placed operably behind a promoter sequence, for example the bacterial lac promoter. According to this preferred embodiment, the antibodies are employed to detect the presence of a plasmid or bacteriophage which expresses the related epoxygenase. Accordingly, the antibody molecules are also useful in purifying the plasmid or bacteriophage which expresses the related epoxygenase.

The subject antibody molecules may also be employed to purify the recombinant epoxygenase of the invention or a naturally-occurring equivalent or a homologue, analogue or derivative of same.

The present invention is further described by reference to the following non-limiting Examples.

EXAMPLE 1

Characterization of Epoxy Fatty Acids in *Euphorbia lagascae* and Crepis spp.

Seed from the wild species *Euphorbia lagascae* and from various Crepis species were screened by gas liquid chromatography for the presence of epoxy fatty acids.

As shown in Table 3, *Euphorbia lagascae* contains very high levels of the epoxy fatty acid vernolic acid in its seed oil. Seeds from *Crepis palaestrina* were shown to contain 61.4 weight % of vernolic acid and 0.71 weight % of the acetylenic fatty acid crepenynic acid of total fatty acids (Table 3).

TABLE 3

Fatty acid composition of lipids derived from seeds of
*Crepis alpina, Crepis palaestina* and *Euphorbia lagascae*

Relative distribution (weight %)[a]

| Fatty acid | Crepis alpina | Crepis palaestina | Euphorbia lagascae |
|---|---|---|---|
| Palmitic | 3.9 | 5.1 | 4.3 |
| Stearic | 1.3 | 2.3 | 1.8 |
| Oleic | 1.8 | 6.3 | 22.0 |
| Linoleic | 14.0 | 23.0 | 10.0 |
| Crepyninic | 75.0 | 0.7 | 0 |
| Vernolic | 0 | 61.4 | 58.0 |
| Other | 4.0 | 1.2 | 3.9 |

[a]Calculated from the area % of total integrated peak areas in gas liquid chromatographic determination of methyl ester derivatives of the seed lipids

EXAMPLE 2

Biochemical Characterization of Linoleate Δ12-epoxygenases in *Euphorbia lagascae* and *Crepis palaestrina*

The enzyme, linoleate Δ12-epoxygenase synthesizes vernolic acid from linoleic acid. Linoleate Δ12-epoxygenases derived from *Euphorbia lagascae* and *Crepis palaestrina* are ocalized in the microsomes. The enzymes from these species at least can remain active in embrane (microsomal) fractions prepared from developing seeds.

Preparations of membranes from *Euphorbia lagascae* and assays of their epoxygenase activities were performed as described by Bafor et al. (1993) with incubations containing NADPH, unless otherwise indicated in Table 4. Lipid extraction, separation and methylation as well as GLC and radio-GLC separations were performed essentially as described by Kohn et al. (1994) and Bafor et al. (1993).

Preparations of membranes from *Crepis alpina* and *Crepis palaestrina* were obtained as follows. *Crepis alpina* and *Crepis palaestrina* plants were grown in green houses and seeds were harvested at the mid-stage of development (17–20 days after flowering). Cotyledons were squeezed out from their seed coats and homogenised with mortar and pestle in 0.1M phosphate buffer, pH 7.2 containing 0.33M sucrose, 4 mM NADH, 2 mM CoASH, 1 mg of bovine serum albumin/ml and 4,000 units of catalase/ml. The homogenate was centrifuged for 10 min at 18,000×g and the resulting supernatant centrifuged for 60 min at 150,000×g to obtain a microsomal pellet.

Standard desaturase, acetylenase and epoxygenase assays with microsomal membranes from Crepis species were performed at 25° C. with microsomal preparations equivalent to 0.2 mg microsomal protein resuspended in fresh homogenisation buffer and 10 nmol of either [1-$^{14}$C]18:1-CoA or [1-$^{14}$C]18:2-CoA (specific activity 85,000 d.p.m./nmol) in a total volume of 360 μl. When NADPH was used as coreductant, the membranes were resuspended in homogenisation buffer where NADH had been replaced by NADPH.

Biochemical characterisation of the microsomal linoleate Δ12-epoxygenase derived from *Euphorbia lagascae* and *Crepis palaestrina* was carried out and data obtained were compared to the biochemical characteristics of oleate Δ12-desaturase and linoleate Δ12-acetylenase enzymes derived from microsomal preparations of *Crepis alpina* (Table 4).

As shown in Table 4, the *Crepis palaestrina* linoleate Δ12-epoxygenase exhibits similar biochemical features to the linoleate Δ12-acetylenase and oleate Δ12-desaturase from *Crepis alpina*, in so far as all three enzymes require $O_2$, work equally well with either NADH or NADPH as the coreductants, and are inhibited by cyanide but not by carbon monoxide. Additionally, none of these enzymes are inhibited by monoclonal antibodies against cytochrome P450 reductase.

The data in Table 4 suggest that the *Crepis palaestrina* linoleate Δ12-epoxygenase belongs to the same class of enzyme as the *Crepis alpina* microsomal oleate Δ12-desaturase and linoleate Δ12-acetylenase.

In contrast, the *Euphorbia lagascae* linoleate Δ12-epoxygenase requires NADPH as the coreductant, is not inhibited by cyanide, but is inhibited by carbon monoxide (Table 4). Additionally, the inventors have discovered that the *Euphorbia lagascae* linoleate Δ12-epoxygenase is inhibited by monoclonal antibodies raised against a cytochrome P450 reductase enzyme. These data suggest that the *Euphorbia lagascae* linoleate Δ12-epoxygenase belongs to the cytochrome P450 class of proteins and is therefore not related biochemically to the *Crepis palaestrina* linoleate Δ12-epoxygenase.

TABLE 4

Comparison of the biochemical characteristics of epoxygenases, acetylenases and desaturases derived from *Crepis spp.* and *Euphorbia lagascae*

Enzyme Activity (% of control)

| Treatment | C. alpina oleate Δ12-desaturase | C. alpina linoleate Δ12-acetylenase | C. palaestina linoleate Δ12-epoxygenase | E. lagascae linoleate Δ12-epoxygenase |
|---|---|---|---|---|
| Carbon monoxide | 85 | 84 | 88 | 3 |
| Anti-P450 reductase antibodies ($C_5A_5$) | 96 | 91 | 94 | 33 |
| KCN | 16 | 0 | 35 | 92 |
| minus NADH plus NADPH | 95 | 73 | 94 | 100 (control) |
| minus NADPH plus NADH | 100 (control) | 100 (control) | 100 (control) | 11 |

EXAMPLE 3

Strategy for Cloning *Crepis palaestrina* Epoxygenase Genes

Cloning of the *Crepis palaestrina* epoxygenase genes relied on the characteristics of the *C. palaestina* and *C. alpina* enzymes described in the preceding Examples.

In particular, poly (A)+ RNA was isolated from developing seeds of *Crepis palaestina* using a QuickPrep Micro mRNA purification kit (Pharmacia Biotechnology) and used to synthesise an oligosaccharide d(T)-primed double stranded cDNA. The double stranded cDNA was ligated to EcoRI/NotI adaptors (Pharmacia Biotechnology) and a cDNA library was constructed using the ZAP-cDNA Gigapack cloning kit (Stratagene).

Single-stranded cDNA was prepared from RNA derived from the developing seeds of *Crepis alpina*, using standard procedures. A PCR fragment, designated as D12V (SEQ ID NO:7), was obtained by amplifying the single-stranded cDNA using primers derived from the deduced amino acid sequences of plant mixed-function monooxygenases.

The D12V fragment was subsequently random-labelled and used to screen the *Crepis palaestina* cDNA library supra on Hybond N+ membrane filters from Amersham as prescribed by the manufacturer using standard hybridization conditions. This approach resulted in the purification of a recombinant bacteriophage, designated Cpal2.

The nucleotide sequence of the Cpal2 cDNA was determined and is set forth in SEQ ID NO: 1.

The Cpal2 cDNA appeared to be full-length. A schematic representation of an expression vector comprising the Cpal2 cDNA is presented in FIG. 1. The genetic construct set forth therein is designed for introduction into plant material for the production of a transgenic plant which expresses the subject epoxygenase. Those skilled in the art will recognise that similar expression vectors may be produced, without undue experimentation, and used for the production of transgenic plants which express any of the genetic sequences of the instant invention, by replacing the Cpal2 cDNA with another structural gene sequence.

As shown in FIG. 2, the nucleotide sequence of the Crep1 cDNA encoded a polypeptide which was closely related at the amino acid level, at least, to an acetylenase enzyme of *C. alpina* (Bafor et al. 1997; International Patent Application No. PCT/SE97/00247).

The 1.4 kb insert from pCpal2 was sequenced (SEQ ID NO. 1) and shown to comprise an open reading frame which encodes a polypeptide of 374 amino acids in length. The deduced amino acid sequence of Cpal2 showed 81% identity and 92% similarity to the Δ12-acetylenase from *Crepis alpina* and approximately 60% identity and 80% similarity with plant microsomal Δ12-desaturase proteins (FIG. 2). However, the polypeptide encoded by Cpal2 comprised significant differences in amino acid sequence compared to non-epoxygenase enzymes. In particular, the Cpal2 has a deletion of six contiguous amino acids in the 5' terminal region compared to all the microsomal Δ12 desaturases, and a deletion of two contiguous amino acids in the 3' terminal region compared to the Crep1 Δ12 acetylenase (FIG. 2).

Although membrane-bound fatty acid desaturase genes show limited sequence homologies, they all contain three regions of conserved histidine-rich motifs as follows:

(i) His-(Xaa)$_{3-4}$-His;

(ii) His-(Xaa)$_{2-3}$-His-His; and (iii) His-(Xaa)$_{2-3}$-His-His, wherein His designates histidine, Xaa designates any naturally-occurring amino acid residue as set forth in Table 1 herein, the integer (Xaa)$_{3-4}$ refers to a sequence of amino acids comprising three or four repeats of Xaa, and the integer (Xaa)$_{2-3}$ refers to a sequence of amino acids comprising two or three repeats of Xaa. These histidine-rich regions are suggested to be a part of the active centre of the enzyme (Shanklin et al., 1994).

The amino acid sequence encoded by the Cpal2 cDNA comprises three histidine-rich motifs similar, but not identical, to the histidine-rich motifs of the Δ12-desaturase enzymes. These data suggest that the Cpal2 cDNA encodes an enzyme which belongs to the mixed function monooxygenase class of enzymes.

Figure 3:
FIG. 3 is a copy of a photographic representation of a northern blot hybridization showing seed-specific expression of the *Crepis palaestrina* epoxygenase gene exemplified by SEQ ID NO:1. Northern blot analysis of total RNA from leaves (lane 1) and developing seeds (lane 2)of *Crepis palaestrina*. 15 μg of total RNA was run on a Northern gel and blotted onto Hybond N+ membrane from Amersham according to the manufacturer's instructions. The blot was hybridized at 60° C. with a probe made from the 3' untranslated region of SEQ ID NO: 1. The blot was washed twice in 2×SSC (NaCl-Sodium Citrate buffer) at room temperature for 10 minutes, then in 0.1×SSC at 60° C. for 20 min.

The analysis of fatty acids presented in Example 1 supra indicated that vernolic acid was at least present in the seeds of *Crepis palaestrina*. This enzyme may in fact be present exclusively in the seeds of *C. palaestina*. The expression of the Cpal2 gene was examined using the 3' untranslated region of the Cpal2 cDNA clone as a hybridisation probe on northern blots of mRNA derived from developing seeds and leaves of *C. palaestina*. As shown in FIG. 3, the Cpal2 gene was highly-expressed in developing seeds but no expression could be detected in leaves. These data are consistent with the enzyme activity profile of *C. palaestina* linoleate Δ12-epoxygenase in these tissues.

EXAMPLE 4

Strategy for Cloning *Euphorbia lagascae* Epoxygenase Genes

Cloning of the *Euphorbia lagascae* epoxygenase genes relied on the characteristics of the *E. lagascae* enzymes as described in the preceding Examples.

In one approach taken to clone *Euphorbia lagascae* epoxygenase genes, RNA was collected from immature embryos of *Euphorbia lagascae* taken at a stage of active vernolic acid synthesis and used to construct a cDNA library. The cDNA library was constructed in the Lambda Zap II vector (Stratagene) as described in the preceding Example, with the exception that the cDNA inserts were cloned in a directional manner into EcoRI-XhoI sites of the plasmid vector embedded in the lambda vector.

The degenerate PCR primer set forth in FIG. 4 (SEQ ID NO:18)was synthesised and used to amplify nucleotide sequences which encode P450 enzyme sequences from the *Euphorbia lagascae* cDNA library. For PCR amplification reactions, an aliquot 100 μl of the cDNA library was extracted with phenol:chloroform [1:1(v/v)] and DNA was precipitated by the addition of 2 volumes of ethanol and finally resuspended in 100 μl of water. An aliquot (1 μl) of the resuspended DNA was used as template in a PCR amplification reaction. PCR reactions were performed in 10 μl of TaqI polymerase buffer containing 200 μM of each dNTP, 10 pmol of the degenerate primer, 1 pmol of T7 polymerase promoter primer and 0.4 units of TaqI polymerase.

The amplification conditions were 2 min at 94° C., and five cycles, each cycle comprising 1 min at 48° C. followed by 2 min at 72° C. followed by 30 sec at 93° C., then 28 cycles, each cycle comprising 30 sec at 55° C. followed by 90 sec at 72° C. followed by 30 sec at 93° C., and finally one cycle comprising 30 sec at 55° C. followed by 10 min at 72° C. followed by 1 min at 25° C.

PCR products were purified and digested using EcoRI and XhoI, and then sub-cloned into Bluescript vector for sequence characterisation. One of the PCR clones was found to encode a P450 sequence and was used as a probe to isolate a full-length cDNA clone. This nucleotide sequence is set forth in SEQ ID NO: 19. SEQ ID NO: 19 had similarity to other members of the 2C family of P450 genes. In particular, SEQ ID NO:19 shows on average a 40% identity to the human and rat arachidonic epoxygenase sequences using the BLAST program.

Additionally, the SEQ ID NO:19 transcript was shown to be expressed in seeds of *Euphorbia lagascae* but not in roots or leaves (FIG. 5B). The SEQ ID NO:19 transcript was detected in the developing seeds of *Vernonia galamensis* but not in those of *E. cyparissis* or flax, two species that do not produce epoxy fatty acids (FIGS. 5A and 5B).

In an alternative approach taken to clone *Euphorbia lagascae* epoxygenase genes, subtractive hybridization strategy was employed to isolate genes that are specifically expressed in an organism which produces high levels of epoxy fatty acids.

Figure 6:
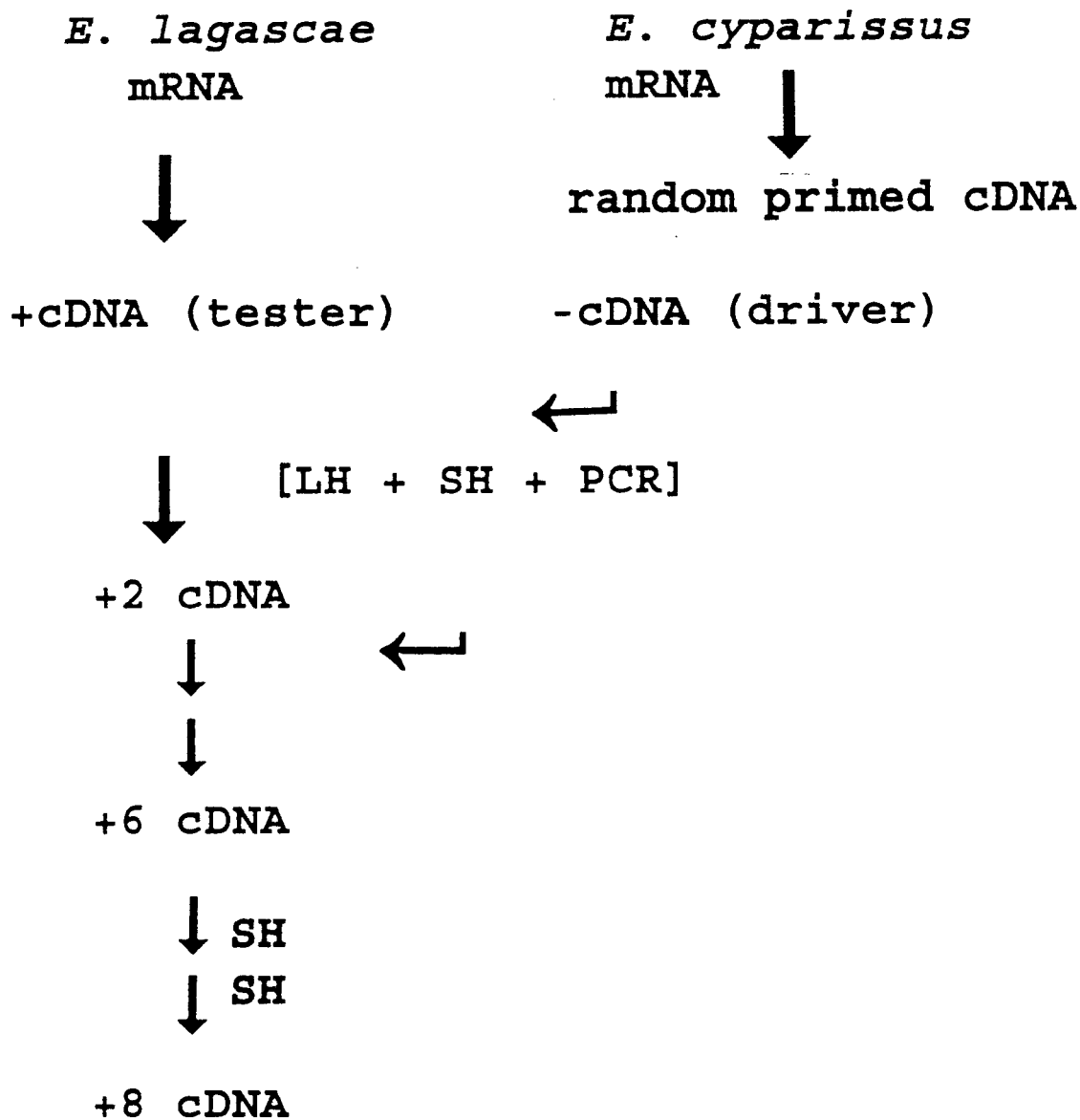
FIG. 6 is a schematic representation showing the subtractive hybridization method used to isolate the *Euphorbia lagascae* epoxygenase genes described herein. The +6cDNA pool consisted predominantly of seed storage protein-like sequences. A pool of 15 such sequences were biotinylated and further subtracted from the +6cDNA. LH=Long Hybridisation −20 hrs; SH=Short Hybridisation −3 hrs.

In particular, the subtractive hybridization method described in FIG. 6 was employed to isolate epoxygenase genes which are expressed specifically in *Euphorbia*

*lagascae*, which produces high levels of the epoxy fatty acid, vernolic acid (Example 1) and not in the closely related species *Euphorbia cyparissus*, which does not produce vernolic acid.

Accordingly, mRNA was isolated from developing embryos of *Euphorbia lagascae* at a stage where they are actively synthesising vernolic acid and used to generate so-called "tester" cDNA. Additionally, mRNA was isolated from the developing embryos of *E. cyparissis* (at a similar stage of development to *E. lagascae*) and used to generate so-called "driver" cDNA.

The subtractive hybridization procedure led to a library which was enriched for sequences exclusively expressed in *Euphorbia lagascae*. Clones from this library were sequenced and at least two sequences were identified as encoding P450 proteins based on similarity to other P450 sequences in the database. These two P450 PCR clones were used as probes to isolate the corresponding full length cDNA clones from the cDNA library referred to earlier.

One of the isolated P450 cDNAs, comprising the sequence of nucleotides set forth in SEQ ID NO:20, appeared to be expressed in tissues of *Euphorbia lagascae* (FIG. 7B) and no homologous transcripts were detected in seed tissue of *E. cyparrisus* or flax, two species that do not produce epoxy fatty acids. The deduced amino acid sequence of SEQ ID NO:20 indicates that the cDNA clone is full-length and encodes a P450 enzyme. These data suggest that the cDNA exemplified by SEQ ID NO:20 may encode an expoxygenase, for example the linoleate Δ12-epoxygenase which converts liroleic acid to vernolic acid.

EXAMPLE 5

Demonstration of Epoxygenase Activity

Confirmation that the cDNA clones exemplifying the invention encode epoxygenase activities was obtained by transforming *Arabidopsis thaliana*, which does not produce epoxy fatty acids, in particular vernolic acid, with each individual candidate clone and examining transformed tissue for the presence of epoxygenated fatty acids which they would not otherwise produce, or for hydroxy fatty acids which might be formed from the metabolism of an epoxygenated fatty acid by the action of endogenous epoxide hydrolases (Blee and Schuber, 1990).

Figure 8:
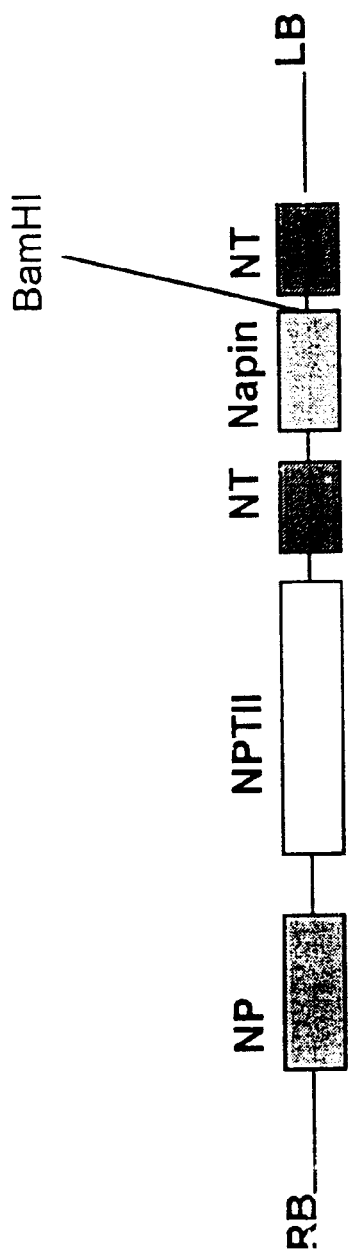
FIG. 8 is a schematic representation of a binary plasmid vector containing an expression cassette which comprises the truncated napin seed-specific promoter (Napin) and nopaline synthase terminator (NT), with a BamHI cloning site there between, in addition to the kanamycin-resistance gene NPTII operably connected to the nopaline synthase promoter (NP) and nopaline synthase terminator (NT) sequences. The expression cassette is flanked by T-DNA left border (LB) and right-border (RB) sequences.

The epoxygenase cDNA comprising SEQ ID NO:1 was cloned into the Binary vector construct set forth in FIG. 8. Briefly, the CDNA sequence was sub-cloned from the pCpal2 plasmid (FIG. 1) into the binary plasmid, by digesting pCpal2 with EcoRI and end-filling the restriction fragment using T4 DNA polymerase enzyme. The Binary vector (FIG. 8) was linearised using BamHI and also end-filled using T4 DNA polymerase. For the end-filling reactions, 1 μg of cDNA insert or linearised Binary vector DNA was resuspended in 50 μl of T4 DNA polymerase buffer (33 mM Tris-acetate pH 7.9, 66 mM potassium acetate, 10 mM magnesium acetate and 5 mM DDT) supplemented with 100 mM of each dNTP and 0.1 mg/ml BSA and 3 units of T4 DNA polymerase, and incubated for 6 min incubation at 37° C. The reaction was stopped by heating at 75° C. for 10mins. The blunt-ended cDNA and Binary vector DNA were ligated using T4 DNA ligase and standard ligation conditions as recommended by Promega. Clones were selected in which the SEQ ID NO: 1 sequence was inserted behind the napin promoter, in the sense orientation, thereby allowing for expression of the epoxygenase polypeptide. The Binary plasmid harbouring SEQ ID NO: 1, in the sense orientation, operably under control of the truncated napin promoter, is represented schematically in FIG. 9.

Figure 9:
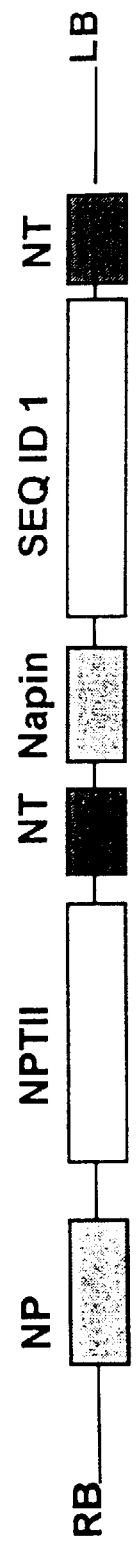
FIG. 9 is a schematic representation of a binary plasmid vector containing an expression cassette which comprises SEQ ID NO: 1 placed operably under the control of a truncated napin seed-specific promoter (Napin) and upstream of the nopaline synthase terminator (NT), in addition to the kanamycin-resistance gene NPTII operably connected to the nopaline synthase promoter (NP) and nopaline synthase terminator (NT) sequences. The expression cassette is flanked by T-DNA left border (LB) and right-border (RB) sequences. To produce this construct, SEQ ID NO: 1 is inserted into the BamHI site of the binary vector set forth in FIG. 8.

The Binary plasmid set forth in FIG. 9 was transformed into Agrobacterium strain AGLI using electroporation and used to transform *Arabidopsis thaliana*. Transgenic *A. thaliana* plants were obtained according to the method described by Valvekens et al. (1988) and Dolferus et al. (1994).

Figure 10A:
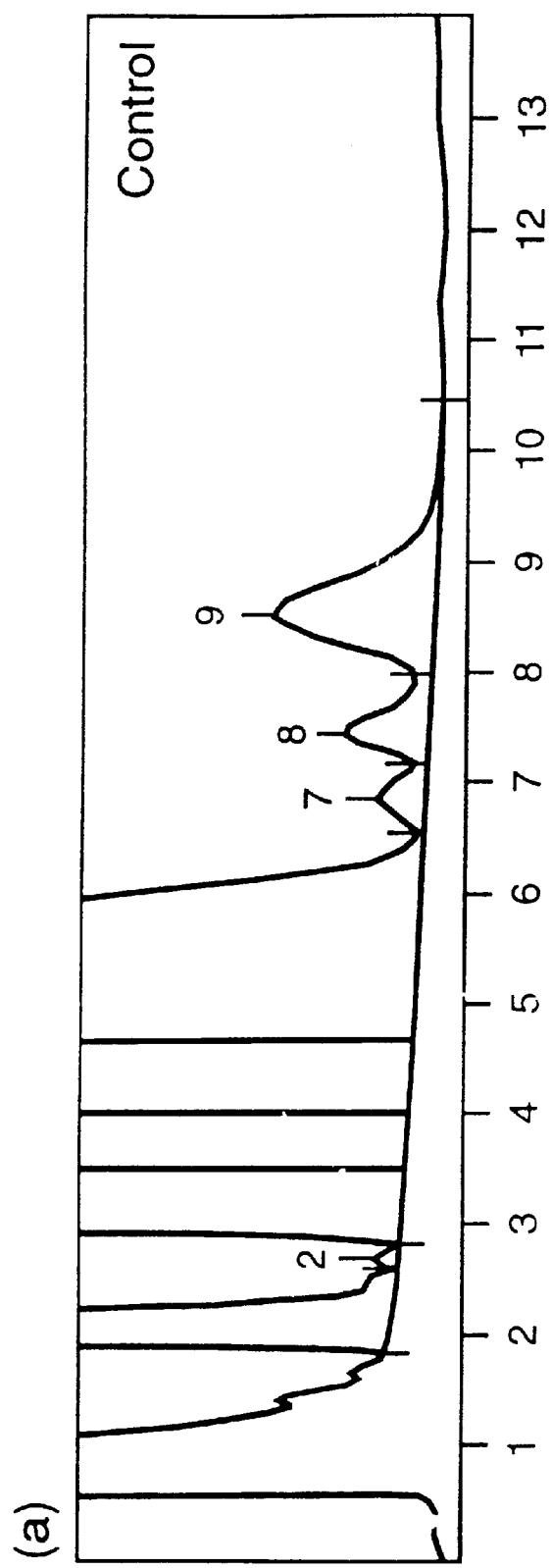
FIGS. 10A–10C are a graphical representation of gas-chromatography traces of fatty acid methyl esters prepared from oil seeds of untransformed *Arabidopsis thaliana* plants [FIG. 10A], or *A. thaliana* plants (transgenic line Cpal-17) which have been transformed with SEQ ID NO:1 using the genetic construct set forth in FIG. 9 [FIGS. 10B and 10C]. In panels (a) and (b), fatty acid methyl esters were separated using packed column separation. In panel (c), the fatty acid methyl esters were separated using capillary column separation. The elution positions of vernolic acid are indicated.
Figure 10B:
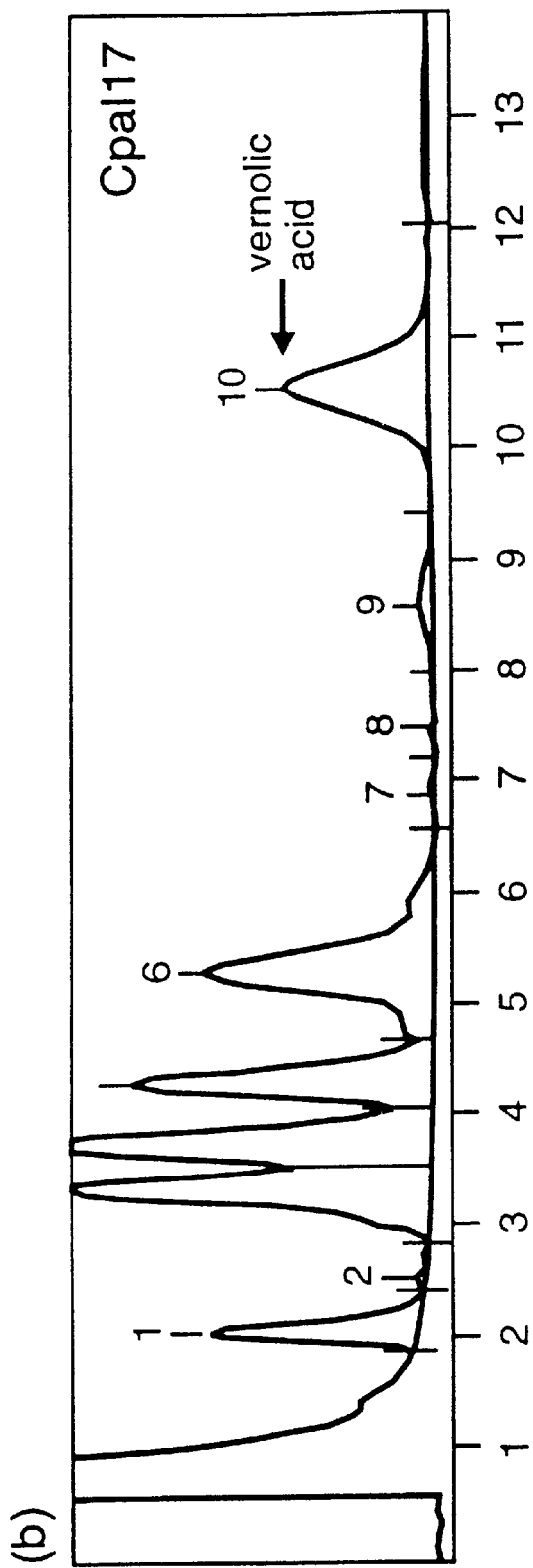
Figure 10C:
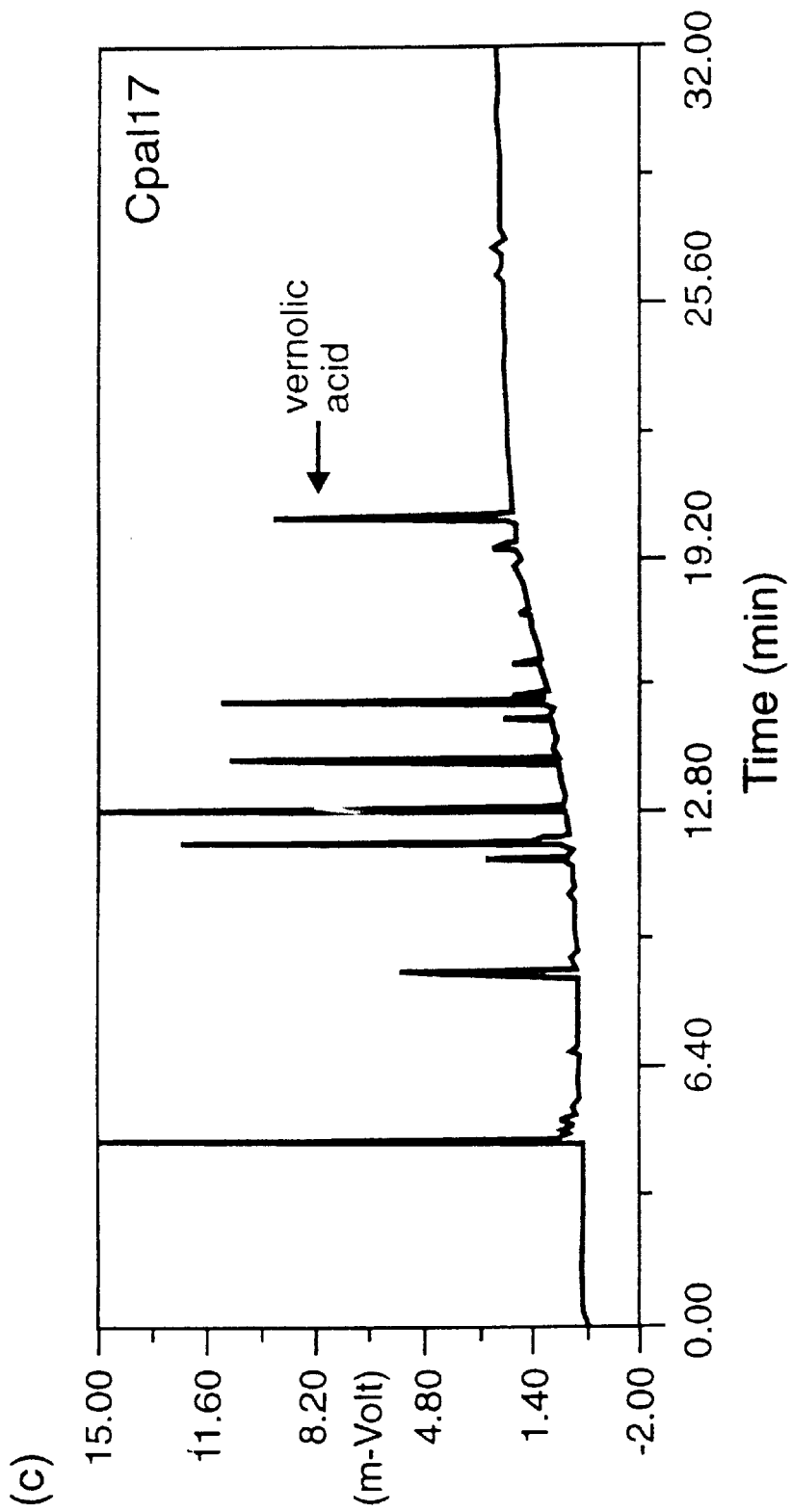

Transgenic plants and untransformed (i.e. control) plants were grown to maturity. Mature seed of each plant was analysed for fatty acid composition by standard techniques. Primary transformant ($T_0$) plants were established and T1 seed was harvested from each plant and analysed for fatty acid composition by gas chromatography. Twelve $T_0$ plants were shown to contain vernolic acid in their T1 seed lipids at concentrations ranging from 0.9% to 15.8% of total fatty acids, while untransformed control plants contained no vernolic acid (Table 5). The highest-expressing plant line was Cpal-17, for which the GLC elution profiles (from packed column and capillary column analysis) is presented in FIG. 10. The GLC elution profile from packed column for the untransformed control is also shown in FIG. 10.

TABLE 5

Vernolic acid levels in transgenic *A. thaliana* lines expressing SEQ ID NO:1

| $T_0$ Plant No. | Vernolic acid (weight % of total seed fatty acids) |
|---|---|
| Cpal-4 | 1.4 |
| Cpal-5 | 1.1 |
| Cpal-8 | 2.7 |
| Cpal-9 | 0.9 |
| Cpal-13 | 0.9 |
| Cpal-15 | 1.1 |
| Cpal-17 | 15.8 |
| Cpal-21 | 1.3 |
| Cpal-23 | 1.4 |
| Cpal-24 | 1.0 |
| Cpal-25 | 1.2 |
| Cpal-26 | 1.1 |
| untransformed control line | 0.0 |

Alternatively, or in addition, putative fatty acid epoxygenase sequences described herein are each transformed into *Linum usitatissimum* (flax) and *Arabidopsis thaliana* under the control of the napin seed-specific promoter. Transgenic flax and *Arabidopsis thaliana* plants are examined for presence of epoxy fatty acids in developing seed oils. Previous work has shown that if epoxy fatty acids are fed to developing flax embryos they are incorporated into triglycerides (Example 10).

Alternatively, yeast are also transformed with the epoxygenase clones of the invention and assayed for production of epoxy fatty acids.

EXAMPLE 6

Mass Spectroscopy Confirmation of Epoxy Fatty Acids in $T_1$ Arabidopsis Seed Borne on Primary $T_0$ Transgenic Plants Gas chromatography of methyl esters prepared from seed lipids of T1 seed of Cpal2-transformed *Arabidopsis thaliana* plants (Example 5) revealed the presence of two additional fatty acids compared to the untransformed controls. The first of these compounds had a retention time equivalent to that of a vernolic acid standard. The second compound had a longer retention time and was putatively identified as 12,13-epoxy-9,15-octadecadienoic acid, an expected derivative of vernolic acid, resulting from desaturation at the Δ15 position by the endogenous *Arabidopsis thaliana* Δ15-desaturase.

Confirmation of the exact identity of the two peaks was obtained by mass spectroscopy of diols which were prepared from the epoxy fatty acid fraction derived from Cpal2-transformed plants. The diols were converted further to trimethylsilyl ethers and analysed by GC-MS DB23 on a fused silica capillary column (Hewlett-Packard 5890 II GC coupled to a Hewlett Packard 5989A MS working in electron impact at 70eV15). The total ion chromatogram showed two peaks as follows:

(i) The first eluting peak had prominent ions of mass 73, 172, 275, and 299, indicating that the epoxy group was positioned at C-12 of a C18 fatty acid and that a double bond occurred between the epoxy group and the carboxyl terminus. This mass spectra was identical to the spectra of a trimethylsilyl ether derivative of diols prepared from pure vernolic acid (12,13-epoxy-9-octadecenoic acid); and (ii) The second eluting peak had prominent ions of mass 73, 171, 273, and 299, indicating the presence of two double bonds and an epoxy group positioned at C-12 of a C18 fatty acid, consistent with the mass spectrum for 12,13-epoxy-9,15-octadecadienoic acid.

EXAMPLE 7

Fatty Acid Analysis of Cpal2 Transgenic Arabidopsis Plants

The T1 seed derived from transformed *Arabidopsis thaliana* plants expressing the Cpal2 cDNA clone under control of the napin promoter was germinated and T1 plants were established from five To lines (Nos. 4, 8, 13, 17 & 21 in Table 5). The T2 seed was harvested from each T1 plant and analysed for fatty acid composition. The progeny of transformant Nos. 4, 8, 13 and 21 (Table 5) segregated as expected for presence of vernolic acid, with those plants containing vernolic acid ranging up to 3.1 % (Table 6).

Figure 11:
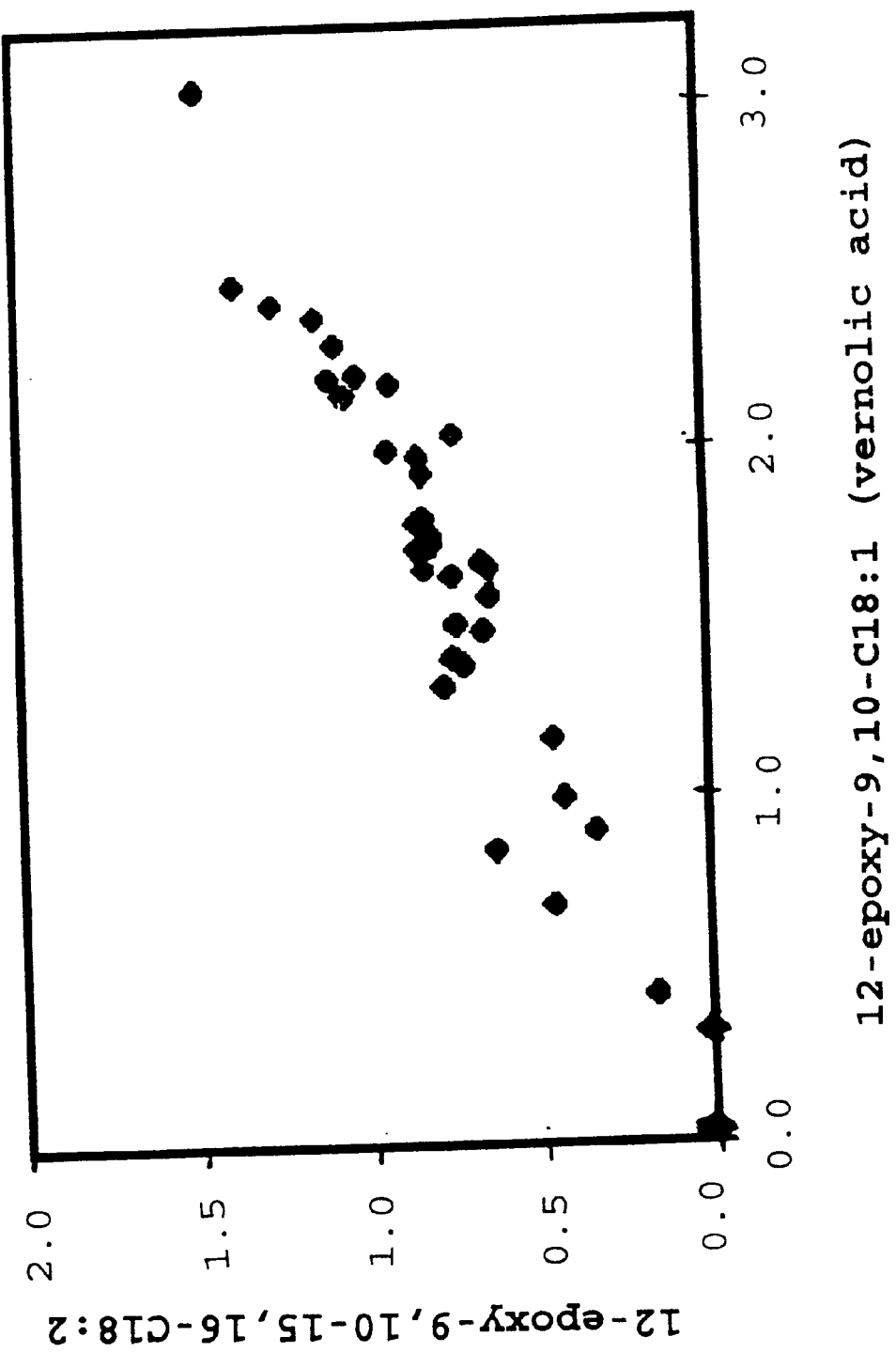
FIG. 11 is a graphical representation showing the joint distribution of epoxy fatty acids in selfed seed on T₁ plants of Cpal-12-transformed *Arabidopsis thaliana* plants as determined using gas chromatography. Levels of both vernolic acid (x-axis) and 12,13-epoxy-9,15-octadecadienoic acid (y-axis) were determined and plotted relative to each other. Data show a positive correlation between the levels of these fatty acids in transgenic plants.

All T1 plants that contained vernolic acid (i.e. epoxy 18:1 in Table 6) also contained 12,13-epoxy-9,15-octadecadienoic acid (i.e. epoxy 18:2 in Table 6; see also FIG. 11), indicating that some of the vernolic acid synthesised by the Cpal2 epoxygenase was subsequently desaturated by the endogenous Δ15-desaturase.

TABLE 6

Fatty acid composition of selfed seeds borne on $T_1$ plants derived from five primary Cpal2 transformants of *Arabidopsis thaliana*

| Plant No. | Non-epoxy fatty acids | | | | | | | | | Epoxy fatty acids | |
|---|---|---|---|---|---|---|---|---|---|---|---|
| | 16:0 | 18:0 | 18:1 | 18:2 | 18:3 | 20:0 | 20:1 | 22:0 | 22:1 | 18:1 | 18:2 |
| 4-1 | 8.3 | 3.9 | 15.5 | 23.9 | 20.6 | 2.8 | 16.5 | 1.7 | 1.6 | — | — |
| 4-2 | 7.6 | 4.1 | 20.3 | 17.8 | 18.0 | 3.4 | 19.7 | 1.8 | 2.0 | 0.82 | 0.63 |
| 4-3 | 8.4 | 4.3 | 26.0 | 13.5 | 16.1 | 2.8 | 19.0 | 1.8 | 1.6 | 2.03 | 0.72 |
| 4-4 | 7.6 | 4.0 | 25.2 | 14.3 | 16.0 | 2.8 | 19.8 | 2.1 | 1.7 | 1.99 | 0.92 |
| 4-5 | 7.2 | 3.6 | 15.6 | 23.1 | 19.9 | 3.1 | 19.7 | 1.6 | 2.1 | — | — |
| 4-6 | 7.0 | 3.7 | 19.2 | 17.8 | 18.4 | 3.2 | 20.3 | 1.9 | 2.1 | 0.87 | 0.33 |
| 4-8 | 7.4 | 3.9 | 16.0 | 23.6 | 20.1 | 3.1 | 18.7 | 1.6 | 1.8 | — | — |
| 4-9 | 7.6 | 4.0 | 24.8 | 13.4 | 15.9 | 2.8 | 20.4 | 2.3 | 1.8 | 2.30 | 1.07 |
| 4-10 | 7.6 | 4.2 | 24.0 | 13.5 | 16.2 | 3.1 | 20.4 | 1.9 | 1.8 | 1.97 | 0.83 |
| 4-11 | 7.4 | 3.9 | 15.0 | 23.2 | 20.4 | 3.3 | 18.8 | 1.7 | 2.0 | — | — |
| 4-12 | 8.7 | 4.0 | 20.7 | 17.0 | 17.5 | 2.6 | 17.2 | 1.7 | 1.5 | 1.38 | 0.74 |
| 4-13 | 7.2 | 4.1 | 21.9 | 16.4 | 17.7 | 3.2 | 21.0 | 1.7 | 1.9 | 1.14 | 0.45 |
| 8-1 | 8.1 | 3.9 | 26.1 | 15.0 | 16.0 | 2.6 | 19.5 | 2.0 | 1.6 | 1.79 | 0.82 |
| 8-3 | 8.7 | 4.2 | 31.6 | 11.5 | 14.0 | 2.2 | 18.5 | 1.9 | 1.4 | 2.38 | 1.13 |
| 8-4 | 8.5 | 4.1 | 27.2 | 15.1 | 16.1 | 2.5 | 18.9 | 1.8 | 1.4 | 1.70 | 0.84 |
| 8-5 | 9.1 | 4.2 | 27.7 | 14.7 | 16.2 | 2.4 | 18.3 | 1.7 | 1.5 | 1.70 | 0.82 |
| 8-6 | 9.8 | 4.0 | 26.0 | 17.2 | 17.2 | 2.3 | 16.9 | 1.6 | 1.2 | 1.36 | 0.71 |
| 8-7 | 10.0 | 3.5 | 15.2 | 25.3 | 22.3 | 2.3 | 14.4 | 1.7 | 1.7 | — | — |
| 8-8 | 8.4 | 4.3 | 32.2 | 10.7 | 13.3 | 2.5 | 20.3 | 1.6 | 1.5 | 1.92 | 0.82 |
| 8-9 | 9.8 | 3.6 | 15.9 | 25.3 | 22.0 | 2.4 | 14.5 | 1.6 | 1.3 | — | — |
| 8-10 | 7.5 | 3.9 | 24.4 | 15.9 | 15.8 | 2.8 | 20.2 | 2.2 | 1.8 | 1.70 | 0.82 |
| 8-11 | 7.6 | 3.8 | 15.4 | 23.6 | 19.8 | 2.9 | 19.4 | 1.5 | 1.8 | — | — |
| 8-12 | 9.4 | 3.7 | 24.2 | 16.7 | 16.7 | 2.2 | 17.6 | 0.9 | 1.2 | 1.46 | 0.65 |
| 8-13 | 10.3 | 4.3 | 25.3 | 17.1 | 17.9 | 2.2 | 16.0 | 1.8 | 1.3 | 1.48 | 0.73 |
| 13-1 | 7.0 | 4.3 | 33.3 | 8.1 | 11.1 | 2.7 | 23.1 | 1.7 | 1.6 | 2.42 | 1.26 |
| 13-2 | 7.2 | 4.3 | 30.4 | 9.6 | 12.7 | 2.8 | 22.0 | 1.8 | 1.6 | 2.48 | 1.37 |
| 13-3 | 7.6 | 3.9 | 15.6 | 23.6 | 19.7 | 3.0 | 19.1 | 1.7 | 1.8 | — | — |
| 13-4 | 7.7 | 4.0 | 15.2 | 22.5 | 19.3 | 3.1 | 18.0 | 1.6 | 1.7 | — | — |
| 13-5 | 8.0 | 4.2 | 16.3 | 22.2 | 17.5 | 4.4 | 19.4 | 2.0 | 2.0 | — | — |
| 13-6 | 7.9 | 4.4 | 25.7 | 14.7 | 15.8 | 2.9 | 21.2 | 1.6 | 1.7 | 1.56 | 0.63 |
| 13-7 | 7.9 | 4.0 | 16.0 | 23.3 | 19.6 | 3.0 | 19.1 | 1.6 | 1.8 | — | — |
| 13-9 | 8.0 | 4.0 | 16.1 | 23.6 | 20.0 | 2.9 | 18.7 | 1.6 | 1.6 | — | — |
| 13-10 | 8.7 | 4.2 | 34.6 | 9.6 | 12.5 | 2.2 | 19.1 | 1.5 | 1.2 | 2.21 | 1.01 |
| 13-11 | 8.7 | 4.0 | 17.6 | 24.3 | 18.9 | 2.8 | 17.1 | 1.6 | 1.4 | — | — |
| 13-12 | 8.9 | 4.2 | 26.4 | 14.6 | 16.0 | 2.5 | 17.5 | 1.6 | 1.2 | 1.62 | 0.74 |
| 13-13 | 9.0 | 4.4 | 27.9 | 14.4 | 15.3 | 2.5 | 18.9 | 1.5 | 1.4 | 1.30 | 0.77 |
| 13-14 | 9.2 | 4.2 | 17.2 | 23.8 | 18.8 | 2.7 | 17.9 | 1.7 | 1.5 | — | — |
| 13-15 | 8.4 | 4.2 | 19.7 | 20.9 | 18.6 | 2.7 | 17.7 | 1.4 | 1.5 | 0.40 | 0.16 |
| 13-16 | 8.2 | 4.3 | 23.0 | 17.1 | 17.3 | 2.8 | 19.3 | 1.5 | 1.5 | 0.97 | 0.42 |

TABLE 6-continued

Fatty acid composition of selfed seeds borne on $T_1$ plants derived from five primary Cpal2 transformants of *Arabidopsis thaliana*

| Plant | Fatty acid | | | | | | | | | | |
|---|---|---|---|---|---|---|---|---|---|---|---|
| | Non-epoxy fatty acids | | | | | | | | | Epoxy fatty acids | |
| No. | 16:0 | 18:0 | 18:1 | 18:2 | 18:3 | 20:0 | 20:1 | 22:0 | 22:1 | 18:1 | 18:2 |
| 13-17 | 8.3 | 4.1 | 15.7 | 23.9 | 19.9 | 2.8 | 17.6 | 1.6 | 1.9 | — | — |
| 17-1 | 7.6 | 4.1 | 15.8 | 23.7 | 19.6 | 2.6 | 20.3 | 1.7 | 1.7 | — | — |
| 17-2 | 8.3 | 4.1 | 16.4 | 24.4 | 20.1 | 2.3 | 16.8 | 1.5 | 1.4 | — | — |
| 17-3 | 8.1 | 4.1 | 16.4 | 24.3 | 20.0 | 2.5 | 17.6 | 1.6 | 1.4 | — | — |
| 21-1 | 8.1 | 4.3 | 26.9 | 14.5 | 15.0 | 2.9 | 19.9 | 1.5 | 1.5 | 1.64 | 0.63 |
| 21-2 | 8.2 | 4.0 | 27.9 | 11.8 | 13.2 | 2.5 | 19.8 | 1.7 | 1.5 | 2.18 | 0.91 |
| 21-3 | 8.8 | 3.7 | 16.4 | 24.4 | 20.6 | 2.5 | 17.3 | 1.7 | 1.4 | — | — |
| 21-4 | 7.9 | 3.9 | 19.6 | 19.8 | 17.8 | 2.7 | 18.7 | 1.7 | 1.7 | 0.66 | 0.46 |
| 21-5 | 7.2 | 4.2 | 26.5 | 12.9 | 14.4 | 3.0 | 21.5 | 0.9 | 1.8 | 1.78 | 0.84 |
| 21-6 | 8.3 | 4.2 | 27.4 | 13.9 | 15.4 | 2.6 | 19.9 | 1.7 | 1.5 | 1.66 | 0.65 |
| 21-7 | 7.2 | 4.2 | 26.8 | 13.5 | 13.4 | 3.0 | 21.9 | 1.7 | 1.8 | 1.74 | 0.80 |
| 21-8 | 7.4 | 3.8 | 16.3 | 23.6 | 19.4 | 3.2 | 19.2 | 1.7 | 1.9 | — | — |
| 21-9 | 7.2 | 4.0 | 28.1 | 11.8 | 13.5 | 3.0 | 22.5 | 1.9 | 1.9 | 2.15 | 1.05 |
| 21-10 | 7.2 | 4.2 | 26.1 | 13.8 | 14.6 | 3.0 | 22.3 | 1.7 | 1.8 | 1.64 | 0.82 |
| 21-11 | 7.1 | 4.2 | 29.2 | 11.5 | 12.7 | 3.0 | 22.5 | 1.8 | 1.8 | 2.20 | 1.09 |
| 21-12 | 7.2 | 4.1 | 26.2 | 13.6 | 14.2 | 3.1 | 22.4 | 1.8 | 1.9 | 1.71 | 0.80 |
| 21-13 | 7.1 | 4.3 | 33.7 | 7.1 | 10.0 | 2.7 | 24.1 | 2.0 | 1.8 | 3.05 | 1.47 |
| 21-14 | 7.4 | 3.7 | 16.9 | 21.9 | 19.6 | 3.1 | 19.2 | 1.8 | 2.0 | 0.29 | tr |
| 21-15 | 7.7 | 3.6 | 15.6 | 24.3 | 20.2 | 2.9 | 18.1 | 1.8 | 1.8 | — | — |

EXAMPLE 8

Fatty Acid Analysis of Cpal2 Transgenic Linola Plants

The binary plasmid construct described above comprising the Cpal2 cDNA clone (FIG. 9) was transformed into *Agrobacterium tumefaciens* strain AGL1, using electroporation. The transformed *A. tumefaciens* was used to infect *Linum usitatissimum* var. Eyre explants as described by Lawrence et al (1989), except that MS media was used as the basal medium for the induction of roots on regenerated shoot material.

Two primary Linola transformants (T0 plants) designated AP20 and AP21 were confirmed as being transgenic by PCR using primers directed against the Cpal2 gene and by showing that these plants were kanamycin resistant. Ten T1 seeds from each plant were analysed individually for fatty acid composition using standard techniques.

As shown in Table 7, seed from AP20 segregated into 3 classes, comprised of three seeds with no vernolic acid, two having greater than 0.7% vernolic acid, and five having intermediate levels (0.13–0.47%) of vernolic acid.

Similarly, seeds from AP21 segregated into 3 classes comprised of five seeds having no vernolic acid, two having greater than 0.25% vernolic acid and three having an intermediate level (0.09–0.14%) of vernolic acid (Table 8).

Thus, a total of twelve seeds were obtained which contained vernolic acid. Eight of the twelve AP20 and AP21 seeds containing vernolic acid also contained 12,13-epoxy-9,15-octadecadienoic acid.

TABLE 7

Fatty acid composition of 10 individual T1 seeds from Linola Cpal2 primary transformants AP20

| | Non-epoxy fatty acids | | | | | | | | | Epoxy fatty acids | |
|---|---|---|---|---|---|---|---|---|---|---|---|
| $T_1$ seed | 16:0 | 18:0 | 18:1 | 18:2 | 18:3 | 20:0 | 20:1 | 22:0 | 22:1 | 18:1 | 18:2 |
| 1 | 6.4 | 3.6 | 17.8 | 68.1 | 2.0 | 0.2 | — | 0.6 | — | — | — |
| 2 | 6.0 | 3.5 | 25.4 | 60.8 | 1.4 | 0.2 | 0.2 | — | — | 0.70 | 0.23 |
| 3 | 6.0 | 3.9 | 20.4 | 64.6 | 2.1 | 0.3 | 0.6 | — | — | — | — |
| 4 | 6.3 | 3.5 | 28.3 | 57.3 | 1.3 | 0.2 | 0.2 | 1.4 | — | 0.34 | 0.28 |
| 5 | 5.2 | 4.8 | 24.9 | 61.2 | 1.6 | 0.3 | 0.2 | 0.1 | — | 0.37 | — |
| 6 | 5.8 | 4.1 | 23.3 | 63.1 | 1.9 | 0.2 | 0.2 | 0.2 | — | 0.47 | — |
| 7 | 5.9 | 4.3 | 21.7 | 64.1 | 2.2 | 0.2 | 0.2 | 0.2 | — | 0.13 | 0.12 |
| 8 | 5.9 | 3.3 | 22.3 | 65.2 | 2.0 | 0.2 | 0.2 | 0.1 | 0.2 | — | — |
| 9 | 5.6 | 4.0 | 25.2 | 61.4 | 1.7 | 0.2 | 0.2 | 0.1 | — | 0.84 | — |
| 10 | 6.2 | 4.4 | 27.4 | 57.9 | 1.7 | 0.2 | 0.2 | 0.2 | — | 0.54 | — |

TABLE 8

Fatty acid composition of 10 individual T1 seeds from Linola Cpal2 primary transformant AP21

| | Non-epoxy fatty acids | | | | | | | | | Epoxy fatty acids | |
|---|---|---|---|---|---|---|---|---|---|---|---|
| $T_1$ seed | 16:0 | 18:0 | 18:1 | 18:2 | 18:3 | 20:0 | 20:1 | 22:0 | 22:1 | 18:1 | 18:2 |
| 1 | 6.1 | 4.2 | 35.2 | 50.8 | 1.3 | — | — | — | 2.0 | — | — |
| 2 | 5.7 | 5.0 | 32.9 | 53.3 | 1.4 | 0.2 | 0.2 | 0.2 | | 0.14 | 0.21 |
| 3 | 5.9 | 4.0 | 35.1 | 50.8 | 1.3 | 0.2 | 0.2 | 0.1 | 1.5 | — | — |
| 4 | 7.5 | 4.1 | 38.8 | 45.5 | 1.2 | 0.2 | 0.3 | — | 1.7 | — | — |
| 5 | 5.8 | 5.0 | 28.8 | 57.3 | 1.3 | 0.2 | 0.2 | 0.1 | — | 0.37 | 0.06 |
| 6 | 5.8 | 5.0 | 44.1 | 41.4 | 1.4 | 0.2 | 0.2 | 0.2 | — | — | — |
| 7 | 6.5 | 4.5 | 27.9 | 58.6 | 1.3 | 0.2 | 0.1 | 0.1 | — | — | — |
| 8 | 6.9 | 4.6 | 37.6 | 48.1 | 1.2 | — | — | — | — | 0.10 | 0.19 |
| 9 | 6.2 | 4.7 | 33.7 | 52.1 | 1.3 | 0.2 | 0.2 | 0.2 | — | 0.09 | 0.07 |
| 10 | 6.1 | 4.8 | 29.7 | 56.6 | 1.3 | 0.2 | 0.2 | 0.1 | — | 0.25 | 0.04 |

Four T1 plants were established from the kanamycin-resistant seedlings of AP20. All four plants were subsequently shown to produce vernolic acid in their T2 seed (Table 9). Levels of 18:2 epoxy fatty acids were not analysed in these T2 seed.

TABLE 9

Fatty acid composition of T2 seeds from Linola Cpal2 T1 progeny of AP20

| | Non-epoxy fatty acids | | | | | | | | | epoxy fatty acid |
|---|---|---|---|---|---|---|---|---|---|---|
| $T_2$ seed | 16:0 | 18:0 | 18:1 | 18:2 | 18:3 | 20:0 | 20:1 | 22:0 | 22:1 | 18:1 |
| A | 3.4 | 3.0 | 27.4 | 65.5 | 0.6 | na | na | na | na | 0.06 |
| B | 3.5 | 3.1 | 30.2 | 62.6 | 0.6 | na | na | na | na | 0.07 |
| C | 3.6 | 2.7 | 33.3 | 59.8 | 0.6 | na | na | na | na | 0.07 |
| D | 3.4 | 3.1 | 28.2 | 64.6 | 0.6 | na | na | na | na | 0.11 | na. = not analysed

EXAMPLE 9

Producing Epoxy Fatty Acids in Transgenic Organisms

Production of an oil rich in vemolic acid was achieved by transforming the epoxygenase gene described herein, in particular SEQ ID NO:1, into *Arabidopsis thaliana*, as described in the preceding Examples. As shown in Table 5, transgenic *A. thaliana* lines expressing SEQ ID NO:1 produce high levels of vernolic acid in their seeds relative to other fatty acids. In particular, in one transgenic line (Cpal-17), the vernolic acid produced is as much as 15.2 % (w/w) of total seed fatty acid content.

Production of an oil rich in vernolic acid is also achieved by transforming the epoxygenase gene described herein, in any one of SEQ ID NOs: 1, 3, 5, 19 or 20 and preferably any one of SEQ ID NOs:1 or 3 or 5, into any oil accumulating organism that normally has very high levels of linoleic acid and minimal other competing enzyme activities capable of utilising linoleic acid as a substrate. The genetic sequences of the invention are placed operably under the control of a promoter which produces high-level expression in oilseed, for example the napin seed-specific promoter.

In one alternative approach to the transformation of *A. thaliana*, high-linoleic genotypes of flax, sunflower, corn or safflower are transformed with the epoxygenase of the invention. High levels of vernolic acid are produced by the transgenic plants during seed oil synthesis, when the epoxygenase gene is expressed at high levels.

Alternatively, Linola® (=low linolenic acid) flax is transformed with the epoxygenase of the invention. High levels of vernolic acid are produced by the transgenic Linola® flax plants during seed oil synthesis, when the epoxygenase gene is expressed at high levels.

Additionally, the inventors have shown that labelled vernolic acid fed to developing flax seeds is not degraded but is incorporated into storage lipids at all three positions of the triglyceride molecule (see Example 10). Consistent with these data, high levels of vernolic acid synthesised by the introduced epoxygenase are readily deposited into the seed oil triglycerides of this species.

EXAMPLE 10

Incorporation of Oleic Acid and Vernolic Acid into the Lipids of Developing Linseed Cotyledons Detached developing linseed cotyledons (six pairs in each incubation, duplicate incubations) at mid stage of seed development (20 days after flowering) were incubated with 10 nmol of the ammonium salts of either $[1-^{14}C]$vernolic acid (specific activity 3000 d.p.m./nmol) or $[1-^{14}C]$oleic acid (specific activity 5000 d.p.m./nmol) in 0.2 ml phosphate buffer pH 7.2 for 30 min at 30° C. The cotyledons were then rinsed three times with 1 ml of distilled water and either extracted immediately in an Ultra Turrax according to Bligh and Dyer (1959) or incubated further in 0.5 m. 0.1 M phosphate buffer pH 7.2 for 90 or 270 min before extraction.

An aliquot of the lipids in the chloroform phase was methylated and separated on silica gel TLC plates in n-hexane/diethylether/acetic acid (85:15:1). The rest of the lipids in the chloroform phase of each sample were applied on two separate silica gel TLC plates and the plates were developed in chloroform/methanol/acetic acid/water (85:15:10:3.5 by vol) for polar lipids separation and in n-hexane/diethylether/acetic acid (60:40:1.5) for neutral lipid separation. Lipid areas with migration corresponding to authentic standards were removed and radioactivity in each lipid were quantified by liquid scintillation counting.

Figure 12:
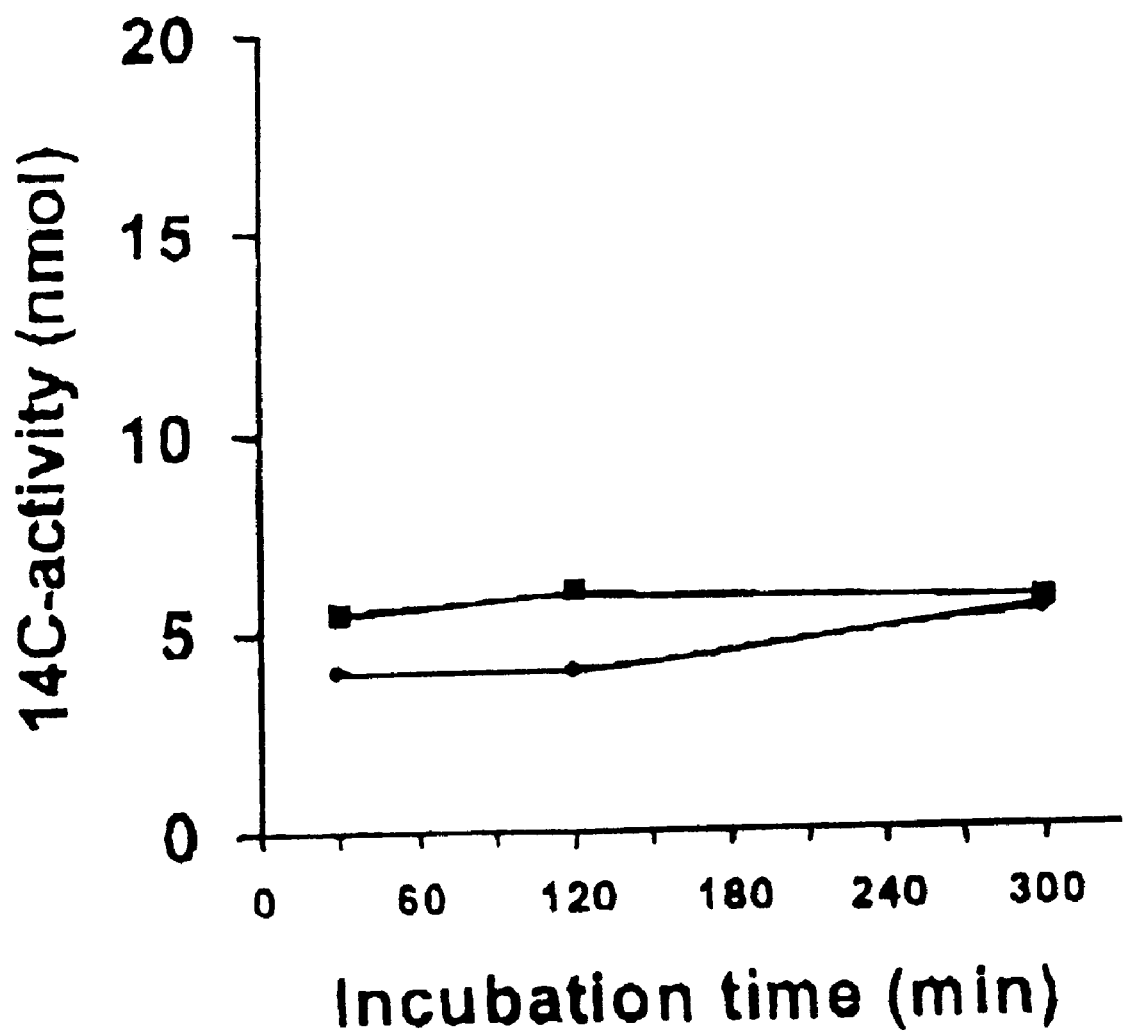
FIG. 12 is a graphical representation showing the incorporation of $^{14}$C-label into the chloroform phase obtained from lipid extraction of linseed cotyledons during labelled-substrate feeding. Symbols used; ♦, [$^{14}$C]oleic acid feeding; ■, [$^{14}$C]vernolic acid feeding.

The recovery of $^{14}C$-label in the chloroform phase is depicted in FIG. 12. Somewhat more than half of added radioactivity from both [$^{14}C$]oleic acid and [$^{14}C$]vernolic acid was taken up by the cotyledons and recovered as lipophilic substances after the 30 min pulse labelling. This quantity remained virtually unchanged during the further 270 min of incubation with both substrates. Separation of radioactive methylesters of the lipids showed that most of the radioactivity (92%) from [$^{14}C$]vernolic acid feeding experiments resided in compounds with the same migration as methyl-vernoleate indicating that the epoxy group remained intact in the linseed cotyledons throughout the 270 min incubation.

Figure 13:
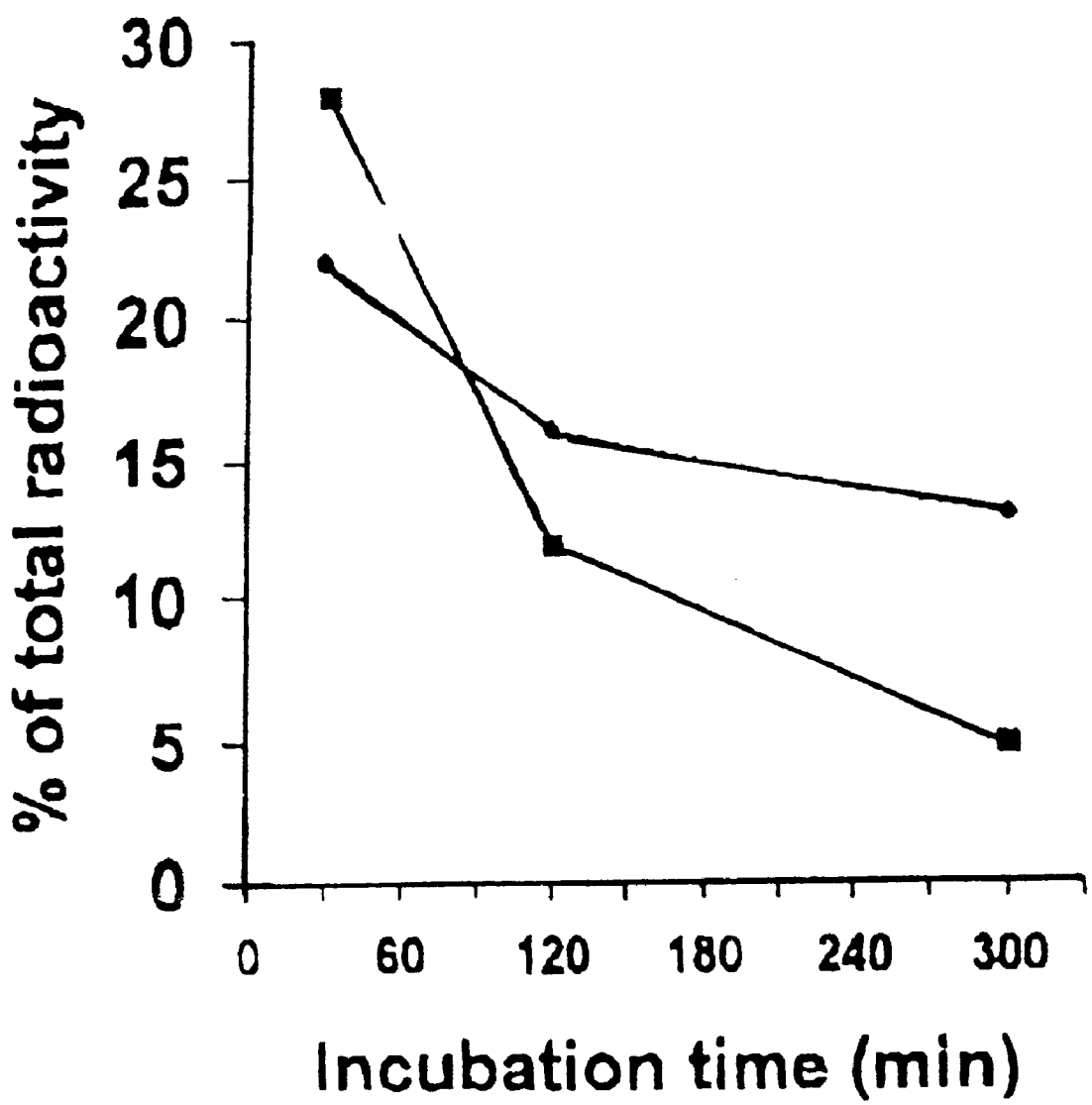
FIG. 13 is a graphical representation showing the incorporation of $^{14}$C-label into the phosphatidylcholine of linseed cotyledons during labelled-substrate feeding. Symbols used; ♦, [$^{14}$C]oleic acid feeding; ■, [$^{14}$C]vernolic acid feeding.

About 28% of the activity from [$^{14}C$]vernolic acid feeding which was present in the chloroform phase resided in phosphatidylcholine after 30 min and the radioactivity decreased to only 5% at 300 min of incubation (FIG. 13).

About 22% of the activity from [$^{14}C$]oleic acid feeding which was present in the chloroform phase resided in phosphatidylcholine after 30 min and the radioactivity decreased to about 11% at 300 min of incubation (FIG. 13).

Figure 14:
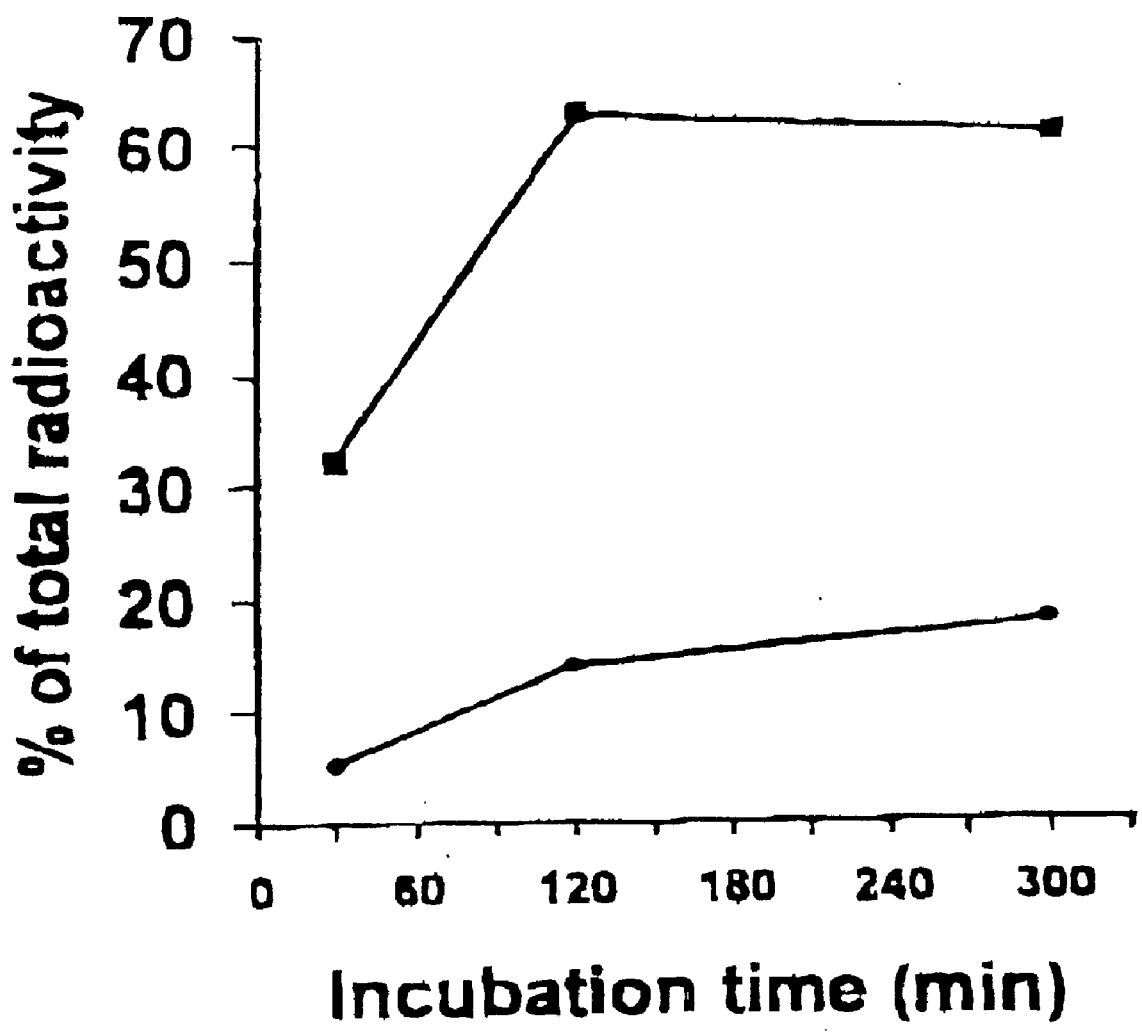
FIG. 14 is a graphical representation showing the incorporation of $^{14}$C-label into the triacylglycerols of linseed cotyledons during labelled-substrate feeding. Symbols used; ♦, [$^{14}$C]oleic acid feeding; ■, [$^{14}$C]vernolic acid feeding.

About 32% of the activity from [$^{14}C$]vernolic acid feeding which was present in the chloroform phase resided in triacylglycerols after 30 min and the radioactivity increased to over 60% at 300 min of incubation (FIG. 14). The diacylglycerols contained some 24% of the activity in the [14C]vernolic acid feeding experiments and this quantity remained rather constant over the incubation periods.

About 5% of the activity from [$^{14}C$]oleic acid feeding which was present in the chloroform phase resided in triacylglycerols after 30 min and the radioactivity increased to 18% at 300 min of incubation (FIG. 14). The diacylglycerols contained some 19% of the activity after 30 min in the [$^{14}C$]oleic acid feeding experiments and this quantity remained rather constant over the incubation periods.

The above experiment shows that linseed cotyledons do not metabolise the epoxy group of vernolic acid to any great extent. Further it shows that linseed cotyledons possess mechanisms to efficiently remove vernolic acid from membrane lipids and incorporate them into triacylglycerols.

EXAMPLE 11

Cloning of Δ12-epoxygenase Genes from other Epoxy Acid Containing Species

Homologues of the Cpal2 Δ12-epoxygenase gene are obtained from other species which are rich in epoxy fatty acids, by cloning the members of the gene family of Δ12 mixed function monooxygenases that are highly expressed in developing seeds and comparing their amino acid sequence to those of known Δ12-desaturase and Δ12-epoxygenase sequences. Such genes are cloned either by screening developing seed cDNA libraries with genetic probes based on either the Cpal2 gene (SEQ ID NO: 1) or the D12V fragment (SEQ ID NO: 7), or by amplifying PCR fragments using primers designed against conserved sequences of the plant Δ12 mixed function monooxygenases, as described herein. Putative Δ12-epoxygenase sequences show greater overall sequence identity to the Δ12-epoxygenase sequences disclosed herein, than to the known Δ12-desaturase sequences.

In one example of this approach, a full-length Δ12-epoxygenase-like sequence was obtained from an unidentified Crepis sp. containing high levels of vernolic acid in its seed oils and known not to be *Crepis palaestrina*. Poly(A)+ RNA was isolated from developing seeds of this Crepis sp. using a QuickPrep Micro mRNA purification kit (Pharmacia Biotechnology) and used to synthesise an oligosaccharide d(T)-primed double-stranded cDNA. The double stranded cDNA thus obtained was then ligated to EcoR1/NotI adaptors (Pharmacia Biotechnology) and a cDNA library was constructed using the ZAP-cDNA Gigapack cloning kit (Stratagene). The cDNA library on Hybond N+membrane filters (Amersham) was screened with the random-labelled D12V fragment (SEQ ID NO: 7) derived from *Crepis alpina* as prescribed by the manufacturer, using standard hybridisation conditions. This resulted in the purification of a recombinant bacteriophage designated CrepX.

The nucleotide sequence of the CrepX cDNA was determined and is set forth in SEQ ID NO: 3. The deduced amino acid sequence of CrepX (SEQ ID NO: 4) comprises a 374 amino acid protein having 97% identity to the Cpal2 Δ12-epoxygenase sequence, but only 57% identity to the *Arabidopsis thaliana* L26296 Δ12-desaturase sequence. This clearly demonstrates the presence of a gene in another Crepis sp. having high vernolic acid content, which gene is highly homologous to the Cpal2 Δ12-epoxygenase gene and is clearly not a desaturase gene.

In a second example of this approach, a partial Δ12-epoxygenase-like sequence was obtained from the vernolic acid-containing species *Vernonia galamensis*. First strand cDNA templates were prepared from total RNA isolated from developing seeds of *V. galamensis* using standard procedures.

A PCR fragment (550 nucleotides in length), designated as Vgal1, was obtained by amplifying the single-stranded cDNA using primers derived from the deduced amino acid sequence of plant mixed function monooxygenases. The nucleotide sequence of the amplified DNA was determined using standard procedures and is set forth in SEQ ID NO:5.

Alignment of the deduced amino acid sequence of the Vgal1 PCR fragment (SEQ ID NO:6) with the full sequence of Cpal2 Δ12-epoxygenase and the *Arabidopsis thaliana* L26296 Δ12-desaturase (FIG. 2) demonstrates that the amplified Vgal1 sequence encodes an amino acid sequence which corresponds to the region spanning amino acid residues 103–285 of the Cpal2 polypeptide. Within this region, the Vgal1 sequence showed greater amino acid identity with the Cpal2 Δ12-epoxygenase sequence (67%) than with the *A. thaliana* Δ12-desaturase sequence (60%), suggesting that the amplified DNA corresponds to an epoxygenase rather than a desaturase sequence.

Those skilled in the art will be aware that the present invention is subject to variations and modifications other than those specifically described herein. It is to be understood that the invention includes all such variations and modifications. The invention also includes all such steps, features, compositions and compounds referred to or indicated in this specification, individually or collectively, and any and all combinations of any two or more of said steps or features.

All references cited in the present application arte incorporated by reference herein in their entireties.

REFERENCES

1. An et al. (1985) EMBO J. 4:277–284.
2. Ausubel, F. M., Brent, R., Kingston, RE, Moore, D. D., Seidman, J. G., Smith, J. A., and Struhl, K. (1987). In: Current Protocols in Molecular Biology. Wiley Interscience (ISBN 047150338).
3. Badami, R. C., and Patil, K. B. (1981) Progress in Lipid Research, 19, 119–53.
4. Bafor, M., Smith, M. A., Jonsson, L., Stobart, K. and Stymne, S. (1993) Arch. Biochem. Biophys. 303, 145–151.
5. Bafor, M., Banas, A., Wiberg, E., Lenman, M., Stahl, U. and Stymne, S. (1997) In: Williams, J. P., Mobasher, K. U., Lem, N. W. (eds) Physiology, biochemistry and molecular biology of plant lipids. Kluwer Academic Publisher, Dordrecht. In-press.
6. Blee and Schuber (1990) J. Biol. Chem. 265, 12887–12894.
7. Blee, E., Wilcox, A. L., Mamett, J. M., Schuber, F. (1993) J. Biol. Chem. 268, 1798–1715.
8. Blee, E., Stahl, S., Schuber, F. and Stymne, S. (1994) Biochem. Biophys. Res. Comm. 197, 778–784
9. Bligh, E. G. and Dyer, W. J. (1959) Can. J. Biochem. Physiol. 230, 379–288.
10. Bozak, K. R., Yu, H., Sirevag, R. and Christoffersen, R. E. (1990) Proc. Natl. Acad. Sci. USA 87, 3904–3908.
11. Christou, P., McCabe, D. E., Swain, W. F. (1988). Plant Physiol 87, 671–674.
12. Crossway et al. (1986) Mol. Gen. Genet. 202,179–185.
13. Devereux, J., Haeberli, P. and Smithies, O. (1984). Nucl. Acids Res. 12, 387–395.
14. Dolferus et al. Plant Physiol. (1994) 105, 1075–1087.
15. Engeseth, N. & Stymne, S. (1996) Planta 198, 238–245
16. Fromnim et al. (1985) Proc. Natl. Acad. Sci. (USA) 82,5824–5828.
17. Haseloff, J. and Gerlach, W. L. (1988). Nature 334, 586–594.
18. Herrera-Estrella et al. (1983a) Nature 303, 209–213.
19. Herrera-Estrella et al. (1983b) EMBO J. 2, 987–995.
20. Herrera-Estrella et al. (1985) In: Plant Genetic Engineering, Cambridge University Press, N.Y., pp 63–93.
21. Kohn, G., Hartmann, E., Stymne, S. & Beutelmann, P. (1994) J. Plant Physiol. 144, 265–271
22. Krens, F. A., Molendijk, L., Wullems, G. J. and Schilperoort, R. A. (1982). Nature 296, 72–74.
23. Lawrence, G. J., Ellis, J. G., Finnegan, E. J., Dennis, E. S. and Peacock, W. J. (1989) In: Breeding Research: The Key to Survival of the Earth (Iyama, S. and Takeda, G. eds) 6th International Congress of SABRAO. pp 535–538.
24. Lazo, G. R., Stein, P. A. and Ludwig, R. A. (1991). Bio/technology 9, 963–967.
25. Needleman and Wunsch (1970) J. Mol. Biol. 48, 443–453.
26. Pazkowski et al. (1984) EMBO J. 3, 2717–2722.
27. Pietrzak, M., Shillito, R. D., Hohn, T. and Potrykus, I. (1986). Nucl. Acids Res. 14,5857–5868.
28. Sanger, F., Nicklin, S. and Coulson, A. R. (1977). Proc. Natl. Acad. Sci. (USA) 72, 5463–5467.
29. Shanklin, J., Whittle, E. and Fox, B. G. (1994) Biochemistry 33, 12787–12794.
30. Valvekens et al. (1988)Proc. Natl Acad. Sci. (USA) 85, 5536–5540.

---

We claim:

1. An isolated nucleic acid molecule from the plant Crepis that encodes a polypeptide which catalyzes the epoxygenation of a carbon double bond at the delta-12 position of a fatty acid wherein said nucleic acid comprises a nucleotide sequence selected from the group consisting of:

(i) the sequence set forth in SEQ ID NO: 1;

(ii) a sequence encoding the amino acid sequence set forth in SEQ ID NO: 2; and (iii) a sequence that is complementary to (i) or (ii).

2. The isolated nucleic acid molecule according to claim 1, wherein the plant produces high levels of vernolic acid in its seed.

3. The isolated nucleic acid molecule according to claim 1, wherein the plant is *Crepis palaestrina*.

4. An isolated nucleic acid molecule comprising the nucleotide sequence set forth in SEQ ID NO: 1.

5. A genetic construct which comprises the isolated nucleic acid molecule according to claim 1 operably connected to a promoter sequence, wherein said nucleic acid molecule is capable of being transcribed in the sense or antisens orientation relative to the direction of in vivo transcription of a naturally-occurring epoxygenase gene.

6. An isolated nucleic acid molecule from the plant Crepis that encodes a 12-epoxygenase polypeptide which catalyzes the epoxygenation of a carbon double bond in linoleic acid, and comprises a nucleotide sequence selected from the group consisting of:

(i) the sequence set forth in SEQ ID NO: 1; and (ii) a sequence encoding the amino acid sequence set forth in SEQ ID NO: 2.

7. The genetic construct of claim 5 wherein the promoter is a napin seed-specific promoter.

8. The genetic construct of claim 5 wherein said genetic construct is included within a binary plasmid.

* * * * *

UNITED STATES PATENT AND TRADEMARK OFFICE
CERTIFICATE OF CORRECTION

PATENT NO.    : 6,329,518 B1
DATED         : December 11, 2001
INVENTOR(S)   : Green et al.

It is certified that error appears in the above-identified patent and that said Letters Patent is hereby corrected as shown below:

Title page,
Item [56], References Cited, OTHER PUBLICATIONS,
In the Bafor et al. reference, please replace "(cis-12-Eposyoctadeca-cis-90enoate)" with -- (cis-12-Epoxyoctadeca-cis-9-enoate) --.
In the Shanklin et al. reference, please replace "Stearoyl-CoA Sesaturase," with -- Stearoyl-CoA Desaturase, --.
In the Valvekens et al. reference, please replace "knamycin selection" with -- kanamycin selection --.

Column 1,
Line 15, please replace "Crepeis" with -- Crepis --.

Column 2,
Line 23, please replace "vemolic acid" with -- vernolic acid --.
Line 41, please replace "viork" with -- work --.

Column 3,
Lines 61-62, please replace "imrnuno-logically" with -- immunologically --.

Column 28,
Line 64, replace "palaestrina" with -- palaestina --.

Column 29,
Lines 23, 26 and 62, replace "palaestrina" in all occurrences with -- palaestina --.
Line 27, replace "ocalized" with -- localized --.
Line 28, replace "embrane" with -- membrane --.

Column 30,
Lines 8, 21, 47 and 50, replace "palaestrina" in all occurrences with -- palaestina --.

Column 31,
Line 62, replace "palaestrina" with -- palaestina --.

UNITED STATES PATENT AND TRADEMARK OFFICE
CERTIFICATE OF CORRECTION

PATENT NO. : 6,329,518 B1
DATED : December 11, 2001
INVENTOR(S) : Green et al.

It is certified that error appears in the above-identified patent and that said Letters Patent is hereby corrected as shown below:

<u>Column 42,</u>
Line 9, replace "palaestrina" with -- palaestina --.

<u>Column 82,</u>
Line 42, replace "antisens" with -- antisense --.
Line 46, replace "12-epoxygenase" with -- delta-12-epoxygenase --.

Signed and Sealed this

Twenty-fourth Day of September, 2002

*Attest:*

JAMES E. ROGAN
*Attesting Officer*  *Director of the United States Patent and Trademark Office*

UNITED STATES PATENT AND TRADEMARK OFFICE
CERTIFICATE OF CORRECTION

PATENT NO.    : 6,329,518 B1
DATED         : December 11, 2001
INVENTOR(S)   : Green et al.

It is certified that error appears in the above-identified patent and that said Letters Patent is hereby corrected as shown below:

Title page,
Item [56], References Cited, OTHER PUBLICATIONS,
In the Bafor et al. reference, please replace "(cis-12-Eposyoctadeca-cis-90enoate)" with -- (cis-12-Epoxyoctadeca-cis-9-enoate) --;
In the Shanklin et al. reference, please replace "Stearoyl-CoA Sesaturase," with -- Stearoyl-CoA Desaturase, --;
In the Valvekens et al. reference, please replace "knamycin selection" with -- kanamycin selection --.

Column 1,
Line 15, please replace "Crepeis" with -- Crepis --.

Column 2,
Line 23, please replace "vemolic acid" with -- vernolic acid --.
Line 41, please replace "viork" with -- work --.

Column 3,
Lines 61-62, please replace "imrnuno-logically" with -- immunologically --.

Column 28,
Line 64, replace "palaestrina" with -- palaestina --.

Column 29,
Lines 23, 26 and 62, replace "palaestrina" in all occurrences with -- palaestina --.
Line 27, replace "ocalized" with -- localized --.
Line 28, replace "embrane" with -- membrane --.

Column 30,
Lines 8, 21, 47 and 50, replace "palaestrina" in all occurrences with -- palaestina --.

Column 31,
Line 62, replace "palaestrina" with -- palaestina --.

UNITED STATES PATENT AND TRADEMARK OFFICE
CERTIFICATE OF CORRECTION

PATENT NO. : 6,329,518 B1
DATED : December 11, 2001
INVENTOR(S) : Green et al.

It is certified that error appears in the above-identified patent and that said Letters Patent is hereby corrected as shown below:

<u>Column 42,</u>
Line 9, replace "palaestrina" with -- palaestina --.

<u>Column 82,</u>
Line 42, replace "antisens" with -- antisense --.
Line 46, replace "12-epoxygenase" with -- delta-12-epoxygenase --.

Signed and Sealed this

Fifteenth Day of October, 2002

*Attest:*

JAMES E. ROGAN
*Attesting Officer*     *Director of the United States Patent and Trademark Office*